(12) United States Patent
Mao et al.

(10) Patent No.: US 10,883,130 B2
(45) Date of Patent: Jan. 5, 2021

(54) BIOSYNTHETIC PRODUCTION OF STEVIOL GLYCOSIDES REBAUDIOSIDE J AND REBAUDIOSIDE N

(71) Applicant: Conagen Inc., Bedford, MA (US)

(72) Inventors: Guohong Mao, Burlington, MA (US); Michael Batten, Westford, MA (US); Phillip Hunt, Tewksbury, MA (US); Oliver (Xiaodan) Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 0 days.

(21) Appl. No.: 16/679,032

(22) Filed: Nov. 8, 2019

(65) Prior Publication Data

US 2020/0087695 A1    Mar. 19, 2020

Related U.S. Application Data

(63) Continuation of application No. PCT/US2019/021876, filed on Mar. 12, 2019.

(60) Provisional application No. 62/695,252, filed on Jul. 9, 2018, provisional application No. 62/682,260, filed on Jun. 8, 2018, provisional application No. 62/641,590, filed on Mar. 12, 2018.

(51) Int. Cl.
*C12P 19/56* (2006.01)
*C12N 15/82* (2006.01)
*C12N 9/10* (2006.01)

(52) U.S. Cl.
CPC ............ *C12P 19/56* (2013.01); *C12N 9/1081* (2013.01); *C12N 15/8245* (2013.01); *C12Y 204/01013* (2013.01); *C12Y 204/99* (2013.01)

(58) Field of Classification Search
CPC ... C12P 19/56; C12N 15/8245; C12N 9/1081; C12N 9/1051; C12Y 204/99; C12Y 204/01013; C12Y 204/01; A23L 27/36; A23L 27/30
See application file for complete search history.

(56) References Cited

U.S. PATENT DOCUMENTS

| | | |
|---|---|---|
| 9,957,540 B2 | 5/2018 | Mikkelsen et al. |
| 2006/0143729 A1 | 6/2006 | Alexandrov et al. |
| 2012/0107362 A1 | 5/2012 | Hofmann et al. |
| 2014/0329281 A1 | 11/2014 | Houghton-Larsen et al. |
| 2017/0112176 A1 | 4/2017 | Markosyan et al. |
| 2017/0275666 A1 | 9/2017 | Prakash et al. |
| 2017/0332673 A1 | 11/2017 | Philippe et al. |
| 2019/0338332 A1 | 11/2019 | Tao et al. |
| 2020/0002742 A1 | 1/2020 | Mao et al. |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
International Search Report and Written Opinion for Application No. PCT/2019/21876 dated Jul. 17, 2019.
U.S. Appl. No. 16/506,892, filed Jul. 9, 2019, Mao et al.
PCT/2019/21876, Jul. 17, 2019, International Search Report and Written Opinion.
Chaturvedula et al., Isolation, NMR Spectral Analysis and Hydrolysis Studies of a Hepta Pyranosyl Diterpene Glycoside from Stevia rebaudiana Bertoni. Biomolecules. Sep. 30, 2013;3(4):733-40. doi: 10.3390/biom3040733.

* cited by examiner

*Primary Examiner* — Delia M Ramirez
(74) *Attorney, Agent, or Firm* — Wolf, Greenfield & Sacks, P.C.; Karen K. Chan

(57) ABSTRACT

The present disclosure relates to the production of steviol glycosides rebaudioside J and rebaudioside N through the use of rebaudioside A as a substrate and a biosynthetic pathway involving various 1,2 RhaT-rhamnosyltransferases.

17 Claims, 9 Drawing Sheets

Specification includes a Sequence Listing.

SEQUENCE LISTING

<160> NUMBER OF SEQ ID NOS: 20

<210> SEQ ID NO 1
<211> LENGTH: 462
<212> TYPE: PRT
<213> ORGANISM: Oryza sativa

<400> SEQUENCE: 1

```
Met Asp Ser Gly Tyr Ser Ser Tyr Ala Ala Ala Gly Met His
1               5                   10                  15

Val Val Ile Cys Pro Trp Leu Ala Phe Gly His Leu Pro Cys Leu
            20                  25                  30

Asp Leu Ala Gln Arg Leu Ala Ser Arg Gly His Arg Val Ser Phe Val
        35                  40                  45

Ser Thr Pro Arg Asn Ile Ser Arg Leu Pro Pro Val Arg Pro Ala Leu
    50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
        115                 120                 125

Val Phe His His Trp Ala Ala Ala Ala Leu Glu His Lys Val Pro
    130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Gly
                165                 170                 175

Gln Gly Arg Pro Ala Ala Ala Pro Thr Phe Glu Val Ala Arg Met Lys
            180                 185                 190

Leu Ile Arg Thr Lys Gly Ser Ser Gly Met Ser Leu Ala Glu Arg Phe
        195                 200                 205

Ser Leu Thr Leu Ser Arg Ser Ser Leu Val Val Gly Arg Ser Cys Val
    210                 215                 220

Glu Phe Glu Pro Glu Thr Val Pro Leu Leu Ser Thr Leu Arg Gly Lys
225                 230                 235                 240

Pro Ile Thr Phe Leu Gly Leu Met Pro Pro Leu His Glu Gly Arg Arg
                245                 250                 255

Glu Asp Gly Glu Asp Ala Thr Val Arg Trp Leu Asp Ala Gln Pro Ala
            260                 265                 270

Lys Ser Val Val Tyr Val Ala Leu Gly Ser Glu Val Pro Leu Gly Val
        275                 280                 285

Glu Lys Val His Glu Leu Ala Leu Gly Leu Glu Leu Ala Gly Thr Arg
```

```
                290                 295                 300
Phe Leu Trp Ala Leu Arg Lys Pro Thr Gly Val Ser Asp Ala Asp Leu
305                 310                 315                 320

Leu Pro Ala Gly Phe Glu Arg Thr Arg Gly Arg Gly Val Val Ala
                325                 330                 335

Thr Arg Trp Val Pro Gln Met Ser Ile Leu Ala His Ala Ala Val Gly
                340                 345                 350

Ala Phe Leu Thr His Cys Gly Trp Asn Ser Thr Ile Glu Gly Leu Met
            355                 360                 365

Phe Gly His Pro Leu Ile Met Leu Pro Ile Phe Gly Asp Gln Gly Pro
        370                 375                 380

Asn Ala Arg Leu Ile Glu Ala Lys Asn Ala Gly Leu Gln Val Ala Arg
385                 390                 395                 400

Asn Asp Gly Asp Gly Ser Phe Asp Arg Glu Gly Val Ala Ala Ala Ile
                405                 410                 415

Arg Ala Val Ala Val Glu Glu Glu Ser Ser Lys Val Phe Gln Ala Lys
                420                 425                 430

Ala Lys Lys Leu Gln Glu Ile Val Ala Asp Met Ala Cys His Glu Arg
            435                 440                 445

Tyr Ile Asp Gly Phe Ile Gln Gln Leu Arg Ser Tyr Lys Asp
        450                 455                 460

<210> SEQ ID NO 2
<211> LENGTH: 1389
<212> TYPE: DNA
<213> ORGANISM: Oryza sativa

<400> SEQUENCE: 2
atggattcgg gttactcttc ctcctatgcg gcggctgcgg gtatgcacgt tgttatctgt      60
ccgtggctgg cttttggtca cctgctgccg tgcctggatc tggcacagcg tctggcttca     120
cgcggccatc gtgtcagctt cgtgtctacc ccgcgcaata tttcgcgtct gccgccggtt     180
cgtccggcac tggctccgct ggttgcattt gtcgctctgc cgctgccgcg cgtggaaggt     240
ctgccggatg gtgcggaaag taccaacgac gtgccgcatg atcgcccgga catggttgaa     300
ctgcaccgtc gtgcattcga tggtctggca gcaccgtttt ccgaatttct gggtacggcg     360
tgcgccgatt gggtgatcgt tgacgtcttt catcactggg cggcggcggc ggcgctggaa     420
cataaagttc gtgtgcaat gatgctgctg ggctcagctc acatgattgc gtcgatcgca     480
gaccgtcgcc tggaacgtgc agaaaccgaa agtccggctg cggccggcca gggtcgcccg     540
gcagctgcgc cgaccttcga agtggcccgc atgaaactga ttcgtacgaa aggcagctct     600
ggtatgagcc tggcagaacg ctttagtctg accctgtccc gtagttccct ggtggttggt     660
cgcagttgcg ttgaatttga accggaaacc gtcccgctgc tgtccacgct gcgtggtaaa     720
ccgatcacct ttctgggtct gatgccgccg ctgcatgaag gcgtcgcga agatggtgaa     780 gacgcaacgg tgcgttggct ggatgcacag ccggctaaaa gcgtcgtgta tgtcgccctg     840
ggctctgaag tgccgctggg tgtggaaaaa gttcacgaac tggcactggg cctggaactg     900
gctggcaccc gcttcctgtg gcactgcgt aaaccgacgg tgtgagcga tgcggacctg     960 ctgccggccg ttttgaaga acgtacccgc ggccgtggtg ttgtcgcaac gcgttgggtc    1020
ccgcaaatga gcattctggc gcatgccgca gtgggcgcct ttctgaccca ctgtggttgg    1080
aacagcacga tcgaaggcct gatgtttggt caccgctga ttatgctgcc gatcttcggc    1140
gatcagggtc cgaacgcacg tctgattgaa gcgaaaaatg ccggcctgca agttgcgcgc    1200
```

```
aacgatggcg acggttcttt cgaccgtgag ggtgtggctg cggccattcg cgcagtggct    1260
gttgaagaag aatcatcgaa agtttttcag gcgaaagcca aaaaactgca agaaatcgtc    1320
gcggatatgg cctgccacga acgctacatt gatggtttca ttcagcaact gcgctcctac    1380
aaagactaa                                                             1389
```

<210> SEQ ID NO 3
<211> LENGTH: 462
<212> TYPE: PRT
<213> ORGANISM: Artificial Sequence
<220> FEATURE:
<223> OTHER INFORMATION: Synthetic Polypeptide

<400> SEQUENCE: 3

```
Met Gly Ser Ser Gly Met Ser Leu Ala Glu Arg Phe Ser Leu Thr Leu
1               5                   10                  15

Ser Arg Ser Ser Leu Val Val Gly Arg Ser Cys Val Glu Phe Glu Pro
            20                  25                  30

Glu Thr Val Pro Leu Leu Ser Thr Leu Arg Gly Lys Pro Ile Thr Phe
        35                  40                  45

Leu Gly Leu Met Pro Pro Leu His Glu Gly Arg Arg Glu Asp Gly Glu
    50                  55                  60

Asp Ala Thr Val Arg Trp Leu Asp Ala Gln Pro Ala Lys Ser Val Val
65                  70                  75                  80

Tyr Val Ala Leu Gly Ser Glu Val Pro Leu Gly Val Glu Lys Val His
                85                  90                  95

Glu Leu Ala Leu Gly Leu Glu Leu Ala Gly Thr Arg Phe Leu Trp Ala
            100                 105                 110

Leu Arg Lys Pro Thr Gly Val Ser Asp Ala Asp Leu Leu Pro Ala Gly
        115                 120                 125

Phe Glu Glu Arg Thr Arg Gly Arg Gly Val Val Ala Thr Arg Trp Val
    130                 135                 140

Pro Gln Met Ser Ile Leu Ala His Ala Ala Val Gly Ala Phe Leu Thr
145                 150                 155                 160

His Cys Gly Trp Asn Ser Thr Ile Glu Gly Leu Met Phe Gly His Pro
                165                 170                 175

Leu Ile Met Leu Pro Ile Phe Gly Asp Gln Gly Pro Asn Ala Arg Leu
            180                 185                 190

Ile Glu Ala Lys Asn Ala Gly Leu Gln Val Ala Arg Asn Asp Gly Asp
        195                 200                 205

Gly Ser Phe Asp Arg Glu Gly Val Ala Ala Ala Ile Arg Ala Val Ala
    210                 215                 220

Val Glu Glu Glu Ser Ser Lys Val Phe Gln Ala Lys Ala Lys Lys Leu
225                 230                 235                 240

Gln Glu Ile Val Ala Asp Met Ala Cys His Glu Arg Tyr Ile Asp Gly
                245                 250                 255

Phe Ile Gln Gln Leu Arg Ser Tyr Lys Asp Asp Ser Gly Tyr Ser Ser
            260                 265                 270

Ser Tyr Ala Ala Ala Ala Gly Met His Val Val Ile Cys Pro Trp Leu
        275                 280                 285

Ala Phe Gly His Leu Leu Pro Cys Leu Asp Leu Ala Gln Arg Leu Ala
    290                 295                 300

Ser Arg Gly His Arg Val Ser Phe Val Ser Thr Pro Arg Asn Ile Ser
305                 310                 315                 320
```

Arg Leu Pro Pro Val Arg Pro Ala Leu Ala Pro Leu Val Ala Phe Val
                325                 330                 335

Ala Leu Pro Leu Pro Arg Val Glu Gly Leu Pro Asp Gly Ala Glu Ser
        340                 345                 350

Thr Asn Asp Val Pro His Asp Arg Pro Asp Met Val Glu Leu His Arg
    355                 360                 365

Arg Ala Phe Asp Gly Leu Ala Ala Pro Phe Ser Glu Phe Leu Gly Thr
370                 375                 380

Ala Cys Ala Asp Trp Val Ile Val Asp Val Phe His His Trp Ala Ala
385                 390                 395                 400

Ala Ala Ala Leu Glu His Lys Val Pro Cys Ala Met Met Leu Leu Gly
                405                 410                 415

Ser Ala His Met Ile Ala Ser Ile Ala Asp Arg Arg Leu Glu Arg Ala
            420                 425                 430

Glu Thr Glu Ser Pro Ala Ala Ala Gly Gln Gly Arg Pro Ala Ala Ala
        435                 440                 445

Pro Thr Phe Glu Val Ala Arg Met Lys Leu Ile Arg Thr Lys
    450                 455                 460

<210> SEQ ID NO 4
<211> LENGTH: 1389
<212> TYPE: DNA
<213> ORGANISM: Artificial Sequence
<220> FEATURE:
<223> OTHER INFORMATION: Synthetic Polynucleotide

<400> SEQUENCE: 4

```
atgggtagct cgggcatgtc cctggcggaa cgcttttcgc tgacgctgag tcgctcatcc      60
ctggttgttg gtcgcagttg tgttgaattt gaaccggaaa ccgttccgct gctgtctacg     120
ctgcgcggca aaccgattac cttcctgggt ctgatgccgc cgctgcatga aggccgtcgc     180
gaagatggtg aagacgccac ggtgcgttgg ctggatgctc agccggcgaa atcggtggtt     240
tatgtcgcac tgggcagcga agtgccgctg ggtgtcgaaa agtgcacga actggccctg     300
ggcctggaac tggcaggcac ccgctttctg tgggcactgc gtaaaccgac gggcgttagc     360
gatgctgacc tgctgccggc gggtttcgaa gaacgcaccc gcggccgtgg tgtcgtggcc     420
acccgttggg tgccgcaaat gtccattctg gctcatgcgg ccgttggcgc atttctgacc     480
cactgcggtt ggaacagcac gatcgaaggc ctgatgtttg tcatccgct gattatgctg     540
ccgatcttcg gcgatcaggg tccgaacgca cgcctgatcg aagccaaaaa tgcaggcctg     600
caagttgcgc gtaacgatgg cgacggtagc tttaccgcg aaggtgtcgc agctgcgatt     660
cgtgctgtgg cggttgaaga agaaagcagc aaagtcttcc aggccaaagc gaaaaaactg     720
caagaaatcg tggctgatat ggcgtgtcat gaacgctata ttgacggctt tatccagcaa     780
ctgcgttctt acaaagatga cagtggctat agttcctcat cgccgcagc tgcgggtatg     840
catgttgtca tttgcccgtg gctggcgttt ggtcacctgc tgccgtgtct ggatctggca     900
cagcgcctgg catctcgcgg tcaccgtgtt tcgttcgtca gcaccccgcg caatatcagt     960
cgtctgccgc cggttcgtcc ggcgctggcg ccgctggttg cgttcgttgc actgccgctg    1020
ccgcgtgtgg aaggtctgcc ggatggtgcc gaatcgacca cgacgttcc gcatgatcgt    1080
ccggacatgg tcgaactgca tcgtcgcgcc tttgatggcc tggccgcacc gtttagcgaa    1140
tttctgggta cggcctgcgc agattggtc attgtggacg ttttcacca ctggcggcg    1200
gcggcggcgc tggaacataa agtgccgtgt gcgatgatgc tgctgggttc cgcccacatg    1260
```

-continued

```
attgcttcaa tcgcggatcg tcgcctggaa cgtgccgaaa ccgaaagtcc ggcggcggca    1320
ggccagggtc gtccggcggc ggcaccgacc tttgaagtgg cacgtatgaa actgattcgc    1380
acgaaataa                                                           1389
```

<210> SEQ ID NO 5
<211> LENGTH: 459
<212> TYPE: PRT
<213> ORGANISM: Hordeum vulgare

<400> SEQUENCE: 5

```
Met Asp Gly Asn Ser Ser Ser Pro Leu His Val Val Ile Cys Pro
1               5                   10                  15

Trp Leu Ala Leu Gly His Leu Leu Pro Cys Leu Asp Ile Ala Glu Arg
                20                  25                  30

Leu Ala Ser Arg Gly His Arg Val Ser Phe Val Ser Thr Pro Arg Asn
            35                  40                  45

Ile Ala Arg Leu Pro Pro Leu Arg Pro Ala Val Ala Pro Leu Val Asp
        50                  55                  60

Phe Val Ala Leu Pro Leu Pro His Val Asp Gly Leu Pro Glu Gly Ala
65                  70                  75                  80

Glu Ser Thr Asn Asp Val Pro Tyr Asp Lys Phe Glu Leu His Arg Lys
                85                  90                  95

Ala Phe Asp Gly Leu Ala Ala Pro Phe Ser Glu Phe Leu Arg Ala Ala
            100                 105                 110

Cys Ala Glu Gly Ala Gly Ser Arg Pro Asp Trp Leu Ile Val Asp Thr
        115                 120                 125

Phe His His Trp Ala Ala Ala Ala Val Glu Asn Lys Val Pro Cys
130                 135                 140

Val Met Leu Leu Leu Gly Ala Ala Thr Val Ile Ala Gly Phe Ala Arg
145                 150                 155                 160

Gly Val Ser Glu His Ala Ala Ala Val Gly Lys Glu Arg Pro Ala
                165                 170                 175

Ala Glu Ala Pro Ser Phe Glu Thr Glu Arg Arg Lys Leu Met Thr Thr
            180                 185                 190

Gln Asn Ala Ser Gly Met Thr Val Ala Glu Arg Tyr Phe Leu Thr Leu
        195                 200                 205

Met Arg Ser Asp Leu Val Ala Ile Arg Ser Cys Ala Glu Trp Glu Pro
210                 215                 220

Glu Ser Val Ala Ala Leu Thr Thr Leu Ala Gly Lys Pro Val Val Pro
225                 230                 235                 240

Leu Gly Leu Leu Pro Pro Ser Pro Glu Gly Gly Arg Gly Val Ser Lys
                245                 250                 255

Glu Asp Ala Ala Val Arg Trp Leu Asp Ala Gln Pro Ala Lys Ser Val
            260                 265                 270

Val Tyr Val Ala Leu Gly Ser Glu Val Pro Leu Arg Ala Glu Gln Val
        275                 280                 285

His Glu Leu Ala Leu Gly Leu Glu Leu Ser Gly Ala Arg Phe Leu Trp
290                 295                 300

Ala Leu Arg Lys Pro Thr Asp Ala Pro Asp Ala Ala Val Leu Pro Pro
305                 310                 315                 320

Gly Phe Glu Glu Arg Thr Arg Gly Arg Gly Leu Val Val Thr Gly Trp
                325                 330                 335

Val Pro Gln Ile Gly Val Leu Ala His Gly Ala Val Ala Ala Phe Leu
            340                 345                 350
```

Thr His Cys Gly Trp Asn Ser Thr Ile Glu Gly Leu Leu Phe Gly His
            355                 360                 365

Pro Leu Ile Met Leu Pro Ile Ser Ser Asp Gln Gly Pro Asn Ala Arg
    370                 375                 380

Leu Met Glu Gly Arg Lys Val Gly Met Gln Val Pro Arg Asp Glu Ser
385                 390                 395                 400

Asp Gly Ser Phe Arg Arg Glu Asp Val Ala Ala Thr Val Arg Ala Val
                405                 410                 415

Ala Val Glu Glu Asp Gly Arg Arg Val Phe Thr Ala Asn Ala Lys Lys
            420                 425                 430

Met Gln Glu Ile Val Ala Asp Gly Ala Cys His Glu Arg Cys Ile Asp
            435                 440                 445

Gly Phe Ile Gln Gln Leu Arg Ser Tyr Lys Ala
        450                 455

<210> SEQ ID NO 6
<211> LENGTH: 1380
<212> TYPE: DNA
<213> ORGANISM: Hordeum vulgare

<400> SEQUENCE: 6
atggatggta actcctcctc ctcgccgctg catgtggtca tttgtccgtg gctggctctg        60
ggtcacctgc tgccgtgtct ggatattgct gaacgtctgg cgtcacgcgg ccatcgtgtc       120
agttttgtgt ccaccccgcg caacattgcc cgtctgccgc cgctgcgtcc ggctgttgca       180
ccgctggttg atttcgtcgc actgccgctg ccgcatgttg acggtctgcc ggagggtgcg       240
gaatcgacca tgatgtgccg tatgacaaa tttgaactgc accgtaaggc gttcgatggt        300
ctggcggccc cgtttagcga atttctgcgt gcagcttgcg cagaaggtgc aggttctcgc       360
ccggattggc tgattgtgga cacctttcat cactgggcgg cggcggcggc ggtggaaaac       420
aaagtgccgt gtgttatgct gctgctgggt gcagcaacgg tgatcgctgg tttcgcgcgt       480
ggtgttagcg aacatgcggc ggcggcggtg ggtaaagaac gtccggctgc ggaagccccg       540
agttttgaaa ccgaacgtcg caagctgatg accacgcaga atgcctccgg catgaccgtg       600
gcagaacgct atttcctgac gctgatgcgt agcgatctgg ttgccatccg ctcttgcgca       660
gaatgggaac cggaaagcgt ggcagcactg accacgctgg caggtaaacc ggtggttccg       720
ctgggtctgc tgccgccgag tccggaaggc ggtcgtggcg tttccaaaga agatgctgcg       780
gtccgttggc tggacgcaca gccggcaaag tcagtcgtgt acgtcgcact gggttcggaa       840
gtgccgctgc gtgcggaaca agttcacgaa ctggcactgg gcctggaact gagcggtgct       900
cgctttctgt gggcgctgcg taaaccgacc gatgcaccgg acgccgcagt gctgccgccg       960
ggtttcgaag aacgtacccg cggccgtggt ctggttgtca cgggttgggt gccgcagatt      1020
ggcgttctgg ctcatggtgc ggtggctgcg tttctgaccc actgtggctg gaactctacg      1080
atcgaaggcc tgctgttcgg tcatccgctg attatgctgc cgatcagctc tgatcagggt      1140
ccgaatgcgc gcctgatgga aggccgtaaa gtcggtatgc aagtgccgcg tgatgaatca      1200
gacggctcgt tcgtcgcga agatgttgcc gcaaccgtcc gcgccgtggc agttgaagaa      1260
gacggtcgtc gcgtcttcac ggctaacgcg aaaaagatgc aagaaattgt ggccgatggc      1320
gcatgccacg aacgttgtat tgacggtttt atccagcaac tgcgcagtta caaggcgtaa      1380

<210> SEQ ID NO 7
<211> LENGTH: 458

<212> TYPE: PRT
<213> ORGANISM: Stevia rebaudiana

<400> SEQUENCE: 7

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
370                 375                 380

Ala Arg Tyr Met Ser Asp Val Leu Lys Val Gly Val Tyr Leu Glu Asn
385                 390                 395                 400
```

Gly Trp Glu Arg Gly Glu Ile Ala Asn Ala Ile Arg Arg Val Met Val
            405                 410                 415

Asp Glu Glu Gly Glu Tyr Ile Arg Gln Asn Ala Arg Val Leu Lys Gln
        420                 425                 430

Lys Ala Asp Val Ser Leu Met Lys Gly Gly Ser Ser Tyr Glu Ser Leu
    435                 440                 445

Glu Ser Leu Val Ser Tyr Ile Ser Ser Leu
450                 455

<210> SEQ ID NO 8
<211> LENGTH: 1377
<212> TYPE: DNA
<213> ORGANISM: Stevia rebaudiana

<400> SEQUENCE: 8

```
atggagaata agacagaaac aaccgtaaga cggaggcgga ggattatctt gttccctgta      60
ccatttcagg gccatattaa tccgatcctc caattagcaa acgtcctcta ctccaaggga     120
ttttcaataa caatcttcca tactaacttt aacaagccta aaacgagtaa ttatcctcac     180
tttacattca ggttcattct agacaacgac cctcaggatg agcgtatctc aaatttacct     240
acgcatggcc ccttggcagg tatgcgaata ccaataatca atgagcatgg agccgatgaa     300
ctccgtcgcg agttagagct tctcatgctc gcaagtgagg aagacgagga agtttcgtgc     360
ctaataactg atgcgctttg gtacttcgcc caatcagtcg cagactcact gaatctacgc     420
cgtttggtcc ttatgacaag ttcattattc aactttcacg cacatgtatc actgccgcaa     480
tttgacgagt tgggttacct ggacccggat gacaaaacgc gattggagga caagcgtcg      540 ggcttcccca tgctgaaagt caaagatatt aagagcgctt atagtaattg gcaaattctg     600
aaagaaattc tcggaaaaat gataaagcaa accaaagcgt cctctggagt aatctggaac     660
tccttcaagg agttagagga atctgaactt gaaacggtca tcagagaaat ccccgctccc     720
tcgttcttaa ttccactacc caagcacctt actgcaagta gcagttccct cctagatcat     780
gaccgaaccg tgtttcagtg gctggatcag caacccccgt cgtcagttct atatgtaagc     840
tttgggagta cttcggaagt ggatgaaaag gacttcttag agattgcgcg agggctcgtg     900
gatagcaaac agagcttcct gtgggtagtg agaccgggat tcgttaaggg ctcgacgtgg     960
gtcgagccgt tgccagatgg ttttctaggg gagagaggga gaatcgtgaa atgggttcca    1020
cagcaagagg ttttggctca cggagctata ggggcctttt ggacccactc tggttggaat    1080
tctactcttg aaagtgtctg tgaaggcgtt ccaatgatat tttctgattt tgggcttgac    1140
cagcctctaa acgctcgcta tatgtctgat gtgttgaagg ttggcgtgta cctggagaat    1200
ggttgggaaa ggggggaaat tgccaacgcc atacgccggg taatggtgga cgaggaaggt    1260
gagtacatac gtcagaacgc tcgggtttta aaacaaaaag cggacgtcag ccttatgaag    1320
ggaggtagct cctatgaatc cctagaatcc ttggtaagct atatatcttc gttataa       1377
```

<210> SEQ ID NO 9
<211> LENGTH: 473
<212> TYPE: PRT
<213> ORGANISM: Artificial Sequence
<220> FEATURE:
<223> OTHER INFORMATION: Synthetic Polypeptide

<400> SEQUENCE: 9

Met Ala Thr Ser Asp Ser Ile Val Asp Asp Arg Lys Gln Leu His Val
1               5                   10                  15

```
Ala Thr Phe Pro Trp Leu Ala Phe Gly His Ile Leu Pro Tyr Leu Gln
             20                  25                  30

Leu Ser Lys Leu Ile Ala Glu Lys Gly His Lys Val Ser Phe Leu Ser
         35                  40                  45

Thr Thr Arg Asn Ile Gln Arg Leu Ser Ser His Ile Ser Pro Leu Ile
     50                  55                  60

Asn Val Gln Leu Thr Leu Pro Arg Val Gln Glu Leu Pro Glu Asp
 65                  70                  75                  80

Ala Glu Ala Thr Thr Asp Val His Pro Glu Asp Ile Pro Tyr Leu Lys
                 85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
            115                 120                 125

Ser Ile Ala Ala Ser Leu Gly Ile Ser Arg Ala His Phe Ser Val Thr
130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Met Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Ala Leu Val
        275                 280                 285

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Arg Ser Leu Arg Ser Val Val Val Glu Lys Glu Gly Glu Ile Tyr
            420                 425                 430
```

```
Lys Ala Asn Ala Arg Glu Leu Ser Lys Ile Tyr Asn Asp Thr Lys Val
            435                 440                 445

Glu Lys Glu Tyr Val Ser Gln Phe Val Asp Tyr Leu Glu Lys Asn Ala
        450                 455                 460

Arg Ala Val Ala Ile Asp His Glu Ser
465                 470

<210> SEQ ID NO 10
<211> LENGTH: 1422
<212> TYPE: DNA
<213> ORGANISM: Artificial Sequence
<220> FEATURE:
<223> OTHER INFORMATION: Synthetic Polynucleotide

<400> SEQUENCE: 10
atggctacca gtgactccat agttgacgac cgtaagcagc ttcatgttgc gacgttccca        60
tggcttgctt tcggtcacat cctcccttac cttcagcttt cgaaattgat agctgaaaag       120
ggtcacaaag tctcgtttct ttctaccacc agaaacattc aacgtctctc ttctcatatc       180
tcgccactca taaatgttgt tcaactcaca cttccacgtg tccaagagct gccggaggat       240
gcagaggcga ccactgacgt ccaccctgaa gatattccat atctcaagaa ggcttctgat       300
ggtcttcaac cggaggtcac ccggtttcta gaacaacact ctccggactg gattatttat       360
gattatactc actactggtt gccatccatc gcggctagcc tcggtatctc acgagcccac       420
ttctccgtca ccactccatg ggccattgct tatatgggac cctcagctga cgccatgata       480
aatggttcag atggtcgaac cacgttgag atctcacga ccgcccaa gtggtttccc          540
tttccgacca agtatgctg gcggaagcat gatcttgccc gactggtgcc ttacaaagct       600
ccggggatat ctgatggata ccgtatgggg atggttctta agggatctga ttgtttgctt       660
tccaaatgtt accatgagtt tggaactcaa tggctacctc ttttggagac actacaccaa       720
gtaccggtgg ttccggtggg attactgcca ccggaaatac ccggagacga gaaagatgaa       780
acatgggtgt caatcaagaa atggctcgat ggtaaacaaa aaggcagtgt ggtgtacgtt       840
gcattaggaa gcgaggcttt ggtgagccaa accgaggttg ttgagttagc attgggtctc       900
gagctttctg ggttgccatt tgtttgggct tatagaaaac caaaaggtcc cgcgaagtca       960
gactcggtgg agttgccaga cgggttcgtg gaacgaactc gtgaccgtgg gttggtctgg      1020
acgagttggg cacctcagtt acgaatactg agccatgagt cggtttgtgg tttcttgact      1080
cattgtggtt ctggatcaat gtggaaggg ctaatgtttg gtcaccctct aatcatgcta       1140
ccgattttg gggaccaacc tctgaatgct cgattactgg aggacaaaca ggtgggaatc       1200
gagataccaa gaaatgagga agatggttgc ttgaccaagg agtcggttgc tagatcactg      1260
aggtccgttg ttgtggaaaa agaagggag atctacaagg cgaacgcgag ggagctgagt       1320
aaaatctata cgacactaa ggttgaaaaa gaatatgtaa gccaattcgt agactatttg      1380
gaaaagaatg cgcgtgcggt tgccatcgat catgagagtt aa                        1422

<210> SEQ ID NO 11
<211> LENGTH: 458
<212> TYPE: PRT
<213> ORGANISM: Artificial Sequence
<220> FEATURE:
<223> OTHER INFORMATION: Synthetic Polypeptide

<400> SEQUENCE: 11

Met Asn Trp Gln Ile Leu Lys Glu Ile Leu Gly Lys Met Ile Lys Gln
1               5                   10                  15
```

```
Thr Lys Ala Ser Ser Gly Val Ile Trp Asn Ser Phe Lys Glu Leu Glu
         20                  25                  30

Glu Ser Glu Leu Glu Thr Val Ile Arg Glu Ile Pro Ala Pro Ser Phe
         35                  40                  45

Leu Ile Pro Leu Pro Lys His Leu Thr Ala Ser Ser Ser Leu Leu
 50                  55                  60

Asp His Asp Arg Thr Val Phe Gln Trp Leu Asp Gln Pro Pro Ser
 65                  70                  75                  80

Ser Val Leu Tyr Val Ser Phe Gly Ser Thr Ser Glu Val Asp Glu Lys
             85                  90                  95

Asp Phe Leu Glu Ile Ala Arg Gly Leu Val Asp Ser Lys Gln Ser Phe
         100                 105                 110

Leu Trp Val Val Arg Pro Gly Phe Val Lys Gly Ser Thr Trp Val Glu
         115                 120                 125

Pro Leu Pro Asp Gly Phe Leu Gly Glu Arg Gly Arg Ile Val Lys Trp
 130                 135                 140

Val Pro Gln Gln Glu Val Leu Ala His Gly Ala Ile Gly Ala Phe Trp
 145                 150                 155                 160

Thr His Ser Gly Trp Asn Ser Thr Leu Glu Ser Val Cys Glu Gly Val
             165                 170                 175

Pro Met Ile Phe Ser Asp Phe Gly Leu Asp Gln Pro Leu Asn Ala Arg
         180                 185                 190

Tyr Met Ser Asp Val Leu Lys Val Gly Val Tyr Leu Glu Asn Gly Trp
         195                 200                 205

Glu Arg Gly Glu Ile Ala Asn Ala Ile Arg Arg Val Met Val Asp Glu
 210                 215                 220

Glu Gly Glu Tyr Ile Arg Gln Asn Ala Arg Val Leu Lys Gln Lys Ala
 225                 230                 235                 240

Asp Val Ser Leu Met Lys Gly Gly Ser Ser Tyr Glu Ser Leu Glu Ser
             245                 250                 255

Leu Val Ser Tyr Ile Ser Ser Leu Glu Asn Lys Thr Glu Thr Thr Val
             260                 265                 270

Arg Arg Arg Arg Ile Ile Leu Phe Pro Val Pro Phe Gln Gly His
         275                 280                 285

Ile Asn Pro Ile Leu Gln Leu Ala Asn Val Leu Tyr Ser Lys Gly Phe
         290                 295                 300

Ser Ile Thr Ile Phe His Thr Asn Phe Asn Lys Pro Lys Thr Ser Asn
 305                 310                 315                 320

Tyr Pro His Phe Thr Phe Arg Phe Ile Leu Asp Asn Asp Pro Gln Asp
                 325                 330                 335

Glu Arg Ile Ser Asn Leu Pro Thr His Gly Pro Leu Ala Gly Met Arg
             340                 345                 350

Ile Pro Ile Ile Asn Glu His Gly Ala Asp Glu Leu Arg Arg Glu Leu
         355                 360                 365

Glu Leu Leu Met Leu Ala Ser Glu Glu Asp Glu Val Ser Cys Leu
         370                 375                 380

Ile Thr Asp Ala Leu Trp Tyr Phe Ala Gln Ser Val Ala Asp Ser Leu
 385                 390                 395                 400

Asn Leu Arg Arg Leu Val Leu Met Thr Ser Ser Leu Phe Asn Phe His
             405                 410                 415

Ala His Val Ser Leu Pro Gln Phe Asp Glu Leu Gly Tyr Leu Asp Pro
             420                 425                 430
```

Asp Asp Lys Thr Arg Leu Glu Glu Gln Ala Ser Gly Phe Pro Met Leu
        435                 440                 445

Lys Val Lys Asp Ile Lys Ser Ala Tyr Ser
        450                 455

<210> SEQ ID NO 12
<211> LENGTH: 1377
<212> TYPE: DNA
<213> ORGANISM: Artificial Sequence
<220> FEATURE:
<223> OTHER INFORMATION: Synthetic Polynucleotide

<400> SEQUENCE: 12

| | | | | | |
|---|---|---|---|---|---|
| atgaactggc | aaatcctgaa | agaaatcctg | ggtaaaatga | tcaaacaaac | caaagcgtcg | 60 |
| tcgggcgtta | tctggaactc | cttcaaagaa | ctggaagaat | cagaactgga | aaccgttatt | 120 |
| cgcgaaatcc | cggctccgtc | gttcctgatt | ccgctgccga | acatctgac | cgcgagcagc | 180 |
| agcagcctgc | tggatcacga | ccgtacggtc | tttcagtggc | tggatcagca | accgccgtca | 240 |
| tcggtgctgt | atgtttcatt | cggtagcacc | tctgaagtcg | atgaaaaaga | ctttctggaa | 300 |
| atcgctcgcg | gcctggtgga | tagtaaacag | tccttcctgt | gggtggttcg | tccgggtttt | 360 |
| gtgaaaggca | gcacgtgggt | tgaaccgctg | ccggatggct | tcctgggtga | acgcggccgt | 420 |
| attgtcaaat | gggtgccgca | gcaagaagtg | ctggcacatg | gtgctatcgg | cgcgttttgg | 480 |
| acccactctg | gttggaacag | tacgctggaa | tccgtttgcg | aaggtgtccc | gatgattttc | 540 |
| agcgattttg | gcctggacca | gccgctgaat | gcccgctata | tgtctgatgt | tctgaaagtc | 600 |
| ggtgtgtacc | tggaaaacgg | ttgggaacgt | ggcgaaattg | cgaatgccat | ccgtcgcgtt | 660 |
| atggtcgatg | aagaaggcga | atacattcgc | cagaacgctc | gtgtcctgaa | caaaaagcg | 720 |
| gacgtgagcc | tgatgaaagg | cggtagctct | tatgaatcac | tggaatcgct | ggttagctac | 780 |
| atcagttccc | tggaaaataa | aaccgaaacc | acggtgcgtc | gccgtcgccg | tattatcctg | 840 |
| ttcccggttc | cgtttcaggg | tcatattaac | ccgatcctgc | aactggcgaa | tgttctgtat | 900 |
| tcaaaaggct | tttcgatcac | catcttccat | acgaacttca | caaaccgaa | accagtaac | 960 |
| tacccgcact | ttacgttccg | ctttattctg | gataacgacc | gcaggatga | acgtatctcc | 1020 |
| aatctgccga | cccacggccc | gctggccggt | atgcgcattc | cgattatcaa | tgaacacggt | 1080 |
| gcagatgaac | tgcgccgtga | actggaactg | ctgatgctgg | ccagtgaaga | agatgaagaa | 1140 |
| gtgtcctgtc | tgatcaccga | cgcactgtgg | tatttcgccc | agagcgttgc | agattctctg | 1200 |
| aacctgcgcc | gtctggtcct | gatgacgtca | tcgctgttca | attttcatgc | gcacgttct | 1260 |
| ctgccgcaat | tgatgaact | gggctacctg | gacccggatg | acaaaacccg | tctggaagaa | 1320 |
| caagccagtg | gttttccgat | gctgaaagtc | aaagacatta | aatccgccta | ttcgtaa | 1377 |

<210> SEQ ID NO 13
<211> LENGTH: 475
<212> TYPE: PRT
<213> ORGANISM: Artificial Sequence
<220> FEATURE:
<223> OTHER INFORMATION: Synthetic Polypeptide

<400> SEQUENCE: 13

Met Asn Trp Gln Ile Leu Lys Glu Ile Leu Gly Lys Met Ile Lys Gln
1               5                   10                  15

Thr Lys Ala Ser Ser Gly Val Ile Trp Asn Ser Phe Lys Glu Leu Glu
        20                  25                  30

Glu Ser Glu Leu Glu Thr Val Ile Arg Glu Ile Pro Ala Pro Ser Phe

```
                  35                  40                  45
Leu Ile Pro Leu Pro Lys His Leu Thr Ala Ser Ser Ser Leu Leu
             50                  55                  60

Asp His Asp Arg Thr Val Phe Gln Trp Leu Asp Gln Pro Pro Ser
 65                  70                  75                  80

Ser Val Leu Tyr Val Ser Phe Gly Ser Thr Ser Glu Val Asp Glu Lys
                 85                  90                  95

Asp Phe Leu Glu Ile Ala Arg Gly Leu Val Asp Ser Lys Gln Ser Phe
                100                 105                 110

Leu Trp Val Val Arg Pro Gly Phe Val Lys Gly Ser Thr Trp Val Glu
                115                 120                 125

Pro Leu Pro Asp Gly Phe Leu Gly Glu Arg Gly Arg Ile Val Lys Trp
                130                 135                 140

Val Pro Gln Gln Glu Val Leu Ala His Gly Ala Ile Gly Ala Phe Trp
145                 150                 155                 160

Thr His Ser Gly Trp Asn Ser Thr Leu Glu Ser Val Cys Glu Gly Val
                165                 170                 175

Pro Met Ile Phe Ser Asp Phe Gly Leu Asp Gln Pro Leu Asn Ala Arg
                180                 185                 190

Tyr Met Ser Asp Val Leu Lys Val Gly Val Tyr Leu Glu Asn Gly Trp
                195                 200                 205

Glu Arg Gly Glu Ile Ala Asn Ala Ile Arg Arg Val Met Val Asp Glu
                210                 215                 220

Glu Gly Glu Tyr Ile Arg Gln Asn Ala Arg Val Leu Lys Gln Lys Ala
225                 230                 235                 240

Asp Val Ser Leu Met Lys Gly Gly Ser Ser Tyr Glu Ser Leu Glu Ser
                245                 250                 255

Leu Val Ser Tyr Ile Ser Ser Leu Tyr Lys Asp Asp Ser Gly Tyr Ser
                260                 265                 270

Ser Ser Tyr Ala Ala Ala Ala Gly Met Glu Asn Lys Thr Glu Thr Thr
                275                 280                 285

Val Arg Arg Arg Arg Ile Ile Leu Phe Pro Val Pro Phe Gln Gly
290                 295                 300

His Ile Asn Pro Ile Leu Gln Leu Ala Asn Val Leu Tyr Ser Lys Gly
305                 310                 315                 320

Phe Ser Ile Thr Ile Phe His Thr Asn Phe Asn Lys Pro Lys Thr Ser
                325                 330                 335

Asn Tyr Pro His Phe Thr Phe Arg Phe Ile Leu Asp Asn Asp Pro Gln
                340                 345                 350

Asp Glu Arg Ile Ser Asn Leu Pro Thr His Gly Pro Leu Ala Gly Met
                355                 360                 365

Arg Ile Pro Ile Ile Asn Glu His Gly Ala Asp Glu Leu Arg Arg Glu
                370                 375                 380

Leu Glu Leu Leu Met Leu Ala Ser Glu Glu Asp Glu Glu Val Ser Cys
385                 390                 395                 400

Leu Ile Thr Asp Ala Leu Trp Tyr Phe Ala Gln Ser Val Ala Asp Ser
                405                 410                 415

Leu Asn Leu Arg Arg Leu Val Leu Met Thr Ser Ser Leu Phe Asn Phe
                420                 425                 430

His Ala His Val Ser Leu Pro Gln Phe Asp Glu Leu Gly Tyr Leu Asp
                435                 440                 445

Pro Asp Asp Lys Thr Arg Leu Glu Glu Gln Ala Ser Gly Phe Pro Met
450                 455                 460
```

Leu Lys Val Lys Asp Ile Lys Ser Ala Tyr Ser
465                 470                 475

<210> SEQ ID NO 14
<211> LENGTH: 1428
<212> TYPE: DNA
<213> ORGANISM: Artificial Sequence
<220> FEATURE:
<223> OTHER INFORMATION: Synthetic Polynucleotide

<400> SEQUENCE: 14

```
atgaactggc aaatcctgaa agaaatcctg ggtaaaatga tcaaacaaac caaagcgtcg      60
tcgggcgtta tctggaactc cttcaaagaa ctggaagaat cagaactgga aaccgttatt     120
cgcgaaatcc cggctccgtc gttcctgatt ccgctgccga acatctgac cgcgagcagc     180
agcagcctgc tggatcacga ccgtacggtc tttcagtggc tggatcagca accgccgtca     240
tcggtgctgt atgtttcatt cggtagcacc tctgaagtcg atgaaaaaga ctttctggaa     300
atcgctcgcg gcctggtgga tagtaaacag tccttcctgt gggtggttcg tccgggtttt     360
gtgaaaggca gcacgtgggt tgaaccgctg ccggatggct tcctgggtga acgcggccgt     420
attgtcaaat gggtgccgca gcaagaagtg ctggcacatg gtgctatcgg cgcgttttgg     480
acccactctg gttggaacag tacgctggaa tccgtttgcg aaggtgtccc gatgattttc     540
agcgattttg cctggaccac cgcgctgaat gcccgctata tgtctgatgt tctgaaagtc     600
ggtgtgtacc tggaaaacgg ttgggaacgt ggcgaaattg cgaatgccat ccgtcgcgtt     660
atggtcgatg aagaaggcga atacattcgc cagaacgctc gtgtcctgaa acaaaaagcg     720
gacgtgagcc tgatgaaagg cggtagctct tatgaatcac tggaatcgct ggttagctac     780
atcagttccc tgtacaaaga tgacagcggt tatagcagca gctatgcggc ggcggcgggt     840
atggaaaata aaaccgaaac cacggtgcgt cgccgtcgcc gtattatcct gttcccggtt     900
ccgtttcagg gtcatattaa cccgatcctg caactggcga atgttctgta ttcaaaaggc     960
ttttcgatca ccatcttcca tacgaacttc aacaaaccga aaccagtaa ctacccgcac    1020
tttacgttcc gctttattct ggataacgac ccgcaggatg aacgtatctc caatctgccg    1080
acccacggcc cgctggccgg tatgcgcatt ccgattatca tgaacacgg tgcagatgaa    1140
ctgcgccgtg aactggaact gctgatgctg gccagtgaag aagatgaaga agtgtcctgt    1200
ctgatcaccg acgcactgtg gtatttcgcc cagagcgttg cagattctct gaacctgcgc    1260
cgtctggtcc tgatgacgtc atcgctgttc aattttcatg cgcacgtttc tctgccgcaa    1320
tttgatgaac tgggctacct ggacccggat gacaaaaccc gtctggaaga caagccagt    1380
ggttttccga tgctgaaagt caaagacatt aaatccgcct attcgtaa                1428
```

<210> SEQ ID NO 15
<211> LENGTH: 1268
<212> TYPE: PRT
<213> ORGANISM: Artificial Sequence
<220> FEATURE:
<223> OTHER INFORMATION: Synthetic Polypeptide

<400> SEQUENCE: 15

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr

```
                35                  40                  45
Asn Phe Asn Lys Pro Lys Thr Ser Asn Tyr Pro His Phe Thr Phe Arg
 50                  55                  60

Phe Ile Leu Asp Asn Asp Pro Gln Asp Glu Arg Ile Ser Asn Leu Pro
65                   70                  75                  80

Thr His Gly Pro Leu Ala Gly Met Arg Ile Pro Ile Ile Asn Glu His
                 85                  90                  95

Gly Ala Asp Glu Leu Arg Arg Glu Leu Glu Leu Leu Met Leu Ala Ser
                100                 105                 110

Glu Glu Asp Glu Glu Val Ser Cys Leu Ile Thr Asp Ala Leu Trp Tyr
            115                 120                 125

Phe Ala Gln Ser Val Ala Asp Ser Leu Asn Leu Arg Arg Leu Val Leu
        130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
                180                 185                 190

Ala Tyr Ser Asn Trp Gln Ile Leu Lys Glu Ile Leu Gly Lys Met Ile
            195                 200                 205

Lys Gln Thr Lys Ala Ser Ser Gly Val Ile Trp Asn Ser Phe Lys Glu
        210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
                260                 265                 270

Pro Ser Ser Val Leu Tyr Val Ser Phe Gly Ser Thr Ser Glu Val Asp
            275                 280                 285

Glu Lys Asp Phe Leu Glu Ile Ala Arg Gly Leu Val Asp Ser Lys Gln
        290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
                340                 345                 350

Phe Trp Thr His Ser Gly Trp Asn Ser Thr Leu Glu Ser Val Cys Glu
            355                 360                 365

Gly Val Pro Met Ile Phe Ser Asp Phe Gly Leu Asp Gln Pro Leu Asn
        370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
                420                 425                 430

Lys Ala Asp Val Ser Leu Met Lys Gly Gly Ser Ser Tyr Glu Ser Leu
            435                 440                 445

Glu Ser Leu Val Ser Tyr Ile Ser Ser Leu Gly Ser Gly Ala Asn Ala
        450                 455                 460
```

Glu Arg Met Ile Thr Arg Val His Ser Gln Arg Glu Arg Leu Asn Glu
465                 470                 475                 480

Thr Leu Val Ser Glu Arg Asn Glu Val Leu Ala Leu Leu Ser Arg Val
            485                 490                 495

Glu Ala Lys Gly Lys Gly Ile Leu Gln Gln Asn Gln Ile Ile Ala Glu
            500                 505                 510

Phe Glu Ala Leu Pro Glu Gln Thr Arg Lys Lys Leu Glu Gly Gly Pro
            515                 520                 525

Phe Phe Asp Leu Leu Lys Ser Thr Gln Glu Ala Ile Val Leu Pro Pro
            530                 535                 540

Trp Val Ala Leu Ala Val Arg Pro Arg Pro Gly Val Trp Glu Tyr Leu
545                 550                 555                 560

Arg Val Asn Leu His Ala Leu Val Val Glu Glu Leu Gln Pro Ala Glu
            565                 570                 575

Phe Leu His Phe Lys Glu Glu Leu Val Asp Gly Val Lys Asn Gly Asn
            580                 585                 590

Phe Thr Leu Glu Leu Asp Phe Glu Pro Phe Asn Ala Ser Ile Pro Arg
            595                 600                 605

Pro Thr Leu His Lys Tyr Ile Gly Asn Gly Val Asp Phe Leu Asn Arg
610                 615                 620

His Leu Ser Ala Lys Leu Phe His Asp Lys Glu Ser Leu Leu Pro Leu
625                 630                 635                 640

Leu Lys Phe Leu Arg Leu His Ser His Gln Gly Lys Asn Leu Met Leu
            645                 650                 655

Ser Glu Lys Ile Gln Asn Leu Asn Thr Leu Gln His Thr Leu Arg Lys
            660                 665                 670

Ala Glu Glu Tyr Leu Ala Glu Leu Lys Ser Glu Thr Leu Tyr Glu Glu
            675                 680                 685

Phe Glu Ala Lys Phe Glu Glu Ile Gly Leu Glu Arg Gly Trp Gly Asp
            690                 695                 700

Asn Ala Glu Arg Val Leu Asp Met Ile Arg Leu Leu Leu Asp Leu Leu
705                 710                 715                 720

Glu Ala Pro Asp Pro Cys Thr Leu Glu Thr Phe Leu Gly Arg Val Pro
            725                 730                 735

Met Val Phe Asn Val Val Ile Leu Ser Pro His Gly Tyr Phe Ala Gln
            740                 745                 750

Asp Asn Val Leu Gly Tyr Pro Asp Thr Gly Gly Gln Val Val Tyr Ile
            755                 760                 765

Leu Asp Gln Val Arg Ala Leu Glu Ile Glu Met Leu Gln Arg Ile Lys
            770                 775                 780

Gln Gln Gly Leu Asn Ile Lys Pro Arg Ile Leu Ile Leu Thr Arg Leu
785                 790                 795                 800

Leu Pro Asp Ala Val Gly Thr Thr Cys Gly Glu Arg Leu Glu Arg Val
            805                 810                 815

Tyr Asp Ser Glu Tyr Cys Asp Ile Leu Arg Val Pro Phe Arg Thr Glu
            820                 825                 830

Lys Gly Ile Val Arg Lys Trp Ile Ser Arg Phe Glu Val Trp Pro Tyr
            835                 840                 845

Leu Glu Thr Tyr Thr Glu Asp Ala Ala Val Glu Leu Ser Lys Glu Leu
            850                 855                 860

Asn Gly Lys Pro Asp Leu Ile Ile Gly Asn Tyr Ser Asp Gly Asn Leu
865                 870                 875                 880

-continued

```
Val Ala Ser Leu Leu Ala His Lys Leu Gly Val Thr Gln Cys Thr Ile
                885                 890                 895
Ala His Ala Leu Glu Lys Thr Lys Tyr Pro Asp Ser Asp Ile Tyr Trp
            900                 905                 910
Lys Lys Leu Asp Asp Lys Tyr His Phe Ser Cys Gln Phe Thr Ala Asp
        915                 920                 925
Ile Phe Ala Met Asn His Thr Asp Phe Ile Ile Thr Ser Thr Phe Gln
    930                 935                 940
Glu Ile Ala Gly Ser Lys Glu Thr Val Gly Gln Tyr Glu Ser His Thr
945                 950                 955                 960
Ala Phe Thr Leu Pro Gly Leu Tyr Arg Val Val His Gly Ile Asp Val
                965                 970                 975
Phe Asp Pro Lys Phe Asn Ile Val Ser Pro Gly Ala Asp Met Ser Ile
            980                 985                 990
Tyr Phe Pro Tyr Thr Glu Glu Lys Arg Arg Leu Thr Lys Phe His Ser
        995                 1000                1005
Glu Ile Glu Glu Leu Leu Tyr Ser Asp Val Glu Asn Lys Glu His
    1010                1015                1020
Leu Cys Val Leu Lys Asp Lys Lys Pro Ile Leu Phe Thr Met
    1025                1030                1035
Ala Arg Leu Asp Arg Val Lys Asn Leu Ser Gly Leu Val Glu Trp
    1040                1045                1050
Tyr Gly Lys Asn Thr Arg Leu Arg Glu Leu Ala Asn Leu Val Val
    1055                1060                1065
Val Gly Gly Asp Arg Arg Lys Glu Ser Lys Asp Asn Glu Glu Lys
    1070                1075                1080
Ala Glu Met Lys Lys Met Tyr Asp Leu Ile Glu Glu Tyr Lys Leu
    1085                1090                1095
Asn Gly Gln Phe Arg Trp Ile Ser Ser Gln Met Asp Arg Val Arg
    1100                1105                1110
Asn Gly Glu Leu Tyr Arg Tyr Ile Cys Asp Thr Lys Gly Ala Phe
    1115                1120                1125
Val Gln Pro Ala Leu Tyr Glu Ala Phe Gly Leu Thr Val Val Glu
    1130                1135                1140
Ala Met Thr Cys Gly Leu Pro Thr Phe Ala Thr Cys Lys Gly Gly
    1145                1150                1155
Pro Ala Glu Ile Ile Val His Gly Lys Ser Gly Phe His Ile Asp
    1160                1165                1170
Pro Tyr His Gly Asp Gln Ala Ala Asp Thr Leu Ala Asp Phe Phe
    1175                1180                1185
Thr Lys Cys Lys Glu Asp Pro Ser His Trp Asp Glu Ile Ser Lys
    1190                1195                1200
Gly Gly Leu Gln Arg Ile Glu Glu Lys Tyr Thr Trp Gln Ile Tyr
    1205                1210                1215
Ser Gln Arg Leu Leu Thr Leu Thr Gly Val Tyr Gly Phe Trp Lys
    1220                1225                1230
His Val Ser Asn Leu Asp Arg Leu Glu Ala Arg Tyr Leu Glu
    1235                1240                1245
Met Phe Tyr Ala Leu Lys Tyr Arg Pro Leu Ala Gln Ala Val Pro
    1250                1255                1260
Leu Ala Gln Asp Asp
    1265
```

<210> SEQ ID NO 16
<211> LENGTH: 3807
<212> TYPE: DNA
<213> ORGANISM: Artificial Sequence
<220> FEATURE:
<223> OTHER INFORMATION: Synthetic Polynucleotide

<400> SEQUENCE: 16

| | |
|---|---:|
| atggagaata agacagaaac aaccgtaaga cggaggcgga ggattatctt gttccctgta | 60 |
| ccatttcagg gccatattaa tccgatcctc caattagcaa acgtcctcta ctccaaggga | 120 |
| ttttcaataa caatcttcca tactaacttt aacaagccta aaacgagtaa ttatcctcac | 180 |
| tttacattca ggttcattct agacaacgac cctcaggatg agcgtatctc aaatttacct | 240 |
| acgcatggcc ccttggcagg tatgcgaata ccaataatca atgagcatgg agccgatgaa | 300 |
| ctccgtcgcg agttagagct tctcatgctc gcaagtgagg aagacgagga agtttcgtgc | 360 |
| ctaataactg atgcgctttg gtacttcgcc aatcagtcg cagactcact gaatctacgc | 420 |
| cgtttggtcc ttatgacaag ttcattattc aactttcacg cacatgtatc actgccgcaa | 480 |
| tttgacgagt tgggttacct ggacccggat gacaaaacgc gattggagga caagcgtcg | 540 |
| ggcttcccca tgctgaaagt caaagatatt aagagcgctt atagtaattg gcaaattctg | 600 |
| aaagaaattc tcggaaaaat gataaagcaa accaaagcgt cctctggagt aatctggaac | 660 |
| tccttcaagg agttagagga atctgaactt gaaacggtca tcagagaaat ccccgctccc | 720 |
| tcgttcttaa ttccactacc caagcacctt actgcaagta gcagttccct cctagatcat | 780 |
| gaccgaaccg tgtttcagtg gctggatcag caaccccgt cgtcagttct atatgtaagc | 840 |
| tttgggagta cttcggaagt ggatgaaaag gacttcttag agattgcgcg agggctcgtg | 900 |
| gatagcaaac agagcttcct gtgggtagtg agaccgggat tcgttaaggg ctcgacgtgg | 960 |
| gtcgagccgt tgccagatgg ttttctaggg gagagaggga gaatcgtgaa atgggttcca | 1020 |
| cagcaagagg ttttggctca cggagctata ggggcctttt ggacccactc tggttggaat | 1080 |
| tctactcttg aaagtgtctg tgaaggcgtt ccaatgatat tttctgattt tgggcttgac | 1140 |
| cagcctctaa acgctcgcta tatgtctgat gtgttgaagg ttggcgtgta cctggagaat | 1200 |
| ggttgggaaa gggggaaat tgccaacgcc atacgccggg taatggtgga cgaggaaggt | 1260 |
| gagtacatac gtcagaacgc tcgggtttta aaacaaaaag cggacgtcag ccttatgaag | 1320 |
| ggaggtagct cctatgaatc cctagaatcc ttggtaagct atatatcttc gttaggttct | 1380 |
| ggtgcaaacg ctgaacgtat gataacgcgc gtccacagcc aacgtgagcg tttgaacgaa | 1440 |
| acgcttgttt ctgagagaaa cgaagtcctt gccttgcttt ccagggttga agccaaaggt | 1500 |
| aaaggtattt tacaacaaaa ccagatcatt gctgaattcg aagctttgcc tgaacaaacc | 1560 |
| cggaagaaac ttgaaggtgg tccttctctt gaccttctca aatccactca ggaagcaatt | 1620 |
| gtgttgccac catgggttgc tctagctgtg aggccaaggc ctggtgtttg gaatactta | 1680 |
| cgagtcaatc tccatgctct tgtcgttgaa gaactccaac ctgctgagtt tcttcatttc | 1740 |
| aaggaagaac tcgttgatgg agttaagaat ggtaatttca ctcttgagct tgatttcgag | 1800 |
| ccattcaatg cgtctatccc tcgtccaaca ctccacaaat acattggaaa tggtgttgac | 1860 |
| ttccttaacc gtcattatc ggctaagctc ttccatgaca aggagagttt gcttccattg | 1920 |
| cttaagttcc ttcgtcttca cagccaccag ggcaagaacc tgatgttgag cgagaagatt | 1980 |
| cagaaccctca acactctgca acacaccttg aggaaagcag aagagtatct agcagagctt | 2040 |
| aagtccgaaa cactgtatga agagtttgag gccaagtttg aggagattgg tcttgagagg | 2100 |

```
ggatggggag acaatgcaga gcgtgtcctt gacatgatac gtcttctttt ggaccttctt    2160
gaggcgcctg atccttgcac tcttgagact tttcttggaa gagtaccaat ggtgttcaac    2220
gttgtgatcc tctctccaca tggttacttt gctcaggaca atgttcttgg ttaccctgac    2280
actggtggac aggttgttta cattcttgat caagttcgtg ctctggagat agagatgctt    2340
caacgtatta agcaacaagg actcaacatt aaaccaagga ttctcattct aactcgactt    2400
ctacctgatg cggtaggaac tacatgcggt aacgtctcg agagagttta tgattctgag    2460
tactgtgata ttcttcgtgt gcccttcaga acagagaagg gtattgttcg caaatggatc    2520
tcaaggttcg aagtctggcc atatctagag acttacaccg aggatgctgc ggttgagcta    2580 tcgaagaat tgaatggcaa gcctgacctt atcattggta actacagtga tggaaatctt    2640
gttgcttctt tattggctca caaacttggt gtcactcagt gtaccattgc tcatgctctt    2700
gagaaaacaa agtacccgga ttctgatatc tactggaaga agcttgacga caagtaccat    2760
ttctcatgcc agttcactgc ggatatttc gcaatgaacc acactgattt catcatcact    2820
agtactttcc aagaaattgc tggaagcaaa gaaactgttg ggcagtatga agccacaca    2880 gcctttactc ttcccggatt gtatcgagtt gttcacggga ttgatgtgtt tgatcccaag    2940
ttcaacattg tctctcctgg tgctgatatg agcatctact cccttacac agaggagaag    3000 cgtagattga ctaagttcca ctctgagatc gaggagctcc tctacagcga tgttgagaac    3060
aaagagcact atgtgtgct caaggacaag aagaagccga ttctcttcac aatggctagg    3120
cttgatcgtg tcaagaactt gtcaggtctt gttgagtggt acgggaagaa caccgcttg     3180 cgtgagctag ctaacttggt tgttgttgga ggagacagga gaaagagtc aaaggacaat    3240 gaagagaaag cagagatgaa gaaaatgtat gatctcattg aggaatacaa gctaaacggt    3300
cagttcaggt ggatctcctc tcagatggac cgggtaagga acggtgagct gtaccggtac    3360
atctgtgaca ccaagggtgc ttttgtccaa cctgcattat atgaagcctt tgggttaact    3420
gttgtggagg ctatgacttg tggtttaccg actttcgcca cttgcaaagg tggtccagct    3480
gagatcattg tgcacggtaa atcgggtttc cacattgacc cttaccatgg tgatcaggct    3540
gctgatactc ttgctgattt cttcaccaag tgtaaggagg atccatctca ctgggatgag    3600
atctcaaaag gagggcttca gaggattgag gagaaataca cttggcaaat ctattcacag    3660
aggctcttga cattgactgg tgtgtatgga ttctggaagc atgtctcgaa ccttgaccgt    3720
cttgaggctc gccgttacct tgaaatgttc tatgcattga gtatcgccc attggctcag    3780 gctgttcctc ttgcacaaga tgattga                                       3807
```

<210> SEQ ID NO 17
<211> LENGTH: 808
<212> TYPE: PRT
<213> ORGANISM: Arabiodopsis thaliana

<400> SEQUENCE: 17

Met Ala Asn Ala Glu Arg Met Ile Thr Arg Val His Ser Gln Arg Glu
1               5                   10                  15

Arg Leu Asn Glu Thr Leu Val Ser Glu Arg Asn Glu Val Leu Ala Leu
            20                  25                  30

Leu Ser Arg Val Glu Ala Lys Gly Lys Gly Ile Leu Gln Gln Asn Gln
        35                  40                  45

Ile Ile Ala Glu Phe Glu Ala Leu Pro Glu Gln Thr Arg Lys Lys Leu
    50                  55                  60

Glu Gly Gly Pro Phe Phe Asp Leu Leu Lys Ser Thr Gln Glu Ala Ile

```
            65                  70                  75                  80
Val Leu Pro Pro Trp Val Ala Leu Ala Val Arg Pro Arg Pro Gly Val
                    85                  90                  95

Trp Glu Tyr Leu Arg Val Asn Leu His Ala Leu Val Val Glu Glu Leu
                100                 105                 110

Gln Pro Ala Glu Phe Leu His Phe Lys Glu Glu Leu Val Asp Gly Val
                115                 120                 125

Lys Asn Gly Asn Phe Thr Leu Glu Leu Asp Phe Glu Pro Phe Asn Ala
130                 135                 140

Ser Ile Pro Arg Pro Thr Leu His Lys Tyr Ile Gly Asn Gly Val Asp
145                 150                 155                 160

Phe Leu Asn Arg His Leu Ser Ala Lys Leu Phe His Asp Lys Glu Ser
                165                 170                 175

Leu Leu Pro Leu Leu Lys Phe Leu Arg Leu His Ser His Gln Gly Lys
                180                 185                 190

Asn Leu Met Leu Ser Glu Lys Ile Gln Asn Leu Asn Thr Leu Gln His
                195                 200                 205

Thr Leu Arg Lys Ala Glu Glu Tyr Leu Ala Glu Leu Lys Ser Glu Thr
210                 215                 220

Leu Tyr Glu Glu Phe Glu Ala Lys Phe Glu Glu Ile Gly Leu Glu Arg
225                 230                 235                 240

Gly Trp Gly Asp Asn Ala Glu Arg Val Leu Asp Met Ile Arg Leu Leu
                245                 250                 255

Leu Asp Leu Leu Glu Ala Pro Asp Pro Cys Thr Leu Glu Thr Phe Leu
                260                 265                 270

Gly Arg Val Pro Met Val Phe Asn Val Ile Leu Ser Pro His Gly
                275                 280                 285

Tyr Phe Ala Gln Asp Asn Val Leu Gly Tyr Pro Asp Thr Gly Gly Gln
                290                 295                 300

Val Val Tyr Ile Leu Asp Gln Val Arg Ala Leu Glu Ile Glu Met Leu
305                 310                 315                 320

Gln Arg Ile Lys Gln Gln Gly Leu Asn Ile Lys Pro Arg Ile Leu Ile
                325                 330                 335

Leu Thr Arg Leu Leu Pro Asp Ala Val Gly Thr Thr Cys Gly Glu Arg
                340                 345                 350

Leu Glu Arg Val Tyr Asp Ser Glu Tyr Cys Asp Ile Leu Arg Val Pro
                355                 360                 365

Phe Arg Thr Glu Lys Gly Ile Val Arg Lys Trp Ile Ser Arg Phe Glu
                370                 375                 380

Val Trp Pro Tyr Leu Glu Thr Tyr Thr Glu Asp Ala Ala Val Glu Leu
385                 390                 395                 400

Ser Lys Glu Leu Asn Gly Lys Pro Asp Leu Ile Ile Gly Asn Tyr Ser
                405                 410                 415

Asp Gly Asn Leu Val Ala Ser Leu Leu Ala His Lys Leu Gly Val Thr
                420                 425                 430

Gln Cys Thr Ile Ala His Ala Leu Glu Lys Thr Lys Tyr Pro Asp Ser
                435                 440                 445

Asp Ile Tyr Trp Lys Lys Leu Asp Asp Lys Tyr His Phe Ser Cys Gln
450                 455                 460

Phe Thr Ala Asp Ile Phe Ala Met Asn His Thr Asp Phe Ile Ile Thr
465                 470                 475                 480

Ser Thr Phe Gln Glu Ile Ala Gly Ser Lys Glu Thr Val Gly Gln Tyr
                485                 490                 495
```

Glu Ser His Thr Ala Phe Thr Leu Pro Gly Leu Tyr Arg Val Val His
            500                 505                 510

Gly Ile Asp Val Phe Asp Pro Lys Phe Asn Ile Val Ser Pro Gly Ala
            515                 520                 525

Asp Met Ser Ile Tyr Phe Pro Tyr Thr Glu Glu Lys Arg Arg Leu Thr
530                 535                 540

Lys Phe His Ser Glu Ile Glu Glu Leu Leu Tyr Ser Asp Val Glu Asn
545                 550                 555                 560

Lys Glu His Leu Cys Val Leu Lys Asp Lys Lys Pro Ile Leu Phe
                565                 570                 575

Thr Met Ala Arg Leu Asp Arg Val Lys Asn Leu Ser Gly Leu Val Glu
            580                 585                 590

Trp Tyr Gly Lys Asn Thr Arg Leu Arg Glu Leu Ala Asn Leu Val Val
            595                 600                 605

Val Gly Gly Asp Arg Arg Lys Glu Ser Lys Asp Asn Glu Glu Lys Ala
            610                 615                 620

Glu Met Lys Lys Met Tyr Asp Leu Ile Glu Glu Tyr Lys Leu Asn Gly
625                 630                 635                 640

Gln Phe Arg Trp Ile Ser Ser Gln Met Asp Arg Val Arg Asn Gly Glu
                645                 650                 655

Leu Tyr Arg Tyr Ile Cys Asp Thr Lys Gly Ala Phe Val Gln Pro Ala
            660                 665                 670

Leu Tyr Glu Ala Phe Gly Leu Thr Val Val Glu Ala Met Thr Cys Gly
            675                 680                 685

Leu Pro Thr Phe Ala Thr Cys Lys Gly Gly Pro Ala Glu Ile Ile Val
            690                 695                 700

His Gly Lys Ser Gly Phe His Ile Asp Pro Tyr His Gly Asp Gln Ala
705                 710                 715                 720

Ala Asp Thr Leu Ala Asp Phe Phe Thr Lys Cys Lys Glu Asp Pro Ser
                725                 730                 735

His Trp Asp Glu Ile Ser Lys Gly Gly Leu Gln Arg Ile Glu Glu Lys
            740                 745                 750

Tyr Thr Trp Gln Ile Tyr Ser Gln Arg Leu Leu Thr Leu Thr Gly Val
            755                 760                 765

Tyr Gly Phe Trp Lys His Val Ser Asn Leu Asp Arg Leu Glu Ala Arg
            770                 775                 780

Arg Tyr Leu Glu Met Phe Tyr Ala Leu Lys Tyr Arg Pro Leu Ala Gln
785                 790                 795                 800

Ala Val Pro Leu Ala Gln Asp Asp
                805

<210> SEQ ID NO 18
<211> LENGTH: 2427
<212> TYPE: DNA
<213> ORGANISM: Arabiodopsis thaliana

<400> SEQUENCE: 18
atggcaaacg ctgaacgtat gattacccgt gtccactccc aacgcgaacg cctgaacgaa     60
accctggtgt cggaacgcaa cgaagttctg cactgctga gccgtgtgga agctaagggc    120
aaaggtattc tgcagcaaaa ccagattatc gcggaatttg aagccctgcc ggaacaaacc    180
cgcaaaaagc tggaaggcgg tccgtttttc gatctgctga atctacgca ggaagcgatc    240 gttctgccgc cgtgggtcgc actggcagtg cgtccgcgtc cgggcgtttg ggaatatctg    300

| | |
|---|---|
| cgtgtcaacc tgcatgcact ggtggttgaa gaactgcagc cggctgaatt tctgcacttc | 360 |
| aaggaagaac tggttgacgg cgtcaaaaac ggtaatttta ccctggaact ggattttgaa | 420 |
| ccgttcaatg ccagtatccc gcgtccgacg ctgcataaat atattggcaa cggtgtggac | 480 |
| tttctgaatc gccatctgag cgcaaagctg ttccacgata agaatctct gctgccgctg | 540 |
| ctgaaattcc tgcgtctgca tagtcaccag ggcaagaacc tgatgctgtc cgaaaaaatt | 600 |
| cagaacctga taccctgca cacacgctg cgcaaggcgg aagaatacct ggccgaactg | 660 |
| aaaagtgaaa ccctgtacga agaattcgaa gcaaagttcg aagaaattgg cctggaacgt | 720 |
| ggctggggtg acaatgctga acgtgttctg gatatgatcc gtctgctgct ggacctgctg | 780 |
| gaagcaccgg acccgtgcac cctggaaacg tttctgggtc gcgtgccgat ggttttcaac | 840 |
| gtcgtgattc tgtccccgca tggctatttt gcacaggaca atgtgctggg ttacccggat | 900 |
| accggcggtc aggttgtcta tattctggat caagttcgtg cgctggaaat tgaaatgctg | 960 |
| cagcgcatca gcagcaagg cctgaacatc aaaccgcgta ttctgatcct gacccgtctg | 1020 |
| ctgccggatg cagttggtac cacgtgcggt gaacgtctgg aacgcgtcta tgacagcgaa | 1080 |
| tactgtgata ttctgcgtgt cccgtttcgc accgaaaagg gtattgtgcg taaatggatc | 1140 |
| agtcgcttcg aagtttggcc gtatctgaa acctacacgg aagatgcggc cgtggaactg | 1200 |
| tccaaggaac tgaatggcaa accggacctg attatcggca actatagcga tggtaatctg | 1260 |
| gtcgcatctc tgctggctca taaactgggt gtgacccagt gcacgattgc acacgctctg | 1320 |
| gaaaagacca aatatccgga ttcagacatc tactggaaaa agctggatga caaatatcat | 1380 |
| ttttcgtgtc agttccaccgc ggacattttt gccatgaacc acacggattt tattatcacc | 1440 |
| agtacgttcc aggaaatcgc gggctccaaa gaaaccgtgg gtcaatacga atcacatacc | 1500 |
| gccttcacgc tgccgggcct gtatcgtgtg gttcacggta tcgatgtttt tgacccgaaa | 1560 |
| ttcaatattg tcagtccggg cgcggatatg tccatctatt ttccgtacac cgaagaaaag | 1620 |
| cgtcgcctga cgaaattcca ttcagaaatt gaagaactgc tgtactcgga cgtggaaaac | 1680 |
| aaggaacacc tgtgtgttct gaaagataaa aagaaaccga tcctgtttac catggcccgt | 1740 |
| ctggatcgcg tgaagaatct gtcaggcctg gttaatggg atggtaaaaa cacgcgtctg | 1800 |
| cgcgaactgg caaatctggt cgtggttggc ggtgaccgtc gcaaggaatc gaaagataac | 1860 |
| gaagaaaagg ctgaaatgaa gaaaatgtac gatctgatcg aagaatacaa gctgaacggc | 1920 |
| cagtttcgtt ggatcagctc tcaaatggac cgtgtgcgca atggcgaact gtatcgctac | 1980 |
| atttgcgata ccaagggtgc gttttgttcag ccggcactgt acgaagcttt cggcctgacc | 2040 |
| gtcgtggaag ccatgacgtg cggtctgccg accttttgcga cgtgtaaagg cggtccggcc | 2100 |
| gaaattatcg tgcatggcaa atctggtttc catatcgatc cgtatcacgg tgatcaggca | 2160 |
| gctgacaccc tggcggattt ctttacgaag tgtaaagaag acccgtcaca ctgggatgaa | 2220 |
| atttcgaagg gcggtctgca acgtatcgaa gaaaaatata cctggcagat ttacagccaa | 2280 |
| cgcctgctga ccctgacggg cgtctacggt ttttggaaac atgtgtctaa tctggatcgc | 2340 |
| ctggaagccc gtcgctatct ggaaatgttt tacgcactga gtatcgccc gctggcacaa | 2400 |
| gccgttccgc tggcacagga cgactaa | 2427 |

<210> SEQ ID NO 19
<211> LENGTH: 464
<212> TYPE: PRT
<213> ORGANISM: Oryza brachyantha

<400> SEQUENCE: 19

```
Met Glu Asn Gly Ser Ser Pro Leu His Val Ile Phe Pro Trp Leu
1               5                   10                  15

Ala Phe Gly His Leu Leu Pro Phe Leu Asp Leu Ala Glu Arg Leu Ala
            20                  25                  30

Ala Arg Gly His Arg Val Ser Phe Val Ser Thr Pro Arg Asn Leu Ala
            35                  40                  45

Arg Leu Arg Pro Val Arg Pro Ala Leu Arg Gly Leu Val Asp Leu Val
        50                  55                  60

Ala Leu Pro Leu Pro Arg Val His Gly Leu Pro Asp Gly Ala Glu Ala
65                  70                  75                  80

Thr Ser Asp Val Pro Phe Glu Lys Phe Glu Leu His Arg Lys Ala Phe
                85                  90                  95

Asp Gly Leu Ala Ala Pro Phe Ser Ala Phe Leu Asp Ala Ala Cys Ala
                100                 105                 110

Gly Asp Lys Arg Pro Asp Trp Val Ile Pro Asp Phe Met His Tyr Trp
            115                 120                 125

Val Ala Ala Ala Ala Gln Lys Arg Gly Val Pro Cys Ala Val Leu Ile
        130                 135                 140

Pro Cys Ser Ala Asp Val Met Ala Leu Tyr Gly Gln Pro Thr Glu Thr
145                 150                 155                 160

Ser Thr Glu Gln Pro Glu Ala Ile Ala Arg Ser Met Ala Ala Glu Ala
                165                 170                 175

Pro Ser Phe Glu Ala Glu Arg Asn Thr Glu Glu Tyr Gly Thr Ala Gly
            180                 185                 190

Ala Ser Gly Val Ser Ile Met Thr Arg Phe Ser Leu Thr Leu Lys Trp
        195                 200                 205

Ser Lys Leu Val Ala Leu Arg Ser Cys Pro Gly Leu Glu Pro Gly Val
    210                 215                 220

Phe Thr Thr Leu Thr Arg Val Tyr Ser Lys Pro Val Val Pro Phe Gly
225                 230                 235                 240

Leu Leu Pro Pro Arg Arg Asp Gly Ala His Gly Val Arg Lys Asn Gly
                245                 250                 255

Glu Asp Asp Gly Ala Ile Ile Arg Trp Leu Asp Glu Gln Pro Ala Lys
            260                 265                 270

Ser Val Val Tyr Val Ala Leu Gly Ser Glu Ala Pro Val Ser Ala Asp
        275                 280                 285

Leu Leu Arg Glu Leu Ala His Gly Leu Glu Leu Ala Gly Thr Arg Phe
    290                 295                 300

Leu Trp Ala Leu Arg Arg Pro Ala Gly Val Asn Asp Gly Asp Ser Ile
305                 310                 315                 320

Leu Pro Asn Gly Phe Leu Glu Arg Thr Gly Glu Arg Gly Leu Val Thr
                325                 330                 335

Thr Gly Trp Val Pro Gln Val Ser Ile Leu Ala His Ala Ala Val Cys
            340                 345                 350

Ala Phe Leu Thr His Cys Gly Trp Gly Ser Val Val Glu Gly Leu Gln
        355                 360                 365

Phe Gly His Pro Leu Ile Met Leu Pro Ile Ile Gly Asp Gln Gly Pro
    370                 375                 380

Asn Ala Arg Phe Leu Glu Gly Arg Lys Val Gly Val Ala Val Pro Arg
385                 390                 395                 400

Asn His Ala Asp Gly Ser Phe Asp Arg Ser Gly Val Ala Gly Ala Val
                405                 410                 415
```

```
Arg Ala Val Ala Val Glu Glu Gly Lys Ala Phe Ala Ala Asn Ala
            420                 425                 430

Arg Lys Leu Gln Glu Ile Val Ala Asp Arg Arg Asp Glu Arg Cys
        435                 440                 445

Thr Asp Gly Phe Ile His His Leu Thr Ser Trp Asn Glu Leu Glu Ala
    450                 455                 460

<210> SEQ ID NO 20
<211> LENGTH: 1395
<212> TYPE: DNA
<213> ORGANISM: Oryza brachyantha

<400> SEQUENCE: 20
atggaaaatg gtagcagtcc gctgcatgtt gttattttc cgtggctggc atttggtcat      60
ctgctgccgt ttctggatct ggcagaacgt ctggcagcac gtggtcatcg tgttagcttt     120
gttagcacac cgcgtaatct ggcacgtctg cgtccggttc gtccggcact gcgtggtctg     180
gttgatctgg ttgcactgcc gctgcctcgt gttcatggtc tgccggatgg tgccgaagca     240
accagtgatg ttccgtttga aaaatttgaa ctgcaccgca aagcatttga tggcctggct     300
gcaccgttta gcgcatttct ggatgcagca tgtgccggtg ataaacgtcc ggattgggtt     360
attccggatt ttatgcatta ttggggttgca gcagcagcac agaaacgtgg tgttccgtgt     420
gcagttctga ttccgtgtag cgcagatgtt atggcactgt atggtcagcc gaccgaaacc     480
agcaccgaac agccggaagc aattgcacgt agcatggcag cagaagcacc gagctttgaa     540
gcagaacgta ataccgaaga atatggtaca gccggtgcaa gcggtgttag cattatgacc     600
cgttttagtc tgaccctgaa atggtcaaaa ctggttgccc tgcgtagctg tccggaactg     660
gaaccgggtg ttttaccac actgacccgt gtttatagca aaccggttgt gccgtttggt     720
ctgctgcctc cgcgtcgtga tggtgcacat ggtgttcgta aaaatggtga agatgatggt     780
gccattattc gttggctgga tgaacagcct gcaaaaagcg ttgtttatgt tgcactgggt     840
agcgaagcac cggtttcagc cgatctgctg cgtgaactgg cacatggtct ggaattagca     900
ggcacccgtt ttctgtgggc tctgcgtcgt cctgccggtg ttaatgatgg tgatagcatt     960
ctgccgaatg gttttctgga acgtaccggt gaacgcggtc tggttaccac cggttgggtt    1020
ccgcaggtta gtattctggc ccatgcagca gtttgtgcat ttctgacccca ttgtggttgg    1080
ggtagcgttg ttgaaggttt acagtttggc catccgctga ttatgctgcc gattattggt    1140
gatcagggtc cgaatgcacg ctttctggaa ggtcgtaaag ttggtgttgc agttccgcgt    1200
aaccatgcag atggtagctt tgatcgtagc ggtgttgccg gtgccgttcg tgcagttgca    1260
gttgaagaag aaggtaaagc ctttgcagca aatgcccgta aactgcaaga aattgttgca    1320
gatcgtgaac gtgatgaacg ttgtaccgat ggttttattc atcatctgac cagctggaat    1380
gaactggaag cataa                                                     1395
```

BIOSYNTHETIC PRODUCTION OF STEVIOL GLYCOSIDES REBAUDIOSIDE J AND REBAUDIOSIDE N

CROSS-REFERENCE TO RELATED APPLICATIONS

This application is a continuation of International Application No. PCT/US2019/021876, filed on Mar. 12, 2019, which claims priority to U.S. Provisional Application No. 62/641,590, filed on Mar. 12, 2018, and U.S. Provisional Application No. 62/682,260, filed on Jun. 8, 2018, and U.S. Provisional Application No. 62/695,252, filed on Jul. 9, 2018, the contents of each of which are incorporated by reference herein in their entirety.

FIELD OF THE INVENTION

The present disclosure generally relates to the biosynthesis of steviol glycosides. More specifically, the present disclosure relates to biocatalytic processes for preparing compositions comprising rebaudioside J ("Reb J") and/or rebaudioside N ("Reb N"), as well as recombinant polypeptides having enzymatic activity useful in the relevant biosynthetic pathways for producing Reb J and/or Reb N.

BACKGROUND OF THE INVENTION

Steviol glycosides are a class of compounds found in the leaves of *Stevia rebaudiana* plant that can be used as high intensity, low-calorie sweeteners. These naturally occurring steviol glycosides share the same basic diterpene structure (steviol backbone) but differ in the number and type of carbohydrate residues (e.g., glucose, rhamnose, and xylose residues) at the C13 and C19 positions of the steviol backbone. Interestingly, these variations in sugar 'ornamentation' of the basic steviol structure often dramatically and unpredictably affect the properties of the resulting steviol glycoside. The properties that are affected can include, without limitation, the overall taste profile, the presence and extent of any off-flavors, crystallization point, "mouth feel", solubility and perceived sweetness among other differences. Steviol glycosides with known structures include stevioside, rebaudioside A, rebaudioside B, rebaudioside C, rebaudioside D, rebaudioside E, rebaudioside F, rebaudioside M, rebaudioside J, rebaudioside N, and dulcoside A.

On a dry weight basis, stevioside, rebaudioside A, rebaudioside C, and dulcoside A account for approximately 9.1%, 3.8%, 0.6%, and 0.3%, respectively, of the total weight of all steviol glycosides found in wild type *stevia* leaves. Other steviol glycosides such as Reb J and Reb N are present in significantly lower amounts. Extracts from the *Stevia rebaudiana* plant are commercially available. In such extracts, stevioside and rebaudioside A typically are the primary components, while the other known steviol glycosides are present as minor or trace components. The actual content level of the various steviol glycosides in any given *stevia* extract can vary depending on, for example, the climate and soil in which the *stevia* plants are grown, the conditions under which the *stevia* leaves are harvested, and the processes used to extract the desired steviol glycosides. To illustrate, the amount of rebaudioside A in commercial preparations can vary from about 20% to more than about 90% by weight of the total steviol glycoside content, while the amount of rebaudioside B, rebaudioside C, and rebaudioside D, respectively, can be about 1-2%, about 7-15%, and about 2% by weight of the total steviol glycoside content. In such extracts, rebaudioside J and rebaudioside N typically account for, individually, less than 0.5% by weight of the total steviol glycoside content.

As natural sweeteners, different steviol glycosides have different degrees of sweetness, mouth feel, and aftertastes. The sweetness of steviol glycosides is significantly higher than that of table sugar (i.e., sucrose). For example, stevioside itself is 100-150 times sweeter than sucrose but has a bitter aftertaste as noted in numerous taste tests, while rebaudiosides A and E are 250-450 times sweeter than sucrose and the aftertaste profile is much better than stevioside. However, these steviol glycosides themselves still retain a noticeable aftertaste. Accordingly, the overall taste profile of any *stevia* extract is profoundly affected by the relative content of the various steviol glycosides in the extract, which in turn may be affected by the source of the plant, the environmental factors (such as soil content and climate), and the extraction process. In particular, variations of the extraction conditions can lead to inconsistent compositions of the steviol glycosides in the *stevia* extracts, such that the taste profile varies among different batches of extraction productions. The taste profile of *stevia* extracts also can be affected by plant-derived or environment-derived contaminants (such as pigments, lipids, proteins, phenolics, and saccharides) that remain in the product after the extraction process. These contaminants typically have off-flavors undesirable for the use of the *stevia* extract as a sweetener. In addition, the process of isolating individual or specific combinations of steviol glycosides that are not abundant in *stevia* extracts can be cost- and resource-wise prohibitive.

Further, the extraction process from plants typically employs solid-liquid extraction techniques using solvents such as hexane, chloroform, and ethanol. Solvent extraction is an energy-intensive process, and can lead to problems relating to toxic waste disposal. Thus, new production methods are needed to both reduce the costs of steviol glycoside production as well as to lessen the environmental impact of large scale cultivation and processing.

Accordingly, there is a need in the art for novel preparation methods of steviol glycosides, particularly minor steviol glycosides such as Reb J and Reb N, that can yield products with better and more consistent taste profiles. More preferably, such preparation methods can make use of more abundant steviol glycosides such as Reb A, to reduce the cost of production.

SUMMARY OF THE INVENTION

The present disclosure encompasses, in some embodiments, a method of preparing Reb J from Reb A as well as the preparation of Reb N from Reb A through the intermediate of Reb J. In some embodiments, the present disclosure provides a method of preparing Reb N from Reb I as well as the preparation of Reb N from Reb A through the intermediate of Reb I.

In one embodiment, the current disclosure provides for the production of steviol glycoside rebaudioside J "Reb J", or 13-[(2-O-β-D-glucopyranosyl-3-O-β-D-glucopyranosyl-β-D-glucopyranosyl)oxy] ent-kaur-16-en-19-oic acid-[(2-O-α-L-rhamnopyranosyl-β-D-glucopyranosyl) ester], by various 1,2-rhamnosyltransferase enzymes described herein from Reb A. FIG. 1 shows the chemical structure of Reb J.

In another embodiment, the current disclosure provides for the production of steviol glycoside rebaudioside N "Reb N", or 13-[(2-O-β-D-glucopyranosyl-3-O-β-D-glucopyranosyl-β-D-glucopyranosyl)oxy] ent-kaur-16-en-19-oic acid-

[(2-O-α-L-rhamnopyranosyl-3-O-β-D-glucopyranosyl-β-D-glucopyranosyl) ester] by various UDP-glycosyltransferases described herein from Reb J. FIG. 2 shows the chemical structure of Reb N.

The current method provides an approach for the synthesis of specific steviol glycosides using certain specific synthetic pathways.

In terms of product/commercial utility there are several dozen products containing steviol glycosides on the market in the United States and can be used in everything from foods, beverages, and dietary supplements to analgesics and pest repellents. Products containing steviol glycosides can be liquids, granular formulations, gels or aerosols.

Provided herein, inter alia, are biosynthetic methods of preparing a rebaudioside, such as rebaudioside N, the methods comprising reacting a steviol glycoside composition with a rhamnose donor moiety in the presence of a first recombinant polypeptide having 1,2-rhamnosytransferase activity; wherein the first recombinant polypeptide comprises an amino acid sequence having at least 80% (e.g., at least 80%, at least 85%, at least 90%, at least 95%, at least 96%, at least 97%, at least 98%, at least 99% or 100%) sequence identity to SEQ ID NO: 3, SEQ ID NO: 9, or SEQ ID NO: 19.

In some embodiments, the first recombinant polypeptide comprises an amino acid sequence having at least 80%, at least 85%, at least 90%, at least 95%, at least 96%, at least 97%, at least 98%, at least 99%, or 100% identity to SEQ ID NO: 3.

In some embodiments, the first recombinant polypeptide comprises an amino acid sequence having at least 80%, at least 85%, at least 90%, at least 95%, at least 96%, at least 97%, at least 98%, at least 99%, or 100% identity to SEQ ID NO: 9.

In some embodiments, the first recombinant polypeptide comprises an amino acid sequence having at least 80%, at least 85%, at least 90%, at least 95%, at least 96%, at least 97%, at least 98%, at least 99%, or 100% identity to SEQ ID NO: 19.

In some embodiments, biosynthetic methods provided herein comprise expressing the first recombinant polypeptide in a transformed cellular system. In some embodiments, the transformed cellular system is selected from the group consisting of a yeast, a non-steviol glycoside producing plant, an alga, a fungus, and a bacterium. In some embodiments, the bacterium or yeast is selected from the group consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula*; Debaryomyces; *Mucor; Pichia; Torulopsis; Aspergillus; Arthrobotlys; Brevibacteria; Microbacterium; Arthrobacter; Citrobacter; Klebsiella; Pantoea*; and *Clostridium.*

In some embodiments, biosynthetic methods provided herein comprise a reacting step that is performed in the transformed cellular system. In other embodiments, the reacting step can be performed in vitro. In some embodiments, biosynthetic methods comprise isolating the first recombinant polypeptide from the transformed cellular system and the reacting step can be performed in vitro.

In some embodiments, the rhamnose donor is rhamnose. In some embodiments, the rhamnose donor is L-rhamnose. In some embodiments, the rhamnose donor moiety is UDP-L-rhamnose.

In some embodiments, the steviol glycoside composition comprises rebaudioside A and the reacting step leads to the production of rebaudioside J.

In some embodiments, biosynthetic methods provided herein further comprise reacting the rebaudioside J with a glucose donor moiety in the presence of a second recombinant polypeptide having glucosytransferase activity. In some embodiments, the glucose donor moiety is generated in situ.

In some embodiments, the second recombinant polypeptide has both glucosyltransferase activity and sucrose synthase activity. In some embodiments, the second recombinant polypeptide comprises an amino acid sequence having at least 80% (e.g., at least 80%, at least 85%, at least 90%, at least 95%, at least 96%, at least 97%, at least 98%, at least 99% or 100%) sequence identity to SEQ ID NO: 7, SEQ ID NO: 11, SEQ ID NO: 13, or SEQ ID NO: 15.

In some embodiments, the second recombinant polypeptide comprises an amino acid sequence having at least 80%, at least 85%, at least 90%, at least 95%, at least 96%, at least 97%, at least 98%, at least 99%, or 100% identity to SEQ ID NO: 7.

In some embodiments, the second recombinant polypeptide comprises an amino acid sequence having at least 80%, at least 85%, at least 90%, at least 95%, at least 96%, at least 97%, at least 98%, at least 99%, or 100% identity to SEQ ID NO: 11.

In some embodiments, the second recombinant polypeptide comprises an amino acid sequence having at least 80%, at least 85%, at least 90%, at least 95%, at least 96%, at least 97%, at least 98%, at least 99%, or 100% identity to SEQ ID NO: 13.

In some embodiments, the second recombinant polypeptide comprises an amino acid sequence having at least 80%, at least 85%, at least 90%, at least 95%, at least 96%, at least 97%, at least 98%, at least 99%, or 100% identity to SEQ ID NO: 15.

In some embodiments, biosynthetic methods provided herein further comprise reacting the rebaudioside J with a glucose donor moiety in the presence of a third recombinant polypeptide having sucrose synthase activity.

In some embodiments, the steviol glycoside composition can include rebaudioside I. In some embodiments, the rebaudioside I can be prepared by reacting a steviol glycoside composition comprising rebaudioside A with a glucose donor moiety in the presence of a second recombinant polypeptide having glucosyltransferase activity.

In some embodiments, biosynthetic methods provided herein further comprise reacting the steviol glycoside composition comprising rebaudioside A with a glucose donor moiety in the presence of a third recombinant polypeptide having sucrose synthase activity.

Also provided herein, inter alia, are biosynthetic methods of preparing a rebaudioside, such as rebaudioside J, the methods comprising reacting a steviol glycoside composition comprising rebaudioside A with a rhamnose donor moiety in the presence of a recombinant polypeptide having 1,2-rhamnosytransferase activity; wherein said recombinant polypeptide comprises an amino acid sequence having at least 80% (e.g., at least 80%, at least 85%, at least 90%, at least 95%, at least 96%, at least 97%, at least 98%, at least 99% or 100%) sequence identity to SEQ ID NO: 3, SEQ ID NO: 9, or SEQ ID NO: 19.

In some embodiments, the recombinant polypeptide having 1,2-rhamnosytransferase activity comprises an amino acid sequence having at least 80%, at least 85%, at least 90%, at least 95%, at least 96%, at least 97%, at least 98%, at least 99%, or 100% identity to SEQ ID NO: 3.

In some embodiments, the recombinant polypeptide having 1,2-rhamnosytransferase activity comprises an amino acid sequence having at least 80%, at least 85%, at least 90%, at least 95%, at least 96%, at least 97%, at least 98%, at least 99%, or 100% identity to SEQ ID NO: 9.

In some embodiments, the recombinant polypeptide having 1,2-rhamnosytransferase activity comprises an amino acid sequence having at least 80%, at least 85%, at least 90%, at least 95%, at least 96%, at least 97%, at least 98%, at least 99%, or 100% identity to SEQ ID NO: 19.

Aspects of the present disclosure also provide a rebaudioside obtainable by or produced by any biosynthetic method described herein, including any of the above-mentioned embodiments.

Aspects of the present disclosure also provide a nucleic acid encoding a polypeptide as described herein. In some embodiments, the nucleic acid comprises a sequence encoding a polypeptide comprising an amino acid sequence having at least 80%, at least 85%, at least 90%, at least 95%, at least 96%, at least 97%, at least 98%, at least 99%, or 100% identity to SEQ ID NO: 3, SEQ ID NO: 9, or SEQ ID NO: 19. In some embodiments, the nucleic acid comprises a sequence having at least 80%, at least 85%, at least 90%, at least 95%, at least 96%, at least 97%, at least 98%, 99%, or 100% identity to SEQ ID NO: 4, SEQ ID NO: 10, or SEQ ID NO: 20. In some embodiments, the nucleic acid comprises the sequence of SEQ ID NO: 4. In some embodiments, the nucleic acid comprises the sequence of SEQ ID NO: 10. In some embodiments, the nucleic acid comprises the sequence of SEQ ID NO: 20. In some embodiments, the nucleic acid is a plasmid or other vector.

Aspects of the present disclosure also provide a cell comprising a nucleic acid described herein, including any of the above-mentioned embodiments.

Other aspects of the present disclosure provide a composition comprising at least one polypeptide comprising an amino acid sequence having at least 80%, at least 85%, at least 90%, at least 95%, at least 96%, at least 97%, at least 98%, at least 99%, or 100% identity to SEQ ID NO: 3, SEQ ID NO: 9, or SEQ ID NO: 19. In some embodiments, the composition comprises at least one polypeptide comprising the sequence of SEQ ID NO: 3. In some embodiments, the composition comprises at least one polypeptide comprising the sequence of SEQ ID NO: 9. In some embodiments, the composition comprises at least one polypeptide comprising the sequence of SEQ ID NO: 19. In some embodiments, the composition is an in vitro reaction mixture, e.g., comprising a rhamnose donor moiety as described herein and a steviol glycoside composition as described herein.

Aspects of the present disclosure provide a cell comprising at least one polypeptide comprising an amino acid sequence having at least 80%, at least 85%, at least 90%, at least 95%, at least 96%, at least 97%, at least 98%, at least 99%, or 100% identity to SEQ ID NO: 3, SEQ ID NO: 9, or SEQ ID NO: 19. In some embodiments, the cell comprises at least one polypeptide comprising the sequence of SEQ ID NO: 3. In some embodiments, the cell comprises at least one polypeptide comprising the sequence of SEQ ID NO: 9. In some embodiments, the cell comprises at least one polypeptide comprising the sequence of SEQ ID NO: 19. In some embodiments, the cell is a yeast cell, a non-steviol glycoside producing plant cell, an algal cell, a fungal cell, or a bacterial cell. In some embodiments, the bacterium or yeast cell is selected from the group consisting of *Escherichia*; *Salmonella*; *Bacillus*; *Acinetobacter*; *Streptomyces*; *Corynebacterium*; *Methylosinus*; *Methylomonas*; *Rhodococcus*; *Pseudomonas*; *Rhodobacter*; *Synechocystis*; *Saccharomyces*; *Zygosaccharomyces*; *Kluyveromyces*; *Candida*; *Hansenula*; *Debaryomyces*; *Mucor*; *Pichia*; *Torulopsis*; *Aspergillus*; *Arthrobotlys*; *Brevibacteria*; *Microbacterium*; *Arthrobacter*; *Citrobacter*; *Klebsiella*; *Pantoea*; and *Clostridium*. In some embodiments, the cell further comprises a second polypeptide having glucosytransferase activity or glucosyltransferase activity and sucrose synthase activity as described herein, such as a second polypeptide comprising an amino acid sequence having at least 80% (e.g., at least 80%, at least 85%, at least 90%, at least 95%, at least 96%, at least 97%, at least 98%, at least 99% or 100%) sequence identity to SEQ ID NO: 7, SEQ ID NO: 11, SEQ ID NO: 13, or SEQ ID NO: 15.

As for the cellular system in the embodiment, it can be selected from the group consisting of one or more bacteria, one or more yeasts, and a combination thereof, or any cellular system that would allow the genetic transformation with the selected genes and thereafter the biosynthetic production of the desired steviol glycosides. In a most preferred microbial system, *E. coli* are used to produce the desired steviol glycoside compounds.

In some embodiments, the disclosure provides a mutant of EU11 enzyme comprising the amino acid sequence of SEQ ID NO: 3 and identified as EUCP1. In some embodiments, the disclosure provides a recombinant polypeptide comprising an amino acid sequence having at least 90% (e.g., at least 90%, at least 95%, at least 96%, at least 97%, at least 98%, at least 99% or 100%) identity to SEQ ID NO: 3.

In some embodiments, the disclosure provides a DNA molecule having a sequence corresponding to EUCP1 and comprising SEQ ID NO: 4. In some embodiments, the disclosure provides a nucleic acid molecule having a sequence having at least 90% (e.g., at least 90%, at least 95%, at least 96%, at least 97%, at least 98%, at least 99% or 100%) identity to SEQ ID NO: 4.

In some embodiments, the disclosure provides a mutant of the EU11 enzyme comprising the amino acid sequence of SEQ ID NO: 1. In some embodiments, the disclosure provides a recombinant polypeptide comprising an amino acid sequence having at least 90% (e.g., at least 90%, at least 95%, at least 96%, at least 97%, at least 98%, at least 99% or 100%) identity to SEQ ID NO: 1.

In some embodiments, the disclosure provides a DNA molecule having a sequence corresponding to EU11 and comprising SEQ ID NO: 2. In some embodiments, the disclosure provides a nucleic acid molecule having a sequence having at least 90% (e.g., at least 90%, at least 95%, at least 96%, at least 97%, at least 98%, at least 99% or 100%) identity to SEQ ID NO: 2.

In some embodiments, the disclosure provides an enzyme referred herein as UGT2E-B comprising the amino acid sequence of SEQ ID NO: 9. In some embodiments, the disclosure provides a recombinant polypeptide comprising an amino acid sequence having at least 90% (e.g., at least 90%, at least 95%, at least 96%, at least 97%, at least 98%, at least 99% or 100%) identity to SEQ ID NO: 9.

In some embodiments, the disclosure provides a DNA molecule having a sequence corresponding to UGT2E-B and comprising SEQ ID NO: 10. In some embodiments, the disclosure provides a nucleic acid molecule having a sequence having at least 90% (e.g., at least 90%, at least 95%, at least 96%, at least 97%, at least 98%, at least 99% or 100%) identity to SEQ ID NO: 10.

In some embodiments, the disclosure provides an enzyme referred herein as NX114 comprising the amino acid sequence of SEQ ID NO: 19. In some embodiments, the disclosure provides a recombinant polypeptide comprising an amino acid sequence having at least 90% (e.g., at least 90%, at least 95%, at least 96%, at least 97%, at least 98%, at least 99% or 100%) identity to SEQ ID NO: 19.

In some embodiments, the disclosure provides a DNA molecule having a sequence corresponding to NX114 and comprising SEQ ID NO: 20. In some embodiments, the disclosure provides a nucleic acid molecule having a sequence having at least 90% (e.g., at least 90%, at least 95%, at least 96%, at least 97%, at least 98%, at least 99% or 100%) identity to SEQ ID NO: 20.

In some embodiments, the disclosure provides a microbial host cell comprising a vector capable of producing one or more enzymes described herein. In certain embodiments, the enzyme can be selected from the group consisting of EUCP1 [SEQ ID. NO. 3], UGT2E-B [SEQ ID. No. 9], and NX114 [SEQ ID NO. 19]. In some embodiments, the enzyme can be selected from the group consisting of CP1 [SEQ ID NO. 11] and CP2 [SEQ ID NO. 13]. In some embodiments, the enzyme can be a fusion enzyme referred herein as GS [SEQ ID No. 15]. In some embodiments, the host cell is selected from the group consisting of a bacterium, a yeast, a filamentous fungus, a cyanobacteria alga and a plant cell. In some embodiments, the host cell is selected from the group consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis; Aspergillus*; Arthrobotlys; Brevibacteria; *Microbacterium; Arthrobacter; Citrobacter; Klebsiella; Pantoea; Corynebacterium; Clostridium* (e.g., *Clostridium acetobutylicum*). In some embodiments, the host cell is a cell isolated from plants selected from the group consisting of soybean; rapeseed; sunflower; cotton; corn; tobacco; alfalfa; wheat; barley; oats; sorghum; rice; broccoli; cauliflower; cabbage; parsnips; melons; carrots; celery; parsley; tomatoes; potatoes; strawberries; peanuts; grapes; grass seed crops; sugar beets; sugar cane; beans; peas; rye; flax; hardwood trees; softwood trees; forage grasses; *Arabidopsis thaliana*; rice (*Oryza sativa*); *Hordeum vulgare*; switchgrass (*Panicum vigratum*); *Brachypodium* spp.; *Brassica* spp.; and *Crambe abyssinica*.

In some embodiments, the disclosure provides a method of producing rebaudioside J, the method comprising incubating a substrate with a recombinant polypeptide comprising an amino acid sequence having at least 80% (e.g., at least 80%, at least 85%, at least 90%, at least 95%, at least 96%, at least 97%, at least 98%, at least 99% or 100%) identity to SEQ ID NO: 3, SEQ ID NO: 9, or SEQ ID NO: 19. In some embodiments, the recombinant polypeptide is a 1,2 rhamnosyltranferase having at least 80% (e.g., at least 80%, at least 85%, at least 90%, at least 95%, at least 96%, at least 97%, at least 98%, at least 99% or 100%) identity to SEQ ID NO: 3, SEQ ID NO: 9, or SEQ ID NO: 19. In some embodiments, the substrate is selected from the group consisting of rubusoside, stevioside or rebaudioside A and combinations thereof.

In some embodiments, the disclosure provides a sweetener comprising Reb J produced by any of the embodiments of the above-mentioned method.

In some embodiments, the disclosure provides a method of producing rebaudioside N, the method comprising incubating a substrate with a first recombinant polypeptide comprising an amino acid sequence having at least 80% (e.g., at least 80%, at least 85%, at least 90%, at least 95%, at least 96%, at least 97%, at least 98%, at least 99% or 100%) identity to SEQ ID NO: 3, SEQ ID NO: 9, or SEQ ID NO: 19. In some embodiments, the substrate is selected from the group consisting of Reb J, Reb I, Reb A, stevioside or rubusoside and combinations thereof. In some embodiments, the substrate comprises Reb J. In other embodiments, the substrate comprises Reb I. In some embodiments, the method further comprises incubating a second recombinant polypeptide having glucosyltransferase activity and optionally a recombinant sucrose synthase, with the substrate and the first recombinant polypeptide.

In some embodiments, the disclosure provides a sweetener comprising Reb N produced by any of the embodiments of the above-mentioned method.

In some embodiments, the disclosure provides a method for synthesizing rebaudioside N from rebaudioside J, the method comprising: preparing a reaction mixture comprising rebaudioside J, a glucose donor moiety selected from the group consisting of sucrose, uridine diphosphate (UDP) and uridine diphosphate glucose (UDP-glucose), and a UGT enzyme, incubating the reaction mixture for a sufficient time to produce rebaudioside N, wherein a glucose is covalently coupled to the rebaudioside J to produce rebaudioside N. In various embodiments, the UGT enzyme can be a polypeptide comprising an amino acid sequence having at least 80% sequence identity to UGT76G1 [SEQ ID No. 7], CP1 [SEQ ID No. 11], CP2 [SEQ ID No. 13], or GS [SEQ ID No. 15]. In some embodiments, the method further comprises adding a sucrose synthase to the reaction mixture. In some embodiments, the sucrose synthase is selected from the group consisting of an *Arabidopsis* sucrose synthase 1, an *Arabidopsis* sucrose synthase 3 and a *Vigna radiate* sucrose synthase. In some embodiments, the sucrose synthase is an *Arabidopsis thaliana* sucrose synthase 1 (SEQ ID NO: 17).

In some embodiments, said Reb N is greater than 70% (e.g., greater than 80%, greater than 85%, greater than 90%, greater than 95%, greater than 96%, greater than 97%, greater than 98%, or greater than 99%) pure.

In some embodiments, the disclosure provides a host cell comprising a vector capable of producing an enzyme wherein the amino acid sequence corresponds to SEQ ID NO: 3, SEQ ID NO: 9, or SEQ ID NO: 19. In some embodiments, the host cell is selected from the group consisting of a bacterium, a yeast, a filamentous fungus, a cyanobacteria alga and a plant cell. In some embodiments, the host cell is selected from the group consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis; Aspergillus; Arthrobotlys; Brevibacteria; Microbacterium; Arthrobacter; Citrobacter; Klebsiella; Pantoea; Corynebacterium; Clostridium*. In some embodiments, the host cell is a cell isolated from plants selected from the group consisting of soybean; rapeseed; sunflower; cotton; corn; tobacco; alfalfa; wheat; barley; oats; sorghum; rice; broccoli; cauliflower; cabbage; parsnips; melons; carrots; celery; parsley; tomatoes; potatoes; strawberries; peanuts; grapes; grass seed crops; sugar beets; sugar cane; beans; peas; rye; flax; hardwood trees; softwood trees; forage grasses; *Arabidopsis thaliana*; rice (*Oryza sativa*); *Hordeum vulgare*; switchgrass (*Panicum vigratum*); *Brachypodium* spp.; *Brassica* spp.; and *Crambe abyssinica*.

In some embodiments, the disclosure provides a beverage product comprising: up to about 125 ppm Rebaudioside N; and at least one non-nutritive sweetener selected from the group consisting of Reb J; Reb W; Reb V; Reb D4, Reb E, and Reb M, and combinations thereof, wherein the at least one non-nutritive sweetener is present in a concentration from about 30 ppm to about 600 ppm. In some embodiments, the at least one non-nutritive sweetener is selected from the group consisting of Reb J; Reb W; Reb V; Reb D4, Reb E, and Reb M, and combinations thereof, and wherein the Reb N and the at least one non-nutritive sweetener are present in a weight ratio of about 1:5.

In some embodiments, the disclosure provides a GS fusion enzyme comprising a first domain having an amino acid sequence at least 90% identical to UGT76G1 and a second domain having an amino acid sequence at least 90% identical to AtSUS1. The GS fusion enzyme can have an amino acid sequence comprising SEQ ID NO: 15. In some embodiments, the disclosure provides a recombinant polypeptide comprising an amino acid sequence having at least 90% (e.g., at least 90%, at least 95%, at least 96%, at least 97%, at least 98%, at least 99% or 100%) identity to SEQ ID NO: 15.

In some embodiments, the disclosure provides a DNA molecule having a sequence corresponding to GS and comprising SEQ ID NO: 16. In some embodiments, the disclosure provides a nucleic acid molecule having a sequence having at least 90% (e.g., at least 90%, at least 95%, at least 96%, at least 97%, at least 98%, at least 99% or 100%) identity to SEQ ID NO: 16.

In some embodiments, the disclosure provides a UDP-glycosyltransferase comprising the UGT2E-B enzyme and having the amino acid sequence of SEQ ID NO: 9. In some embodiments, the disclosure provides a recombinant polypeptide comprising an amino acid sequence having at least 90% (e.g., at least 90%, at least 95%, at least 96%, at least 97%, at least 98%, at least 99% or 100%) identity to SEQ ID NO: 9.

In some embodiments, the disclosure provides a DNA molecule having a sequence corresponding to UGT2E-B and comprising SEQ ID NO: 10. In some embodiments, the disclosure provides a nucleic acid molecule having a sequence having at least 90% (e.g., at least 90%, at least 95%, at least 96%, at least 97%, at least 98%, at least 99% or 100%) identity to SEQ ID NO: 10.

In some embodiments, the disclosure provides a microbial host cell comprising a vector capable of producing the UGT2E-B enzyme. In some embodiments, the host cell is selected from the group consisting of a bacterium, a yeast, a filamentous fungus, a cyanobacteria alga and a plant cell. In some embodiments, the host cell is selected from the group consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis; Aspergillus; Arthrobotlys; Brevibacteria; Microbacterium; Arthrobacter; Citrobacter; Klebsiella; Pantoea; Corynebacterium; Clostridium*. In some embodiments, the host cell is a cell isolated from plants selected from the group consisting of soybean; rapeseed; sunflower; cotton; corn; tobacco; alfalfa; wheat; barley; oats; sorghum; rice; broccoli; cauliflower; cabbage; parsnips; melons; carrots; celery; parsley; tomatoes; potatoes; strawberries; peanuts; grapes; grass seed crops; sugar beets; sugar cane; beans; peas; rye; flax; hardwood trees; softwood trees; forage grasses; *Arabidopsis thaliana*; rice (*Oryza sativa*); *Hordeum yulgare*; switchgrass (*Panicum vigratum*); *Brachypodium* spp.; *Brassica* spp.; and, *Crambe abyssinica*.

In some embodiments, the disclosure provides a method of producing rebaudioside N, the method comprising incubating a substrate with a recombinant polypeptide comprising an amino acid sequence having at least 80% identity to SEQ ID NO: 11 or SEQ ID NO: 13 or SEQ ID NO: 15. In some embodiments, the substrate is selected from the group consisting of Reb J, Reb A, stevioside or rubusoside and combinations thereof. In some embodiments, the method further comprises incubating a recombinant sucrose synthase with the substrate and the recombinant polypeptide.

In some embodiments, the disclosure provides a host cell comprising a vector capable of producing the CP1 and CP2 enzymes wherein the amino acid sequence corresponds to SEQ ID NOs: 11 and 13, respectively. In some embodiments, the host cell is selected from the group consisting of a bacterium, a yeast, a filamentous fungus, a cyanobacteria alga and a plant cell. In some embodiments, the host cell is selected from the group consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis; Aspergillus; Arthrobotlys; Brevibacteria; Microbacterium; Arthrobacter; Citrobacter; Klebsiella; Pantoea; Corynebacterium; Clostridium*. In some embodiments, the host cell is a cell isolated from plants selected from the group consisting of soybean; rapeseed; sunflower; cotton; corn; tobacco; alfalfa; wheat; barley; oats; sorghum; rice; broccoli; cauliflower; cabbage; parsnips; melons; carrots; celery; parsley; tomatoes; potatoes; strawberries; peanuts; grapes; grass seed crops; sugar beets; sugar cane; beans; peas; rye; flax; hardwood trees; softwood trees; forage grasses; *Arabidopsis thaliana*; rice (*Oryza sativa*); *Hordeum yulgare*; switchgrass (*Panicum vigratum*); *Brachypodium* spp.; *Brassica* spp.; and, *Crambe abyssinica*.

In some embodiments, the disclosure provides a mutant enzyme comprising the amino acid sequence of SEQ ID NO: 11 and identified as CP1.

In some embodiments, the disclosure provides a mutant enzyme comprising the amino acid sequence of SEQ ID NO: 13 and identified as CP2.

While the disclosure is susceptible to various modifications and alternative forms, specific embodiments thereof are shown by way of example in the drawing and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure as defined by the appended claims.

Other features and advantages of this invention will become apparent in the following detailed description of preferred embodiments of this invention, taken with reference to the accompanying drawings.

DETAILED DESCRIPTION

Explanation of Terms Used Herein

Figure 1:
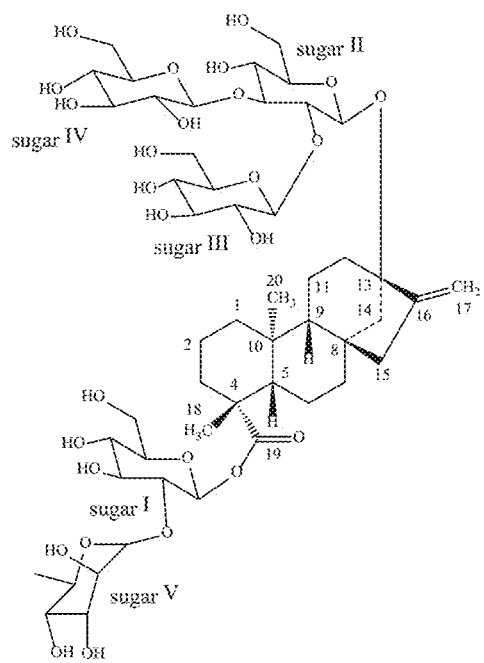
FIG. 1 shows the chemical structure of rebaudioside J ("Reb J").
Figure 2:
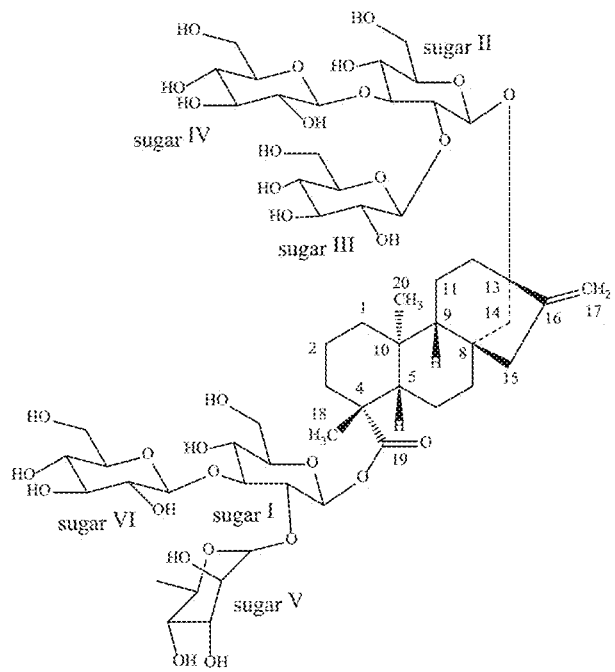
FIG. 2 shows the chemical structure of rebaudioside N ("Reb N").

Steviol Glycosides are a class of chemical compounds responsible for the sweet taste of the leaves of the South American plant *Stevia rebaudiana* (Asteraceae), and can be used as sweeteners in food, feed and beverages.

Definitions

Cellular system is any cells that provide for the expression of ectopic proteins. It included bacteria, yeast, plant cells and animal cells. It includes both prokaryotic and eukaryotic cells. It also includes the in vitro expression of proteins based on cellular components, such as ribosomes.

Coding sequence is to be given its ordinary and customary meaning to a person of ordinary skill in the art and is used without limitation to refer to a DNA sequence that encodes for a specific amino acid sequence.

Growing the Cellular System. Growing includes providing an appropriate medium that would allow cells to multiply and divide. It also includes providing resources so that cells or cellular components can translate and make recombinant proteins.

Protein Expression. Protein production can occur after gene expression. It consists of the stages after DNA has been transcribed to messenger RNA (mRNA). The mRNA is then translated into polypeptide chains, which are ultimately folded into proteins. DNA is present in the cells through transfection—a process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. Transduction is often used to describe virus-mediated DNA transfer. Transformation, transduction, and viral infection are included under the definition of transfection for this application.

Yeast. According to the current disclosure a yeast as claimed herein are eukaryotic, single-celled microorganisms classified as members of the fungus kingdom. Yeasts are unicellular organisms which evolved from multicellular ancestors but with some species useful for the current disclosure being those that have the ability to develop multicellular characteristics by forming strings of connected budding cells known as pseudo hyphae or false hyphae.

UGT Names. The names of the UGT enzymes used in the present disclosure are consistent with the nomenclature system adopted by the UGT Nomenclature Committee (Mackenzie et al., "*The UDP glycosyltransferase gene super family: recommended nomenclature updated based on evolutionary divergence*," PHARMACOGENETICS, 1997, vol. 7, pp. 255-269), which classifies the UGT genes by the combination of a family number, a letter denoting a subfamily, and a number for an individual gene. For example, the name "UGT76G1" refers to a UGT enzyme encoded by a gene belonging to UGT family number 76 (which is of plant origin), subfamily G, and gene number 1.

Structural Terms

As used herein, the singular forms "a, an" and "the" include plural references unless the content clearly dictates otherwise.

To the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration". Any embodiment described herein as "exemplary" is not necessarily to be construed as preferred or advantageous over other embodiments.

The term "complementary" is to be given its ordinary and customary meaning to a person of ordinary skill in the art and is used without limitation to describe the relationship between nucleotide bases that are capable to hybridizing to one another. For example, with respect to DNA, adenosine is complementary to thymine and cytosine is complementary to guanine. Accordingly, the subjection technology also includes isolated nucleic acid fragments that are complementary to the complete sequences as reported in the accompanying Sequence Listing as well as those substantially similar nucleic acid sequences.

The terms "nucleic acid" and "nucleotide" are to be given their respective ordinary and customary meanings to a person of ordinary skill in the art and are used without limitation to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

The term "isolated" is to be given its ordinary and customary meaning to a person of ordinary skill in the art, and when used in the context of an isolated nucleic acid or an isolated polypeptide, is used without limitation to refer to a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The terms "incubating" and "incubation" as used herein means a process of mixing two or more chemical or biological entities (such as a chemical compound and an enzyme) and allowing them to interact under conditions favorable for producing a steviol glycoside composition.

The term "degenerate variant" refers to a nucleic acid sequence having a residue sequence that differs from a reference nucleic acid sequence by one or more degenerate codon substitutions. Degenerate codon substitutions can be achieved by generating sequences in which the third position of one or more selected (or all) codons is substituted with mixed base and/or deoxy inosine residues. A nucleic acid sequence and all of its degenerate variants will express the same amino acid or polypeptide.

The terms "polypeptide," "protein,' and "peptide" are to be given their respective ordinary' and customary meanings to a person of ordinary skill in the art; the three terms are sometimes used interchangeably and are used without limitation to refer to a polymer of amino acids, or amino acid analogs, regardless of its size or function. Although "protein" is often used in reference to relatively large polypeptides, and "peptide" is often used in reference to small polypeptides, usage of these terms in the art overlaps and varies. The term 'polypeptide" as used herein refers to peptides, polypeptides, and proteins, unless otherwise noted. The terms "protein," "polypeptide," and "peptide" are used interchangeably herein when referring to a polynucleotide product. Thus, exemplary polypeptides include polynucleotide products, naturally occurring proteins, homologs, orthologs, paralogs, fragments and other equivalents, variants, and analogs of the foregoing.

The terms "polypeptide fragment" and "fragment," when used in reference to a reference polypeptide, are to be given their ordinary and customary meanings to a person of ordinary skill in the art and are used without limitation to refer to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

The term "functional fragment" of a polypeptide or protein refers to a peptide fragment that is a portion of the full-length polypeptide or protein, and has substantially the same biological activity, or carries out substantially the same function as the full-length polypeptide or protein (e.g., carrying out the same enzymatic reaction).

The terms "variant polypeptide," "modified amino acid sequence" or "modified polypeptide," which are used interchangeably, refer to an amino acid sequence that is different from the reference polypeptide by one or more amino acids, e.g., by one or more amino acid substitutions, deletions, and/or additions. In an aspect, a variant is a "functional variant" which retains some or all of the ability of the reference polypeptide.

The term "functional variant" further includes conservatively substituted variants. The term "conservatively substituted variant" refers to a peptide having an amino acid sequence that differs from a reference peptide by one or more conservative amino acid substitutions and maintains some or all of the activity of the reference peptide. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. Such substitutions are expected to have little or no effect on the apparent molecular weight or isoelectric point of the protein or polypeptide. The phrase "conservatively substituted variant" also includes peptides wherein a residue is replaced with a chemically-derivatized residue, provided that the resulting peptide maintains some or all of the activity of the reference peptide as described herein.

The term "variant," in connection with the polypeptides of the subject technology, further includes a functionally active polypeptide having an amino acid sequence at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical to the amino acid sequence of a reference polypeptide.

The term "homologous" in all its grammatical forms and spelling variations refers to the relationship between polynucleotides or polypeptides that possess a "common evolutionary origin," including polynucleotides or polypeptides from super families and homologous polynucleotides or proteins from different species (Reeck et al., CELL 50:667, 1987). Such polynucleotides or polypeptides have sequence homology, as reflected by their sequence similarity, whether in terms of percent identity or the presence of specific amino acids or motifs at conserved positions. For example, two homologous polypeptides can have amino acid sequences that are at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 900 at least 91%, at least 92%, at least 93%, at least 94%, at least 95%, at least 96%, at least 97%, at least 98%, at least 99%, and even 100% identical.

"Suitable regulatory sequences" is to be given its ordinary and customary meaning to a person of ordinary skill in the art and is used without limitation to refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" is to be given its ordinary and customary meaning to a person of ordinary skill in the art and is used without limitation to refer to a DNA sequence capable of controlling the expression of a coding sequence or functional RNA. In general, a coding sequence is located 3' to a promoter sequence. Promoters may be derived in their entirety from a native gene or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters, which cause a gene to be expressed in most cell types at most times, are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it can affect the expression of that coding sequence (i.e., that the coding sequence is under the transcriptional control of the promoter). Coding sequences can be operably linked to regulatory sequences in sense or anti sense orientation.

The term "expression" as used herein, is to be given its ordinary and customary meaning to a person of ordinary skill in the art and is used without limitation to refer to the transcription and stable accumulation of sense (mRNA) or anti sense RNA derived from the nucleic acid fragment of the subject technology. "Over-expression" refers to the production of a gene product in transgenic or recombinant organisms that exceeds levels of production in normal or non-transformed organisms.

"Transformation" is to be given its ordinary and customary meaning to a person of reasonable skill in the craft and is used without limitation to refer to the transfer of a polynucleotide into a target cell. The transferred polynucleotide can be incorporated into the genome or chromosomal DNA of a target cell, resulting in genetically stable inheritance, or it can replicate independent of the host chromosomal. Host organisms containing the transformed nucleic acid fragments are referred to as "transgenic" or "transformed".

The terms "transformed," "transgenic," and "recombinant," when used herein in connection with host cells, are to be given their respective ordinary and customary meanings to a person of ordinary skill in the art and are used without limitation to refer to a cell of a host organism, such as a plant or microbial cell, into which a heterologous nucleic acid molecule has been introduced. The nucleic acid molecule can be stably integrated into the genome of the host cell, or the nucleic acid molecule can be present as an extrachromosomal molecule. Such an extrachromosomal molecule can be auto-replicating. Transformed cells, tissues, or subjects are understood to encompass not only the end product of a transformation process, but also transgenic progeny thereof.

The terms "recombinant," "heterologous," and "exogenous," when used herein in connection with polynucleotides, are to be given their ordinary and customary meanings to a person of ordinary skill in the art and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

The terms "plasmid," "vector," and "cassette" are to be given their respective ordinary and customary meanings to a person of ordinary skill in the art and are used without limitation to refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Figure 3A:
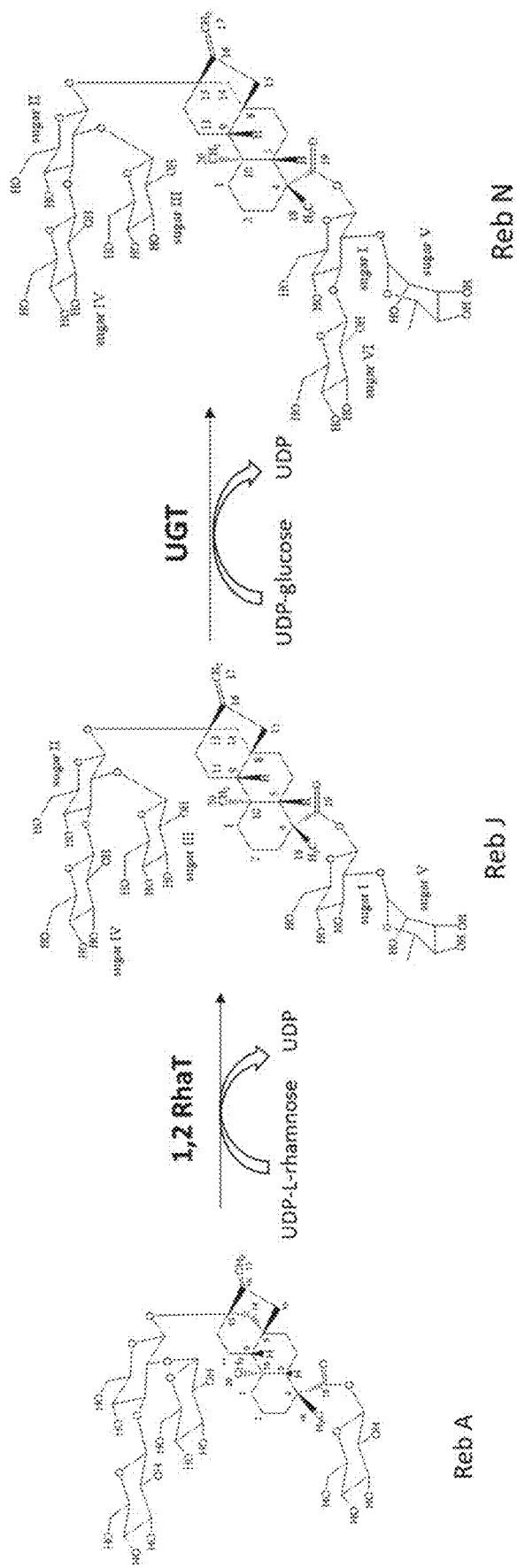
FIG. 3A illustrates the biosynthetic pathway for the production of Reb J and Reb N. More specifically, starting from rebaudioside A ("Reb A"), a 1,2 rhamnosyltransferase ("1,2 RhaT") can be used to produce Reb J by catalyzing the transfer of a rhamnose moiety from a UDP-rhamnose donor to the C-2' of the 19-O-glucose of the Reb A acceptor. In a subsequent reaction, a UDP-glycosytransferase ("UGT") can be used to produce Reb N from Reb J by catalyzing the transfer of a glucose moiety from a UDP-glucose donor to the C-3' of the 19-O-glucose of the Reb J acceptor.
Figure 3B:
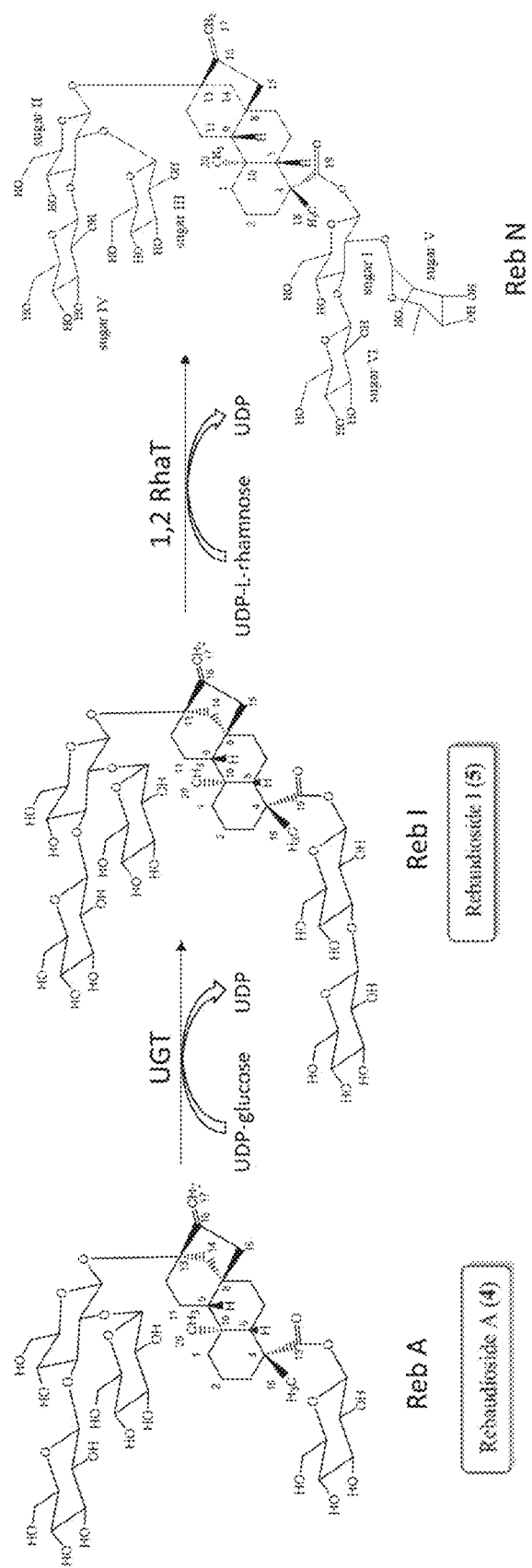
FIG. 3B shows the biosynthetic pathway for the production of Reb I from Reb A using a UGT. Reb I can then be converted to Reb N using a 1,2 RhaT.

The present disclosure relates, in some embodiments, to the production of a steviol glycoside of interest, Reb N, from Reb A using at least one novel UDP-rhamnosyltransferases (RhaT) described herein, which can transfer a rhamnose moiety from UDP-L-rhamnose to a steviol glycoside acceptor in a rhamnosylation reaction. Referring to FIG. 3, the synthetic pathway can involve rebaudioside J as an intermediate (FIG. 3A), or rebaudioside I as an intermediate (FIG. 3B). The subject technology provides, in some embodiments, recombinant polypeptides with UDP glycosyltransferase activities for synthesizing steviol glycosides. In some embodiments, the recombinant polypeptides can have 1,2-19-O-rhamnose glycosylation activity. In some embodiments, the recombinant polypeptides can have 1,3-19-O-glucose glycosylation activity. The recombinant polypeptide of the subject technology is useful for the biosynthesis of steviol glycoside compounds. In the present disclosure, UDP-rhamnosyltransferase (Rha T) refers to an enzyme that transfers a rhamnose sugar moiety from an activated donor molecule (typically UDP-L-rhamnose) to an acceptor steviol glycoside molecule. The 1,2 Rha T refers to an enzymatic activity that transfers a rhamnose moiety from UDP-L-rhamnose to the C-2' of the 19-O-glucose or the 13-O-glucose of steviol glycosides. The 1,2-19-O-rhamnose glycosylation activity refers to an enzymatic activity that transfers a rhamnose moiety to the C-2' of the 19-0 glucose moiety of a steviol glycoside such as rebaudioside A (to produce rebaudioside J) or rebaudioside I (to produce rebaudioside N). The 1,3-19-O-glucose glycosylation activity refers to an enzymatic activity that transfers a glucose moiety to the C-3' of the 19-0 glucose moiety of a steviol glycoside such as rebaudioside J (to produce rebaudioside N) or rebaudioside A (to produce rebaudioside I) (FIG. 3).

Synthetic Biology

Standard recombinant DNA and molecular cloning techniques used here are well known in the art and are described, for example, by Sambrook, J., Fritsch, E. F. and Maniatis, T. MOLECULAR CLONING: A LABORATORY MANUAL, 2nd ed.; Cold Spring Harbor Laboratory: Cold Spring Harbor, N.Y., 1989 (hereinafter "Maniatis"); and by Silhavy, T. J., Bennan, M. L. and Enquist, L. W. EXPERIMENTS WITH GENE FUSIONS; Cold Spring Harbor Laboratory: Cold Spring Harbor, N.Y., 1984; and by Ausubel, F. M. et al., IN CURRENT PROTOCOLS IN MOLECULAR BIOLOGY, published by Greene Publishing and Wiley-Interscience, 1987; (the entirety of each of which is hereby incorporated herein by reference).

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

The disclosure will be more fully understood upon consideration of the following non-limiting Examples. It should be understood that these Examples, while indicating preferred embodiments of the subject technology, are given by way of illustration only. From the above discussion and these Examples, one skilled in the art can ascertain the essential characteristics of the subject technology, and without departing from the spirit and scope thereof, can make various changes and modifications of the subject technology to adapt it to various uses and conditions.

Glycosylation is often considered a ubiquitous reaction controlling the bioactivity and storage of plant natural products. Glycosylation of small molecules is catalyzed by a superfamily of transferases in most plant species that have been studied to date. These glycosyltransferases (GTs) have been classified into over 60 families. Of these, the family of GT enzymes, also known as the UDP glycosyltransferases (UGTs) and UDP-rhamnosyltransferase, transfers sugar moieties to specific acceptor molecules. These are the molecules that transfer such sugar moieties in the steviol glycosides to help create various rebaudiosides. Each of these enzymes have their own activity profile and preferred structure locations where they transfer their activated sugar moieties.

Production Systems

Expression of proteins in prokaryotes is most often carried out in a bacterial host cell with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and, 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such vectors are within the scope of the present disclosure.

In an embodiment, the expression vector includes those genetic elements for expression of the recombinant polypeptide in bacterial cells. The elements for transcription and translation in the bacterial cell can include a promoter, a coding region for the protein complex, and a transcriptional terminator.

A person of ordinary skill in the art will be aware of the molecular biology techniques available for the preparation of expression vectors. The polynucleotide used for incorporation into the expression vector of the subject technology, as described above, can be prepared by routine techniques such as polymerase chain reaction (PCR).

Several molecular biology techniques have been developed to operably link DNA to vectors via complementary cohesive termini. In one embodiment, complementary homopolymer tracts can be added to the nucleic acid molecule to be inserted into the vector DNA. The vector and nucleic acid molecule are then joined by hydrogen bonding between the complementary homopolymeric tails to form recombinant DNA molecules.

In an alternative embodiment, synthetic linkers containing one or more restriction sites provide are used to operably link the polynucleotide of the subject technology to the expression vector. In an embodiment, the polynucleotide is generated by restriction endonuclease digestion. In an embodiment, the nucleic acid molecule is treated with bacteriophage T4 DNA polymerase or *E. coli* DNA polymerase I, enzymes that remove protruding, 3'-single-stranded termini with their 3'-5'-exonucleolytic activities and fill in recessed 3'-ends with their polymerizing activities, thereby generating blunt ended DNA segments. The blunt-ended segments are then incubated with a large molar excess of linker molecules in the presence of an enzyme that can catalyze the ligation of blunt-ended DNA molecules, such as bacteriophage T4 DNA ligase. Thus, the product of the reaction is a polynucleotide carrying polymeric linker sequences at its ends. These polynucleotides are then cleaved with the appropriate restriction enzyme and ligated to an expression vector that has been cleaved with an enzyme that produces termini compatible with those of the polynucleotide.

Alternatively, a vector having ligation-independent cloning (LIC) sites can be employed. The required PCR amplified polynucleotide can then be cloned into the LIC vector without restriction digest or ligation (Aslanidis and de Jong, NUCL. ACID. RES. 18 6069-74, (1990), Haun, et al, BIOTECH-NIQUES 13, 515-18 (1992), which is incorporated herein by reference).

In an embodiment, to isolate and/or modify the polynucleotide of interest for insertion into the chosen plasmid, it is suitable to use PCR. Appropriate primers for use in PCR preparation of the sequence can be designed to isolate the required coding region of the nucleic acid molecule, add restriction endonuclease or LIC sites, place the coding region in the desired reading frame.

In an embodiment, a polynucleotide for incorporation into an expression vector of the subject technology is prepared using PCR using appropriate oligonucleotide primers. The coding region is amplified, whilst the primers themselves become incorporated into the amplified sequence product. In an embodiment, the amplification primers contain restriction endonuclease recognition sites, which allow the amplified sequence product to be cloned into an appropriate vector.

The expression vectors can be introduced into plant or microbial host cells by conventional transformation or transfection techniques. Transformation of appropriate cells with an expression vector of the subject technology is accomplished by methods known in the art and typically depends on both the type of vector and cell. Suitable techniques include calcium phosphate or calcium chloride co-precipitation, DEAE-dextran mediated transfection, lipofection, chemoporation or electroporation.

Successfully transformed cells, that is, those cells containing the expression vector, can be identified by techniques well known in the art. For example, cells transfected with an expression vector of the subject technology can be cultured to produce polypeptides described herein. Cells can be examined for the presence of the expression vector DNA by techniques well known in the art.

The host cells can contain a single copy of the expression vector described previously, or alternatively, multiple copies of the expression vector, In some embodiments, the transformed cell is an animal cell, an insect cell, a plant cell, an algal cell, a fungal cell, or a yeast cell. In some embodiments, the cell is a plant cell selected from the group consisting of: canola plant cell, a rapeseed plant cell, a palm plant cell, a sunflower plant cell, a cotton plant cell, a corn plant cell, a peanut plant cell, a flax plant cell, a sesame plant cell, a soybean plant cell, and a *petunia* plant cell.

Microbial host cell expression systems and expression vectors containing regulatory sequences that direct high-level expression of foreign proteins are well known to those skilled in the art. Any of these could be used to construct vectors for expression of the recombinant polypeptide of the subjection technology in a microbial host cell. These vectors could then be introduced into appropriate microorganisms via transformation to allow for high level expression of the recombinant polypeptide of the subject technology.

Vectors or cassettes useful for the transformation of suitable microbial host cells are well known in the art. Typically, the vector or cassette contains sequences directing transcription and translation of the relevant polynucleotide, a selectable marker, and sequences allowing autonomous replication or chromosomal integration. Suitable vectors comprise a region 5' of the polynucleotide which harbors transcriptional initiation controls and a region 3' of the DNA fragment which controls transcriptional termination. It is preferred for both control regions to be derived from genes homologous to the transformed host cell, although it is to be understood that such control regions need not be derived from the genes native to the specific species chosen as a host.

Initiation control regions or promoters, which are useful to drive expression of the recombinant polypeptide in the desired microbial host cell are numerous and familiar to those skilled in the art. Virtually any promoter capable of driving these genes is suitable for the subject technology including but not limited to CYCI, HIS3, GALI, GALIO, ADHI, PGK, PH05, GAPDH, ADCI, TRPI, URA3, LEU2, ENO, TPI (useful for expression in *Saccharomyces*); AOXI (useful for expression in *Pichia*); and lac, trp, JPL, IPR, T7, tac, and trc (useful for expression in *Escherichia coli*).

Termination control regions may also be derived from various genes native to the microbial hosts. A termination site optionally may be included for the microbial hosts described herein.

In plant cells, the expression vectors of the subject technology can include a coding region operably linked to promoters capable of directing expression of the recombinant polypeptide of the subject technology in the desired tissues at the desired stage of development. For reasons of convenience, the polynucleotides to be expressed may comprise promoter sequences and translation leader sequences derived from the same polynucleotide. 3' non-coding sequences encoding transcription termination signals should also be present. The expression vectors may also comprise one or more introns to facilitate polynucleotide expression.

For plant host cells, any combination of any promoter and any terminator capable of inducing expression of a coding region may be used in the vector sequences of the subject technology. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with an expression vector of the subject technology should be capable of promoting the expression of the vector. High level plant promoters that may be used in the subject technology include the promoter of the small subunit (ss) of the ribulose-1,5-bisphosphate carboxylase for example from soybean (Berry-Lowe et al., J. MOLECULAR AND APP. GEN., 1:483 498 (1982), the entirety of which is hereby incorporated herein to the extent it is consistent herewith), and the promoter of the chlorophyll alb binding protein. These two promoters are known to be light-induced in plant cells (see, for example, GENETIC ENGINEERING OF PLANTS, AN AGRICULTURAL PERSPECTIVE, A. Cashmore, Plenum, N.Y. (1983), pages 29 38; Coruzzi, G. et al., The Journal of Biological CHEMISTRY, 258: 1399 (1983), and Dunsmuir, P. et al., JOURNAL OF MOLECULAR AND APPLIED GENETICS, 2:285 (1983), each of which is hereby incorporated herein by reference to the extent they are consistent herewith).

Precursor Synthesis to Reb J or Reb I

As previously stated steviol glycosides are the chemical compounds responsible for the sweet taste of the leaves of the South American plant *Stevia rebaudiana* (Asteraceae) and in the plant *Rubus chingii* (Rosaceae). These compounds are glycosylated diterpenes. Specifically, their molecules can be viewed as a steviol molecule, with its hydroxyl hydrogen atom replaced by a glucose molecule to form an ester, and a hydroxyl hydrogen with combinations of glucose and rhamnose to form an acetal.

One method of making the compounds of interest in the current disclosure is to take common or inexpensive precursors such as steviol, stevioside, Reb A or rubososide derived chemically or produced via biosynthesis in engineered microbes such as bacteria and/or yeast and to synthesize targeted steviol glycosides through known or inexpensive methods, such as Reb J or Reb I.

Aspects of the present disclosure relate to methods involving recombinantly expressing enzymes in a microbial system capable of producing steviol. In general, such enzymes may include: a copalyl diphosphate synthase (CPS), a kaurene synthase (KS) and a geranylgeranyl diphosphate to synthase (GGPPS) enzyme. This should occur in a microbial strain that expresses an endogenous isoprenoid synthesis pathway, such as the non-mevalonate (MEP) pathway or the mevalonic acid pathway (MVA). In some embodiments, the cell is a bacterial cell, including *E. coli*, or yeast cell such as a *Saccharomyces* cell, *Pichia* cell, or a *Yarrowia* cell. In some embodiments, the cell is an algal cell or a plant cell.

Thereafter, the precursor is recovered from the fermentation culture for use in chemical synthesis. Typically, this is steviol though it can be kaurene, or a steviol glycoside from the cell culture. In some embodiments, the steviol, kaurene and/or steviol glycosides is recovered from the gas phase while in other embodiments, an organic layer or polymeric resin is added to the cell culture, and the kaurene, steviol and/or steviol glycosides is recovered from the organic layer or polymeric resin. In some embodiments, the steviol glycoside is selected from rebaudioside A, rebaudioside B, rebaudioside C, rebaudioside N, rebaudioside E, rebaudioside F, rebaudioside J or dulcoside A. In some embodiments, the terpenoid produced is steviobioside or stevioside. It should also be appreciated that in some embodiments, at least one enzymatic step, such as one or more glycosylation steps, are performed ex vivo.

Part of the disclosure is the production of the Reb J steviol glycoside, which can be subject to further enzymatic conversion to Reb N. In some embodiments, Reb A can be converted to Reb J using a rhamnosyltransferase (RhaT) as described herein, e.g., EU11, EUCP1, HV1, UGT2E-B, or NX114, and a rhamnose donor moiety such as UDP-rhamnose. In some embodiments, the biosynthesis for the conversion of microbially produced steviol to a desired steviol glycoside (e.g., Reb N) occurs when the diterpenoid steviol is converted to rubusoside and stevioside using multi-step chemical assembly of sugar moiety into the steviol backbone utilizing specifically identified and/or modified enzymes created by the inventors. In addition to the EU11, EUCP1, HV1 and UGT76G1 enzymes utilized herein other enzymes were identified that can work to deliver these steviol rebaudiosides as well. For example, it was determined that other UGT enzymes (CP1 and CP2 respectively—amino acid sequences at SEQ ID NO: 11 and SEQ ID NO: 13) and the UGT76G1-AtSUS1 fusion enzyme can convert Reb J to Reb N.

Part of the disclosure is the production of the Reb I steviol glycoside from Reb A, which can be subject to further enzymatic conversion to Reb N. In some embodiments, the biosynthesis for the conversion of Reb A to Reb I occurs by reacting Reb A with a glucose donor moiety in the presence of a recombinant polypeptide having glucosyltransferase activity. In some embodiments, the glucose donor moiety is generated in situ. In some embodiments, the glucose donor moiety is added to the reaction. In some embodiments, the recombinant polypeptide having glucosyltransferase activity further comprises sucrose synthase activity. For example, in some embodiments, an enzyme identified as UGT76G1 (SEQ ID NO: 7) can convert Reb A to Reb I. In some embodiments, other UGT enzymes (e.g., CP1 and CP2 respectively—amino acid sequences at SEQ ID NO: 11 and SEQ ID NO: 13) can convert Reb A to Reb I. In some embodiments, the UCT76G1-AtSUS1 fusion enzyme can convert Reb A to Reb I. In some embodiments, Reb I can be converted to Reb N using a rhamnosyltransferase (RhaT) as described herein, e.g., EU11, EUCP1, HV1, UGT2E-B, or NX114, and a rhamnose donor moiety such as UDP-rhamnose.

Biosynthesis of Steviol Glycosides

As described herein, the recombinant polypeptides of the present technology have UDP-glycosyltransferase (UDP-gluocosytransferase and/or UDP-rhamnosyltransferase) activities and are useful for developing biosynthetic methods for preparing steviol glycosides that are either not present in nature or typically of low abundance in natural sources, such as rebaudioside J, rebaudioside I and rebaudioside N, respectively. The recombinant polypeptides of the present technology have UDP-glycosyltransferase activities, are useful for developing biosynthetic methods for preparing steviol glycosides, such as rebaudioside J or rebaudioside I, and reaching the synthetic production of rebaudioside N.

The substrate or starting steviol glycoside composition, can be any natural or synthetic compound capable of being converted into a steviol glycoside compound in a reaction catalyzed by one or more UDP-rhamnosyltransferases. For example, the substrate can be natural *stevia* extract, steviol, steviol-13-O-glucoside, steviol-19-O-glucoside, steviol-1,2-bioside, rubusoside, stevioside, rebaudioside A, rebaudioside B or rebaudioside I. The substrate can be a pure compound or a mixture of different compounds. Preferably, the substrate includes a compound selected from the group consisting of rubusoside, stevioside, steviol, rebaudioside A, rebaudioside B, rebaudioside J and combinations thereof.

The method described herein also provides a coupling reaction system in which the recombinant peptides described herein can function in combination with one or more additional enzymes to improve the efficiency or modify the outcome of the overall biosynthesis of steviol glycoside compounds. For example, the additional enzymes may regenerate the UDP-rhamnose needed for the rhamnosylation reaction (see e.g., Pei et al., "Construction of a novel UDP-rhamnose regeneration system by a two-enzyme reaction system and application in glycosylation of flavonoid," Biochemical Engineering Journal, 139: 33-42 (2018), the entire disclosure of which is incorporated herein by reference) and the additional enzyme may regenerate the UDP-glucose needed for the glycosylation reaction by converting the UDP produced from the glycosylation reaction back to UDP-glucose (using, for example, sucrose as a donor of the glucose residue), thus improving the efficiency of the glycosylation reaction.

In another embodiment, the method of the subject technology further includes incubating a recombinant and novel UDP-rhamnosyltransferase (RhaT) according to the current disclosure with the substrate and one or more additional recombinant polypeptides (e.g., a recombinant UGT) described herein. The recombinant UGT can catalyze a different glycosylation reaction than the one catalyzed by the recombinant polypeptide of the subject technology leading to the production of Reb J and Reb N.

Suitable UDP-glycosyltransferase includes any UGT known in the art as capable of catalyzing one or more reactions in the biosynthesis of steviol glycoside compounds, such as UGT85C2, UGT74G1, UGT76G1, or the functional homologs thereof.

In some embodiments, in the in vitro method of the subject technology, UDP-glucose and/or UDP-L-rhamnose can be included in the buffer at a concentration of from about 0.2 mM to about 5 mM, preferably from about 0.5 mM to about 2 mM, more preferably from about 0.7 mM to about 1.5 mM. In an embodiment, when a recombinant sucrose synthase is included in the reaction, sucrose is also included in the buffer at a concentration of from about 100 mM to about 500 mM, preferably from about 200 mM to about 400 mM, more preferably from about 250 mM to about 350 mM.

In some embodiments, in the in vitro method of the subject technology, the weight ratio of the recombinant polypeptide to the substrate, on a dry weight basis, is from about 1:100 to about 1:5, preferably from about 1:50 to about 1:10, more preferably from about 1:25 to about 1:15.

In some embodiments, the reaction temperature of the in vitro method is from about 20° C. to about 40° C., suitably from 25° C. to about 37° C.

One skilled in the art will recognize that the steviol glycoside composition produced by the method described herein can be further purified and mixed with other steviol glycosides, flavors, or sweeteners to obtain a desired flavor or sweetener composition. For example, a composition enriched with Reb J or Reb N produced as described herein can be mixed with a natural *stevia* extract containing rebaudioside A as the predominant steviol glycoside, or with other synthetic or natural steviol glycoside products to make a desired sweetener composition. Alternatively, a substantially purified steviol glycoside (e.g., rebaudioside J and rebaudioside N) obtained from the methods described herein can be combined with other sweeteners, such as sucrose, maltodextrin, aspartame, sucralose, neotame, acesulfame potassium, and saccharin. The amount of steviol glycoside relative to other sweeteners can be adjusted to obtain a desired taste, as known in the art. The steviol glycoside described herein (including rebaudioside N, rebaudioside I, rebaudioside J, or a combination thereof) can be included in food products (such as beverages, soft drinks, ice cream, dairy products, confectioneries, cereals, chewing gum, baked goods, etc.), dietary supplements, medical nutrition, as well as pharmaceutical products.

Analysis of Sequence Similarity Using Identity Scoring

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this disclosure "percent identity" may also be determined using BLASTX version 2.0 for translated nucleotide sequences and BLASTN version 2.0 for polynucleotide sequences.

The percent of sequence identity is preferably determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, JOURNAL OF MOLECULAR BIOLOGY 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, ADVANCES IN APPLIED MATHEMATICS, 2:482-489, 1981, Smith et al., NUCLEIC ACIDS RESEARCH 11:2205-2220, 1983). The percent identity is most preferably determined using the "Best Fit" program.

Useful methods for determining sequence identity are also disclosed in the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; Altschul et al., J. MOL. BIOL. 215:403-410 (1990); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As used herein, the term "substantial percent sequence identity" refers to a percent sequence identity of at least about 70% sequence identity, at least about 80% sequence identity, at least about 85% identity, at least about 90% sequence identity, or even greater sequence identity, such as about 98% or about 99% sequence identity. Thus, one embodiment of the disclosure is a polynucleotide molecule that has at least about 70% sequence identity, at least about 80% sequence identity, at least about 85% identity, at least about 90% sequence identity, or even greater sequence identity, such as about 98% or about 99% sequence identity with a polynucleotide sequence described herein. Polynucleotide molecules that have the activity of the 1,2 RhaT and UGT enzymes of the current disclosure are capable of directing the production of a variety of steviol glycosides and have a substantial percent sequence identity to the polynucleotide sequences provided herein and are encompassed within the scope of this disclosure.

Identity and Similarity

Identity is the fraction of amino acids that are the same between a pair of sequences after an alignment of the sequences (which can be done using only sequence information or structural information or some other information, but usually it is based on sequence information alone), and similarity is the score assigned based on an alignment using some similarity matrix. The similarity index can be any one of the following BLOSUM62, PAM250, or GONNET, or any matrix used by one skilled in the art for the sequence alignment of proteins.

Identity is the degree of correspondence between two sub-sequences (no gaps between the sequences). An identity of 25% or higher implies similarity of function, while 18-25% implies similarity of structure or function. Keep in mind that two completely unrelated or random sequences (that are greater than 100 residues) can have higher than 20% identity. Similarity is the degree of resemblance between two sequences when they are compared. This is dependent on their identity.

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

Although the foregoing invention has been described in some detail by way of illustration and example for purposes of understanding, it will be apparent to those skilled in the art that certain changes and modifications may be practiced. Therefore, the description and examples should not be construed as limiting the scope of the invention, which is delineated by the appended claims.

EXAMPLES

Example 1: Enzymatic Activity Screening of 1,2 RhaT Enzymes

Phylogenetic, gene cluster, and protein BLAST analyses were used to identify candidate 1,2 RhaT transferase genes. Full-length DNA fragments of candidate 1,2 RhaT transferase genes were optimized and synthesized according to the codon preference of *E. coli* (Genscript, NJ). The synthesized DNA fragments were cloned into a bacterial expression vector pETite N-His SUMO Kan Vector (Lucigen).

Each expression construct was transformed into *E. coli* BL21 (DE3), which was subsequently grown in LB media containing 50 µg/mL kanamycin at 37° C. until reaching an $OD_{600}$ of 0.8-1.0. Protein expression was induced by adding 1 mM of isopropyl β-D-1-thiogalactopyranoside (IPTG), and the culture was incubated further at 16° C. for 22 hours. Cells were harvested by centrifugation (3,000×g; 10 min; 4° C.). The cell pellets were collected and were either used immediately or stored at −80° C.

The cell pellets typically were re-suspended in lysis buffer (50 mM potassium phosphate buffer, pH 7.2, 25 µg/ml lysozyme, 5 µg/ml DNase I, 20 mM imidazole, 500 mM NaCl, 10% glycerol, and 0.4% Triton X-100). The cells were disrupted by sonication at 4° C., and the cell debris was clarified by centrifugation (18,000×g; 30 min). The supernatant was loaded to an equilibrated (equilibration buffer: 50 mM potassium phosphate buffer, pH 7.2, 20 mM imidazole, 500 mM NaCl, 10% glycerol) Ni-NTA (Qiagen) affinity column. After loading of the protein samples, the column was washed with equilibration buffer to remove unbound contaminant proteins. The His-tagged 1,2 RhaT recombinant polypeptides were eluted with an equilibration buffer containing 250 mM of imidazole.

The purified candidate 1,2 RhaT recombinant polypeptides were assayed for UDP-rhamnosyltransferase activity. Typically, the recombinant polypeptide (20-50 µg) was tested in a 200 µl in vitro reaction system. The reaction system contains 50 mM of potassium phosphate buffer, pH 7.2, 3 mM of $MgCl_2$, 0.25-1 mg/ml of rebaudioside A and UDP-L-rhamnose. The reaction was performed at 30-37° C. and terminated by adding 1-butanol.

The product samples were extracted three times with 200 µL of 1-butanol. The pooled fraction was dried and dissolved in 100 µL of 80% methanol for high-performance liquid chromatography (HPLC) analysis.

HPLC analysis was performed using a Dionex UPLC ultimate 3000 system (Sunnyvale, Calif.), including a quaternary pump, a temperature controlled column compartment, an auto sampler and a UV absorbance detector. A Synergi Hydro-RP column (Phenomenex) with guard column was used for the characterization of steviol glycosides in the pooled samples. The detection wavelength used in the HPLC analysis was 210 nm.

After activity screening, several 1,2 RhaT enzymes having UDP-rhamnosyltransferase activity were identified for bioconversion of Reb A to Reb J.

Example 2: Enzymatic Bioconversion of Reb A to Reb J

The biosynthesis of rebaudioside J involves glucosylation and rhamnosylation of the aglycone steviol. Specifically, Reb J can be produced by rhamnosylation of the C-2' of the 19-O-glucose of Reb A, i.e., via a 1,2 rhamnosylation (FIG. 3).

Figure 4:
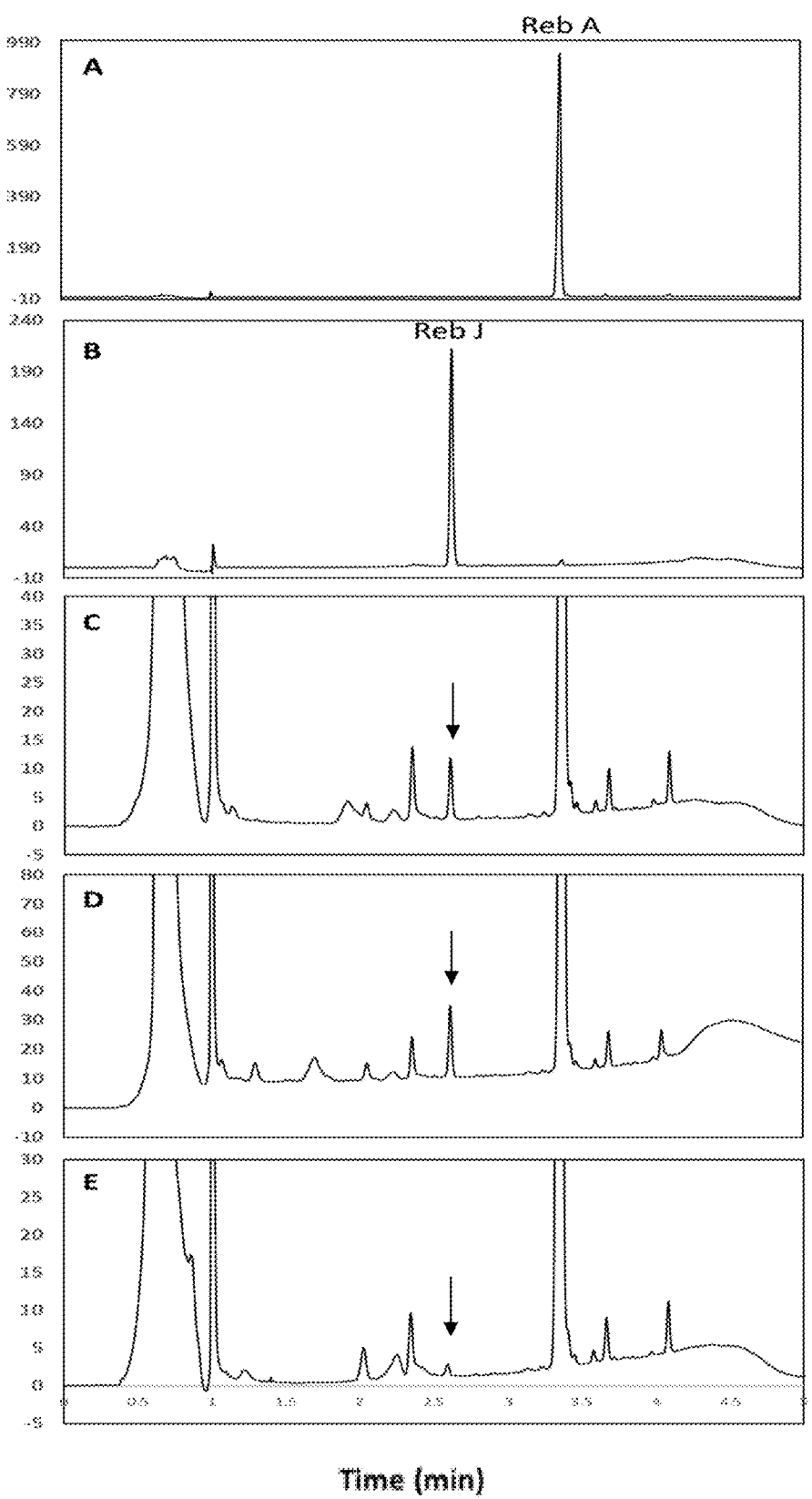
FIG. 4 shows the in vitro production of Reb J from Reb A as catalyzed by selected 1,2 RhaT enzymes via HPLC analysis. Panel A shows the retention time of a Reb A standard. Panel B shows the retention time of a Reb J standard. Panel C shows the retention times of the products obtained from a reaction system catalyzed by EU11 (SEQ ID NO: 1) using Reb A as the substrate. Panel D shows the retention times of the products obtained from a reaction system catalyzed by EUCP1 (SEQ ID NO: 3) using Reb A as the substrate. Panel E shows the retention times of the products obtained from a reaction system catalyzed by HV1 (SEQ ID NO: 5) using Reb A as the substrate. Arrows indicate the presence of Reb J.
Figure 5:
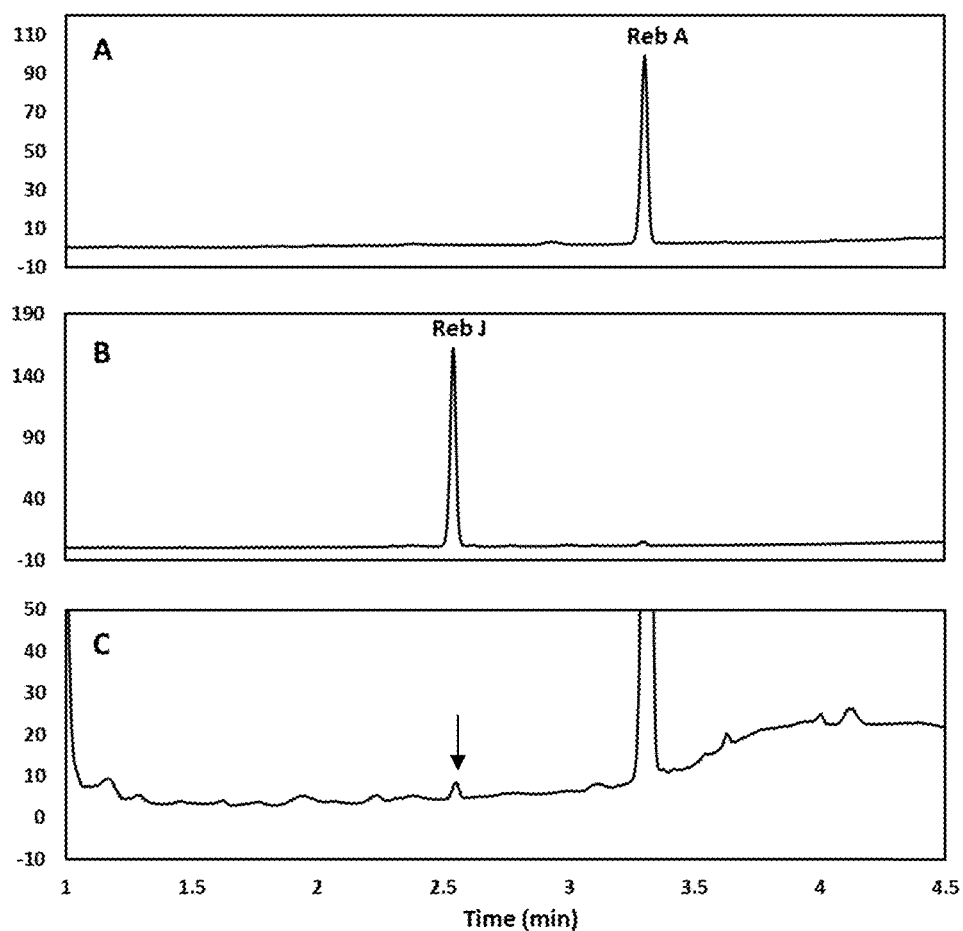
FIG. 5 shows the in vitro production of Reb J from Reb A as catalyzed by UGT2E-B via HPLC analysis. Panel A shows the retention time of a Reb A standard. Panel B shows the retention time of a Reb J standard. Panel C shows the retention times of the products obtained from a reaction system catalyzed by UGT2E-B (SEQ ID NO: 9) using Reb A as the substrate. The arrow indicates the presence of Reb J.
Figure 6:
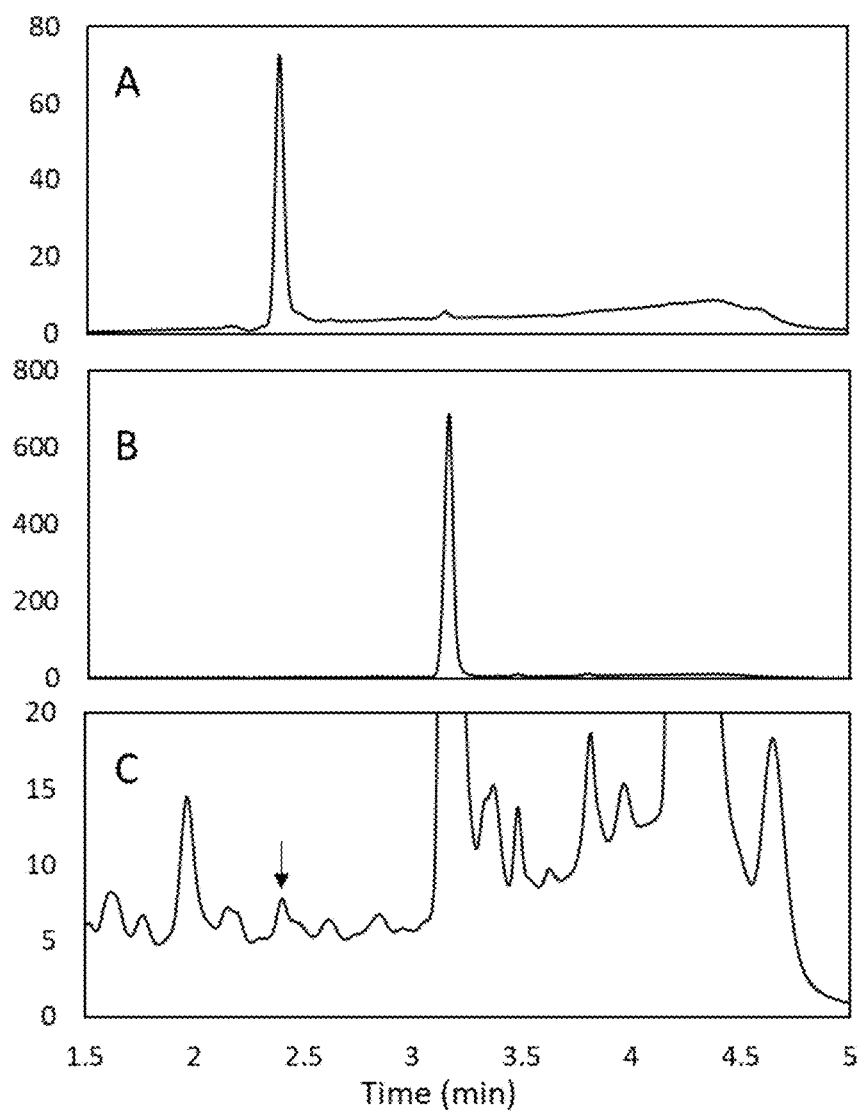
FIG. 6 shows the in vitro production of Reb J from Reb A as catalyzed by NX114 via HPLC analysis. Panel A shows the retention time of a Reb J standard. Panel B shows the retention time of a Reb A standard. Panel C shows the retention times of the products obtained from a reaction system catalyzed by NX114 (SEQ ID NO: 19) using Reb A as the substrate. The arrow indicates the presence of Reb J.

FIGS. 4-6 compare the retention times of Reb A and Reb J standards as analyzed by HPLC against the retention times of the reaction products obtained from the rhamnosylation reaction catalyzed by the candidate 1,2 RhaT enzymes.

It has been reported that EU11, EUCP1 and HV1 have glucosylation activity and are capable of transferring a glucose moiety from UDP-glucose to steviol glycosides, producing compounds such as stevioside, rebaudioside KA, rebaudioside E, rebaudioside D, rebaudioside V, and rebaudioside D3 etc.

As shown in FIGS. 4(C)-4(E), Reb A was converted into Reb J in reaction systems catalyzed by EU11 (SEQ ID NO: 1), a circular permutation of EU11 designated herein as EUCP1 (SEQ ID NO: 3), and HV1 (SEQ ID NO: 5), respectively, demonstrating that in addition to glucosylation activity, these enzymes also have 1,2 rhamnosyltranferase activity. EUCP1 was found to have higher 1,2 rhamnosyltranferase activity than EU11, while EU11 showed much higher 1,2 rhamnosyltranferase activity than HV1.

FIG. 5 shows that Reb A was converted into Reb J in a reaction system catalyzed by UGT2E-B (SEQ ID NO: 9). FIG. 6 shows that Reb A was converted into Reb J in a reaction system catalyzed by NX114 (SEQ ID NO: 19).

Collectively, these data demonstrate that each of the enzymes EU11, EUCP1, HV1, UGT2E-B, and NX114 exhibits 1,2 RhaT activity and is capable of transferring a rhamnose moiety from a UDP-L-rhamnose donor to the C-2' of the 19-O-glucose moiety of Reb A in an a 1,2 rhamnosylation reaction, thereby producing Reb J.

Example 3: Confirmation of Reb J Production by LC-MS Analysis

To confirm the identity of the compounds produced in the reactions catalyzed by the 1,2 RhaT candidate enzymes, LC-MS analyses were performed using a Synergy Hydro-RP column. Mobile phase A was 0.1% formic acid in water, and mobile phase B was 0.1% formic acid in acetonitrile. The flow rate was 0.6 ml/min. Mass spectrometry analysis of the samples was done on the Q Exactive Hybrid Quadrupole-Orbitrap Mass Spectrometer (Thermo Fisher Scientific) with an optimized method in positive ion mode.

LC-MS analysis confirmed that the products obtained from the rhamsylation reaction catalyzed by EU11, EUCP1, HV1, UGT2E-B, and NX114, respectively, have the same mass [(M+Na$^+$) 1135.48 m/z] and retention time (2.61 min) as the Reb J standard.

Example 4: Enzymatic Bioconversion of Reb J to Reb N

Referring again to FIG. 3, Reb N can be produced by glucosylation of the C-3' of the 19-O-glucose of Reb J in a β 1,3 glucosylation reaction.

To identify suitable UGTs for bioconversion of Reb J to Reb N, enzyme candidates were assayed using the Reb J products obtained from Example 1.

After terminating Reb J production by heating (to denature the 1,2 RhaT enzymes), UGT candidate enzymes (5 µg of enzymes per 200 µl of reaction mixture) and 1 mM of UDP-glucose was added into the reaction mixture. The glucosylation reaction was performed at 37° C. for 3 hours.

Figure 7:
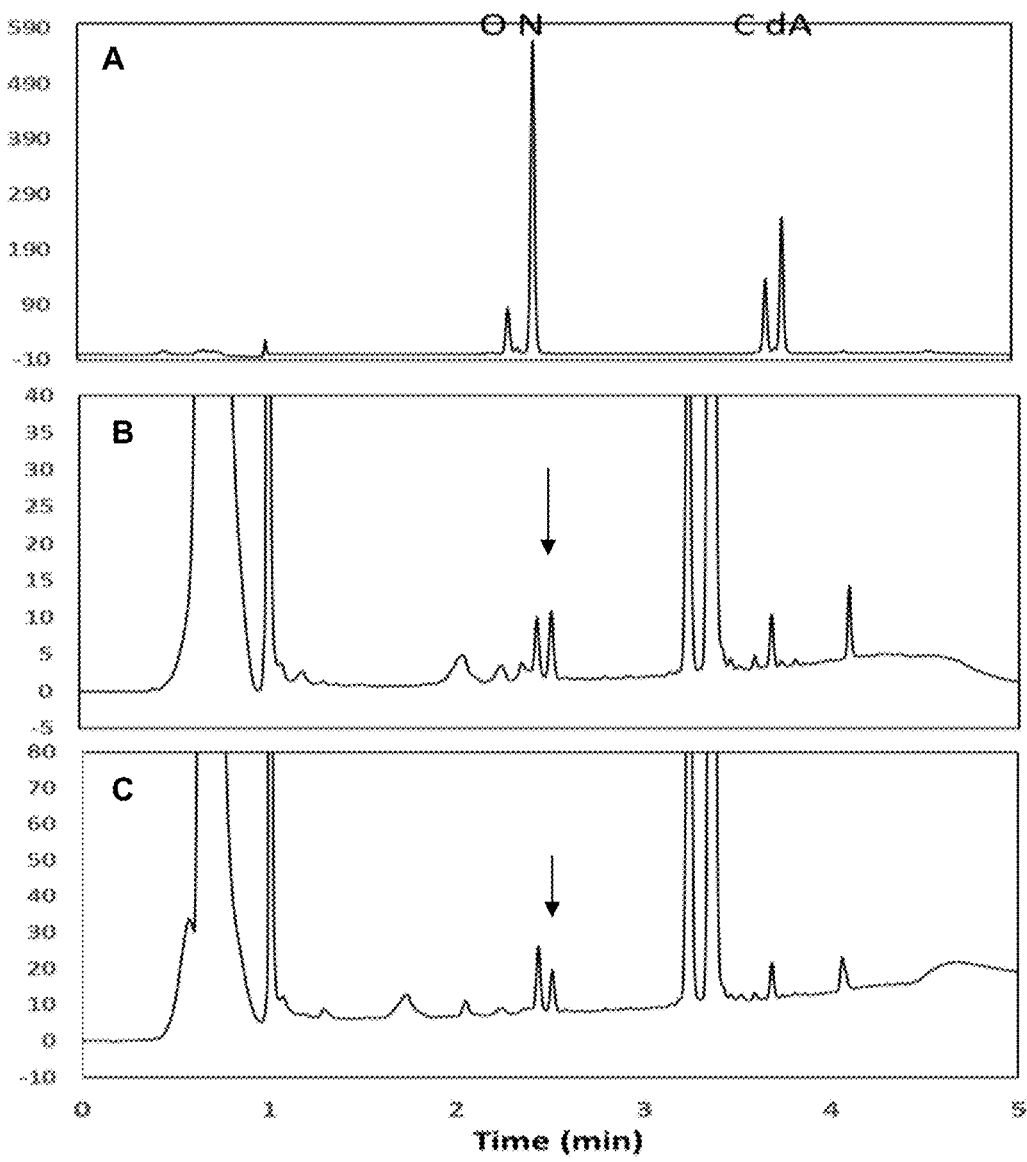
FIG. 7 shows the in vitro production of Reb N from Reb J as catalyzed by UGT76G1 via HPLC analysis. Panel A shows the retention time of various steviol glycoside standards include rebaudioside O, Reb N, rebaudioside C, and dulcoside A. Panel B shows the retention time of the products obtained from a reaction system catalyzed by UGT76G1 (SEQ ID NO: 7) using Reb J obtained from a EU11-catalyzed reaction. Panel C shows the retention time of the products obtained from a reaction system catalyzed by UGT76G1 (SEQ ID NO: 7) using Reb J obtained from a EUCP1-catalyzed reaction. Arrows indicate the presence of Reb N.

FIG. 7 compares the retention times of Reb O, Reb N, Reb C, and dulcoside A ("dA") standards as analyzed by HPLC against the retention times of the reaction products obtained from the glucosylation reaction catalyzed by UGT76G1 (SEQ ID NO: 7) using the Reb J products obtained from the EU11-catalyzed (FIG. 7(B)) and EUCP1-catalyzed (FIG. 7(C)) reaction systems of Example 1, respectively, as the substrate. As shown in FIGS. 7(B) and 7(C), Reb J was converted to Reb N in the presence of UGT76G1.

Based on the structure of UGT76G1, the inventors were able to design CP1 (SEQ ID NO: 11) which is a circular permutation of UGT76G1, CP2 (SEQ ID NO: 13) which is a mutant of CP1 and was generated by inserting a linker between the C-terminal and N-terminal of CP1, and a fusion enzyme GS (SEQ ID NO: 15) that includes a UDP-glycosyltransferase (UGT) domain, UGT76G1, coupled to a sucrose synthase (SUS) domain, AtSUS1.

Figure 8:
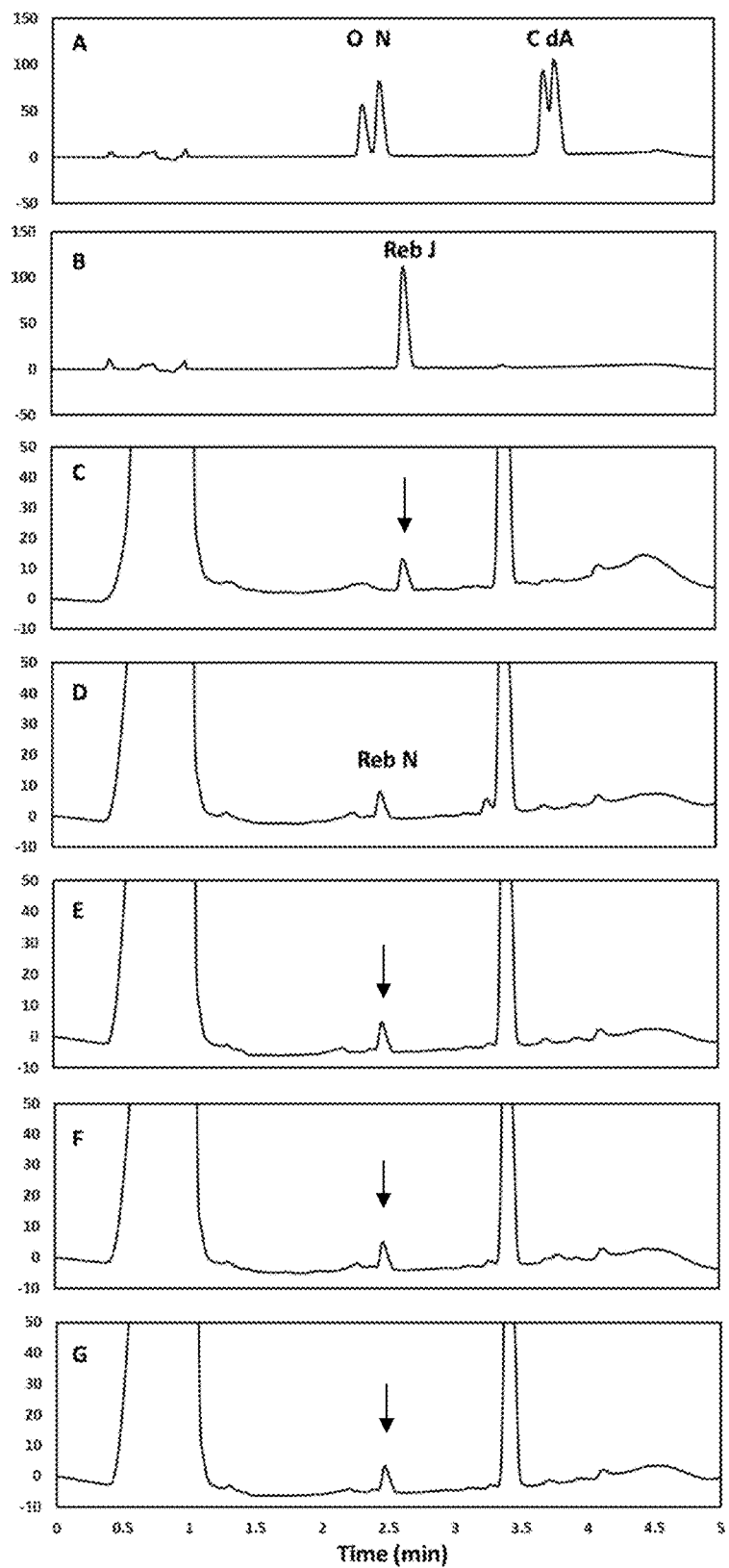
FIG. 8 shows the in vitro production of Reb N from Reb J as catalyzed by selected UGT enzymes via HPLC analysis. Panel A shows the retention time of various steviol glycoside standards include rebaudioside O, Reb N, rebaudioside C, and dulcoside A. Panel B shows the retention time of a Reb J standard. Panel B shows the retention time of the Reb J intermediate obtained from a EUCP1-catalyzed reaction (as indicated by the arrow). Panel D shows the retention time of the Reb N product obtained from a reaction system catalyzed by UGT76G1 (SEQ ID NO: 7) using the Reb J intermediate shown in Panel B. Panel E shows the retention time of the Reb N product obtained from a reaction system catalyzed by CP1 (SEQ ID NO: 11) using the Reb J intermediate shown in Panel B (as indicated by the arrow). Panel F shows the retention time of the Reb N product obtained from a reaction system catalyzed by CP2 (SEQ ID NO: 13) using the Reb J intermediate shown in Panel B (as indicated by the arrow). Panel G shows the retention time of the Reb N product obtained from a reaction system cata-lyzed by fusion enzyme GS (SEQ ID NO: 15) using the Reb J intermediate shown in Panel B (as indicated by the arrow).

Referring to FIG. 8, FIG. 8(A) shows the retention time of the Reb J standard. FIG. 8(B) confirms the bioconversion of Reb A into Reb J as catalyzed by EUCP1. Using the Reb J product obtained from the EUCP1-catalyzed reaction as the substrate, UGT76G1, CP1, CP2, and GS were assayed for their glucosylation activity to convert Reb J into Reb N. Comparing against FIG. 8(C) which shows the retention time of the Reb N standard, FIGS. 8(D), 8(E), 8(F), and 8G demonstrate that each of the UGT76G1, CP1, CP2, and GS enzymes is capable of transferring a glucose moiety from UDP-glucose to the C-3' of the 19-O-glucose of Reb J in a β 1,3 glucosylation reaction, thereby producing Reb N.

To evaluate further the activity of a UGT-SUS fusion enzyme in the bioconversion of Reb J to Reb N, assays were performed in the presence of UDP and sucrose but without UDP-glucose using the following enzymatic systems: (1) UGT76G1 (SEQ ID NO: 7) by itself, (2) addition of both a UDP-glycosyltransferase UGT76G1 (SEQ ID NO: 7) and a sucrose synthase AtSUS1 (SEQ ID NO: 17), and (3) fusion enzyme GS (SEQ ID NO: 15) including UDP-glycosyltransferase (UGT) domain, UGT76G1, coupled to a sucrose synthase (SUS) domain, AtSUS1, which has both UDP-glycosyltransferase activity and sucrose synthase activity.

Figure 9:
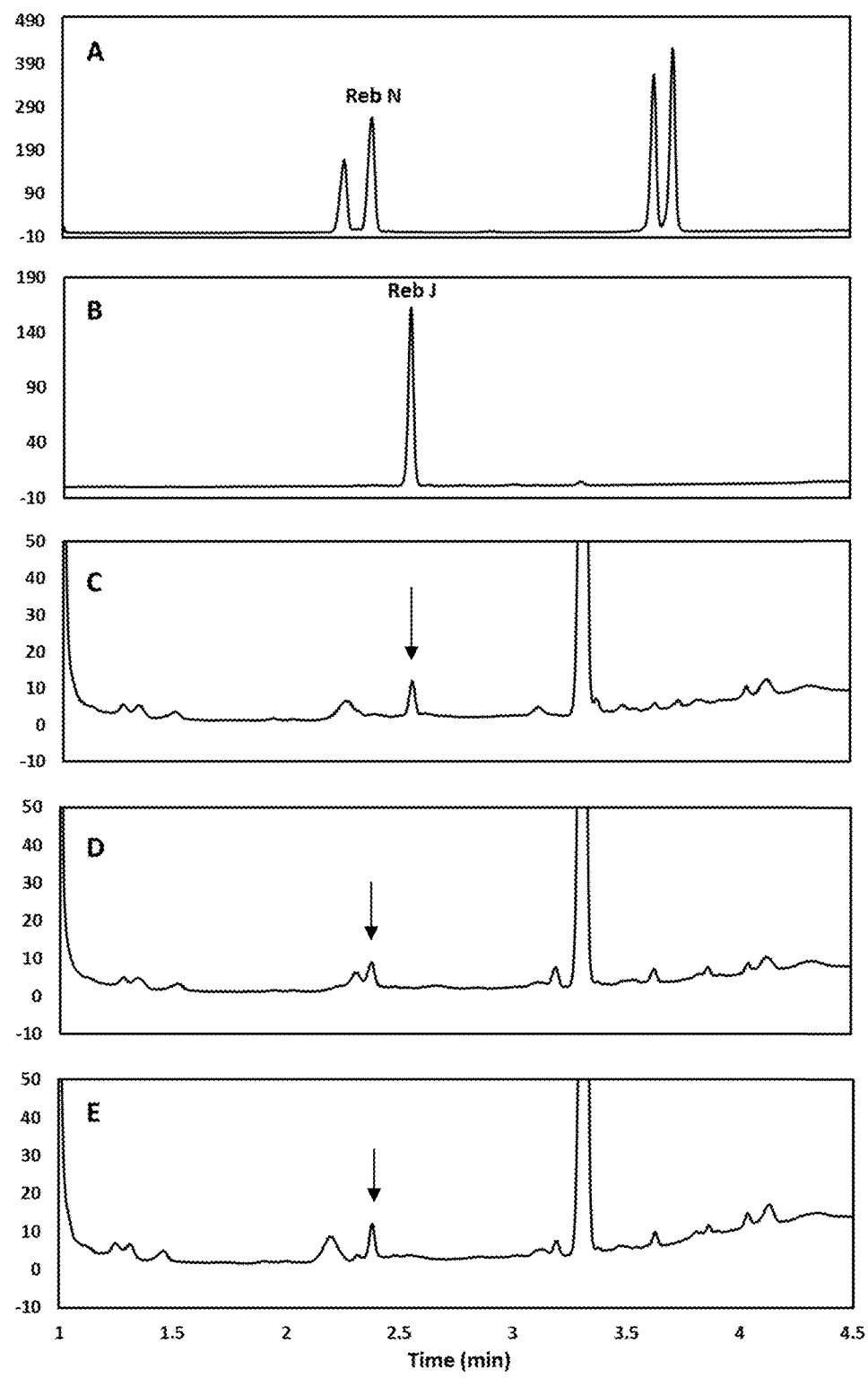
FIG. 9 shows the in vitro production of Reb N from Reb J in the presence of UDP and sucrose as catalyzed by selected UGT enzymes via HPLC analysis. Panel A shows the retention time of a Reb N standard. Panel B shows the retention time of a Reb J standard. Panel C shows the retention time of the product obtained from a UGT76G1-catalyzed reaction. No Reb N production is observed. The arrow indicates the presence of Reb J. Panel D shows the retention time of the product obtained from a reaction system catalyzed by both UGT76G1 and AtSUS1 (SEQ ID NO: 17). Arrow indicates the presence of Reb N. Panel E shows the retention time of the product obtained from a reaction system catalyzed by fusion enzyme GS (SEQ ID NO: 15). Arrow indicates the presence of Reb N.

As shown in FIG. 9(C), UGT76G1 is unable to convert Reb J to Reb N when only UDP and sucrose are present in the reaction system. On the other hand, by using a catalytic system including both a UGT enzyme (e.g., UGT76G1) and an SUS enzyme (e.g., AtSUS1), the SUS enzyme was able to generate UDP-glucose from UDP and sucrose, and the UGT enzyme was able to transfer the glucose moiety from UDP-glucose to Reb J, thereby producing Reb N (FIG. 9(D)). Similarly, the fusion enzyme GS was able to produce Reb N from Reb J (FIG. 9(E)), indicating that the fusion enzyme has sucrose synthase activity and was able to generate UDP-glucose from UDP and sucrose. Additionally, the fusion enzyme GS was found to have higher enzymatic activity (more Reb N was produced) compared to the reaction system where UGT76G1 and AtSUS1 are present as individual enzymes.

Example 5: Confirmation of Reb N Production by LC-MS Analysis

To confirm further the identity of the compounds produced in the reactions catalyzed by the UGT enzymes, LC-MS analyses were performed using a Synergy Hydro-RP column. Mobile phase A was 0.1% formic acid in water, and mobile phase B was 0.1% formic acid in acetonitrile. The flow rate was 0.6 ml/min. Mass spectrometry analysis of the samples was done on the Q Exactive Hybrid Quadrupole-Orbitrap Mass Spectrometer (Thermo Fisher Scientific) with an optimized method in positive ion mode.

LC-MS analysis confirmed that the products obtained from the glucosylation reaction catalyzed by UGT76G1, CP1, CP2, and GS, respectively, using Reb J (produced from the rhamnosylation reaction catalyzed by EU11/EUCP1/HV1/UGT2E-B/NX114 as described in Example 1) as the substrate, have the same mass [(M+Na$^+$) 1297.53 m/z] and retention time (2.43 min) as the Reb N standard.

Sequences of Interest:

Sequences:

```
EU11: Amino Acid Sequence
                                             (SEQ ID NO: 1)
MDSGYSSSYAAAAGMHVVICPWLAFGHLLPCLDLAQRLASRGHRVSFVSTPR

NISRLPPVRPALAPLVAFVALPLPRVEGLPDGAESTNDVPHDRPDMVELHRRAF

DGLAAPFSEFLGTACADWVIVDVFHHWAAAAALEHKVPCAMMLLGSAHMIA

SIADRRLERAETESPAAAGQGRPAAAPTFEVARMKLIRTKGSSGMSLAERFSLT

LSRSSLVVGRSCVEFEPETVPLLSTLRGKPITFLGLMPPLHEGRREDGEDATVR

WLDAQPAKSVVYVALGSEVPLGVEKVHELALGLELAGTRFLWALRKPTGVSD

ADLLPAGFEERTRGRGVVATRWVPQMSILAHAAVGAFLTHCGWNSTIEGLMF

GHPLIMLPIFGDQGPNARLIEAKNAGLQVARNDGDGSFDREGVAAAIRAVAVE

EESSKVFQAKAKKLQEIVADMACHERYIDGFIQQLRSYKD

EU11: DNA Sequence
                                             (SEQ ID NO: 2)
ATGGATTCGGGTTACTCTTCCTCCTATGCGGCGGCTGCGGGTATGCACGTTG

TTATCTGTCCGTGGCTGGCTTTTGGTCACCTGCTGCCGTGCCTGGATCTGGC

ACAGCGTCTGGCTTCACGCGGCCATCGTGTCAGCTTCGTGTCTACCCCGCGC

AATATTTCGCGTCTGCCGCCGGTTCGTCCGGCACTGGCTCCGCTGGTTGCAT

TTGTCGCTCTGCCGCTGCCGCGCGTGGAAGGTCTGCCGGATGGTGCGGAAA

GTACCAACGACGTGCCGCATGATCGCCCGGACATGGTTGAACTGCACCGTC

GTGCATTCGATGGTCTGGCAGCACCGTTTTCCGAATTTCTGGGTACGGCGTG

CGCCGATTGGGTGATCGTTGACGTCTTTCATCACTGGGCGGCGGCGGCGGC

GCTGGAACATAAAGTTCCGTGTGCAATGATGCTGCTGGGCTCAGCTCACAT

GATTGCGTCGATCGCAGACCGTCGCCTGGAACGTGCAGAAACCGAAAGTCC

GGCTGCGGCCGGCCAGGGTCGCCCGGCAGCTGCGCCGACCTTCGAAGTGGC

CCGCATGAAACTGATTCGTACGAAAGGCAGCTCTGGTATGAGCCTGGCAGA

ACGCTTTAGTCTGACCCTGTCCCGTAGTTCCCTGGTGGTTGGTCGCAGTTGC

GTTGAATTTGAACCGGAAACCGTCCCGCTGCTGTCCACGCTGCGTGGTAAA

CCGATCACCTTTCTGGGTCTGATGCCGCCGCTGCATGAAGGCCGTCGCGAA

GATGGTGAAGACGCAACGGTGCGTTGGCTGGATGCACAGCCGGCTAAAAG

CGTCGTGTATGTCGCCCTGGGCTCTGAAGTGCCGCTGGGTGTGGAAAAAGT

TCACGAACTGGCACTGGGCCTGGAACTGGCTGGCACCCGCTTCCTGTGGGC

ACTGCGTAAACCGACGGGTGTGAGCGATGCGGACCTGCTGCCGGCCGGTTT

TGAAGAACGTACCCGCGGCCGTGGTGTTGTCGCAACGCGTTGGGTCCCGCA

AATGAGCATTCTGGCGCATGCCGCAGTGGGCGCCTTTCTGACCCACTGTGG

TTGGAACAGCACGATCGAAGGCCTGATGTTTGGTCACCCGCTGATTATGCT

GCCGATCTTCGGCGATCAGGGTCCGAACGCACGTCTGATTGAAGCGAAAA

TGCCGGCCTGCAAGTTGCGCGCAACGATGGCGACGGTTCTTTCGACCGTGA

GGGTGTGGCTGCGGCCATTCGCGCAGTGGCTGTTGAAGAAGAATCATCGAA

AGTTTTTCAGGCGAAAGCCAAAAAACTGCAAGAAATCGTCGCGGATATGGC
```

-continued

```
CTGCCACGAACGCTACATTGATGGTTTCATTCAGCAACTGCGCTCCTACAA

AGACTAA
```

EUCP1: Amino Acid sequence
(SEQ ID NO: 3)
```
MGSSGMSLAERFSLTLSRSSLVVGRSCVEFEPETVPLLSTLRGKPITFLGLMPPLHEGRR

EDGEDATVRWLDAQPAKSVVYVALGSEVPLGVEKVHELALGLELAGTRFLWALRKP

TGVSDADLLPAGFEERTRGRGVVATRWVPQMSILAHAAVGAFLTHCGWNSTIEGLMF

GHPLIMLPIFGDQGPNARLIEAKNAGLQVARNDGDGSFDREGVAAAIRAVAVEEESSK

VFQAKAKKLQEIVADMACHERYIDGFIQQLRSYKDDSGYSSSYAAAAGMHVVICPWL

AFGHLLPCLDLAQRLASRGHRVSFVSTPRNISRLPPVRPALAPLVAFVALPLPRVEGLP

DGAESTNDVPHDRPDMVELHRRAFDGLAAPFSEFLGTACADWVIVDVFHHWAAAAA

LEHKVPCAMMLLGSAHMIASIADRRLERAETESPAAAGQGRPAAAPTFEVARMKLIR

TK
```

EUCP1: DNA Sequence
(SEQ ID NO: 4)
```
ATGGGTAGCTCGGGCATGTCCCTGGCGGAACGCTTTTCGCTGACGCTGAGTCGCTC

ATCCCTGGTTGTTGGTCGCAGTTGTGTTGAATTTGAACCGGAAACCGTTCCGCTGC

TGTCTACGCTGCGCGGCAAACCGATTACCTTCCTGGGTCTGATGCCGCCGCTGCAT

GAAGGCCGTCGCGAAGATGGTGAAGACGCCACGGTGCGTTGGCTGGATGCTCAGC

CGGCGAAATCGGTGGTTTATGTCGCACTGGGCAGCGAAGTGCCGCTGGGTGTCGA

AAAAGTGCACGAACTGGCCCTGGGCCTGGAACTGGCAGGCACCCGCTTTCTGTGG

GCACTGCGTAAACCGACGGGCGTTAGCGATGCTGACCTGCTGCCGGCGGGTTTCG

AAGAACGCACCCGCGGCCGTGGTGTCGTGGCCACCCGTTGGGTGCCGCAAATGTC

CATTCTGGCTCATGCGGCCGTTGGCGCATTTCTGACCCACTGCGGTTGGAACAGCA

CGATCGAAGGCCTGATGTTTGGTCATCCGCTGATTATGCTGCCGATCTTCGGCGAT

CAGGGTCCGAACGCACGCCTGATCGAAGCCAAAAATGCAGGCCTGCAAGTTGCGC

GTAACGATGGCGACGGTAGCTTTGACCGCGAAGGTGTCGCAGCTGCGATTCGTGC

TGTGGCGGTTGAAGAAGAAAGCAGCAAAGTCTTCCAGGCCAAAGCGAAAAAACT

GCAAGAAATCGTGGCTGATATGGCGTGTCATGAACGCTATATTGACGGCTTTATCC

AGCAACTGCGTTCTTACAAAGATGACAGTGGCTATAGTTCCTCATACGCCGCAGCT

GCGGGTATGCATGTTGTCATTTGCCCGTGGCTGGCGTTTGGTCACCTGCTGCCGTG

TCTGGATCTGGCACAGCGCCTGGCATCTCGCGGTCACCGTGTTTCGTTCGTCAGCA

CCCCGCGCAATATCAGTCGTCTGCCGCCGGTTCGTCCGGCGCTGGCGCCGCTGGTT

GCGTTCGTTGCACTGCCGCTGCCGCGTGTGGAAGGTCTGCCGGATGGTGCCGAATC

GACCAACGACGTTCCGCATGATCGTCCGGACATGGTCGAACTGCATCGTCGCGCCT

TTGATGGCCTGGCCGCACCGTTTAGCGAATTTCTGGGTACGGCCTGCGCAGATTGG

GTCATTGTGGACGTTTTTCACCACTGGGCGGCGGCGGCGGCTGGAACATAAAG

TGCCGTGTGCGATGATGCTGCTGGGTTCCGCCCACATGATTGCTTCAATCGCGGAT

CGTCGCCTGGAACGTGCCGAAACCGAAAGTCCGGCGGCGGCAGGCCAGGGTCGTC

CGGCGGCGGCACCGACCTTTGAAGTGGCACGTATGAAACTGATTCGCACGAAATA

A
```

-continued

HV1: Amino Acid sequence
(SEQ ID NO: 5)
MDGNSSSSPLHVVICPWLALGHLLPCLDIAERLASRGHRVSFVSTPRNIARLPPLRPAV

APLVDFVALPLPHVDGLPEGAESTNDVPYDKFELHRKAFDGLAAPFSEFLRAACAEGA

GSRPDWLIVDTFHHWAAAAAVENKVPCVMLLLGAATVIAGFARGVSEHAAAAVGKE

RPAAEAPSFETERRKLMTTQNASGMTVAERYFLTLMRSDLVAIRSCAEWEPESVAALT

TLAGKPVVPLGLLPPSPEGGRGVSKEDAAVRWLDAQPAKSVVYVALGSEVPLRAEQV

HELALGLELSGARFLWALRKPTDAPDAAVLPPGFEERTRGRGLVVTGWVPQIGVLAH

GAVAAFLTHCGWNSTIEGLLFGHPLIMLPISSDQGPNARLMEGRKVGMQVPRDESDGS

FRREDVAATVRAVAVEEDGRRVFTANAKKMQEIVADGACHERCIDGFIQQLRSYKA

HV1: DNA Sequence
(SEQ ID NO: 6)
ATGGATGGTAACTCCTCCTCCTCGCCGCTGCATGTGGTCATTTGTCCGTGGCTGGC

TCTGGGTCACCTGCTGCCGTGTCTGGATATTGCTGAACGTCTGGCGTCACGCGGCC

ATCGTGTCAGTTTTGTGTCCACCCCGCGCAACATTGCCCGTCTGCCGCCGCTGCGT

CCGGCTGTTGCACCGCTGGTTGATTTCGTCGCACTGCCGCTGCCGCATGTTGACGG

TCTGCCGGAGGGTGCGGAATCGACCAATGATGTGCCGTATGACAAATTTGAACTG

CACCGTAAGGCGTTCGATGGTCTGGCGGCCCCGTTTAGCGAATTTCTGCGTGCAGC

TTGCGCAGAAGGTGCAGGTTCTCGCCCGGATTGGCTGATTGTGGACACCTTTCATC

ACTGGGCGGCGGCGGCGGCGGTGGAAAACAAAGTGCCGTGTGTTATGCTGCTGCT

GGGTGCAGCAACGGTGATCGCTGGTTTCGCGCGTGGTGTTAGCGAACATGCGGCG

GCGGCGGTGGGTAAAGAACGTCCGGCTGCGGAAGCCCCGAGTTTTGAAACCGAAC

GTCGCAAGCTGATGACCACGCAGAATGCCTCCGGCATGACCGTGGCAGAACGCTA

TTTCCTGACGCTGATGCGTAGCGATCTGGTTGCCATCCGCTCTTGCGCAGAATGGG

AACCGGAAAGCGTGGCAGCACTGACCACGCTGGCAGGTAAACCGGTGGTTCCGCT

GGGTCTGCTGCCGCCGAGTCCGGAAGGCGGTCGTGGCGTTTCCAAAGAAGATGCT

GCGGTCCGTTGGCTGGACGCACAGCCGGCAAAGTCAGTCGTGTACGTCGCACTGG

GTTCGGAAGTGCCGCTGCGTGCGGAACAAGTTCACGAACTGGCACTGGGCCTGGA

ACTGAGCGGTGCTCGCTTTCTGTGGGCGCTGCGTAAACCGACCGATGCACCGGAC

GCCGCAGTGCTGCCGCCGGGTTTCGAAGAACGTACCCGCGGCCGTGGTCTGGTTGT

CACGGGTTGGGTGCCGCAGATTGGCGTTCTGGCTCATGGTGCGGTGGCTGCGTTTC

TGACCCACTGTGGCTGGAACTCTACGATCGAAGGCCTGCTGTTCGGTCATCCGCTG

ATTATGCTGCCGATCAGCTCTGATCAGGGTCCGAATGCGCGCCTGATGGAAGGCC

GTAAAGTCGGTATGCAAGTGCCGCGTGATGAATCAGACGGCTCGTTTCGTCGCGA

AGATGTTGCCGCAACCGTCCGCGCCGTGGCAGTTGAAGAAGACGGTCGTCGCGTC

TTCACGGCTAACGCGAAAAAGATGCAAGAAATTGTGGCCGATGGCGCATGCCACG

AACGTTGTATTGACGGTTTTATCCAGCAACTGCGCAGTTACAAGGCGTAA

UGT76G1: Amino Acid sequence
(SEQ ID NO: 7)
MENKTETTVRRRRRIILFPVPFQGHINPILQLANVLYSKGFSITIFHTNFNKPKTSNYPHF

TFRFILDNDPQDERISNLPTHGPLAGMRIPIINEHGADELRRELELLMLASEEDEEVSCLI

TDALWYFAQSVADSLNLRRLVLMTSSLFNFHAHVSLPQFDELGYLDPDDKTRLEEQA

SGFPMLKVKDIKSAYSNWQILKEILGKMIKQTKASSGVIWNSFKELEESELETVIREIPA

PSFLIPLPKHLTASSSSLLDHDRTVFQWLDQQPPSSVLYVSFGSTSEVDEKDFLEIARGL

-continued

VDSKQSFLWVVRPGFVKGSTWVEPLPDGFLGERGRIVKWVPQQEVLAHGAIGAFWT

HSGWNSTLESVCEGVPMIFSDFGLDQPLNARYMSDVLKVGVYLENGWERGEIANAIR

RVMVDEEGEYIRQNARVLKQKADVSLMKGGSSYESLESLVSYISSL

UGT76G1: DNA Sequence
(SEQ ID NO: 8)
ATGGAGAATAAGACAGAAACAACCGTAAGACGGAGGCGGAGGATTATCTTGTTCC

CTGTACCATTTCAGGGCCATATTAATCCGATCCTCCAATTAGCAAACGTCCTCTAC

TCCAAGGGATTTTCAATAACAATCTTCCATACTAACTTTAACAAGCCTAAAACGAG

TAATTATCCTCACTTTACATTCAGGTTCATTCTAGACAACGACCCTCAGGATGAGC

GTATCTCAAATTTACCTACGCATGGCCCCTTGGCAGGTATGCGAATACCAATAATC

AATGAGCATGGAGCCGATGAACTCCGTCGCGAGTTAGAGCTTCTCATGCTCGCAA

GTGAGGAAGACGAGGAAGTTTCGTGCCTAATAACTGATGCGCTTTGGTACTTCGCC

CAATCAGTCGCAGACTCACTGAATCTACGCCGTTTGGTCCTTATGACAAGTTCATT

ATTCAACTTTCACGCACATGTATCACTGCCGCAATTTGACGAGTTGGGTTACCTGG

ACCCGGATGACAAAACGCGATTGGAGGAACAAGCGTCGGGCTTCCCCATGCTGAA

AGTCAAAGATATTAAGAGCGCTTATAGTAATTGGCAAATTCTGAAAGAAATTCTC

GGAAAAATGATAAAGCAAACCAAAGCGTCCTCTGGAGTAATCTGGAACTCCTTCA

AGGAGTTAGAGGAATCTGAACTTGAAACGGTCATCAGAGAAATCCCCGCTCCCTC

GTTCTTAATTCCACTACCCAAGCACCTTACTGCAAGTAGCAGTTCCTCCTAGATC

ATGACCGAACCGTGTTTCAGTGGCTGGATCAGCAACCCCGTCGTCAGTTCTATAT

GTAAGCTTTGGGAGTACTTCGGAAGTGGATGAAAAGGACTTCTTAGAGATTGCGC

GAGGGCTCGTGGATAGCAAACAGAGCTTCCTGTGGGTAGTGAGACCGGGATTCGT

TAAGGGCTCGACGTGGGTCGAGCCGTTGCCAGATGGTTTTCTAGGGGAGAGAGGG

AGAATCGTGAAATGGGTTCCACAGCAAGAGGTTTTGGCTCACGGAGCTATAGGGG

CCTTTTGGACCCACTCTGGTTGGAATTCTACTCTTGAAAGTGTCTGTGAAGGCGTT

CCAATGATATTTTCTGATTTTGGGCTTGACCAGCCTCTAAACGCTCGCTATATGTCT

GATGTGTTGAAGGTTGGCGTGTACCTGGAGAATGGTTGGGAAGGGGGGAAATTG

CCAACGCCATACGCCGGGTAATGGTGGACGAGGAAGGTGAGTACATACGTCAGAA

CGCTCGGGTTTTAAAACAAAAAGCGGACGTCAGCCTTATGAAGGGAGGTAGCTCC

TATGAATCCCTAGAATCCTTGGTAAGCTATATATCTTCGTTATAA

UGT2E-B: Amino Acid sequence
(SEQ ID NO: 9)
MATSDSIVDDRKQLHVATFPWLAFGHILPYLQLSKLIAEKGHKVSFLSTTRNIQRLSSHI

SPLINVVQLTLPRVQELPEDAEATTDVHPEDIPYLKKASDGLQPEVTRFLEQHSPDWIIY

DYTHYWLPSIAASLGISRAHFSVTTPWAIAYMGPSADAMINGSDGRTTVEDLTTPPKW

FPFPTKVCWRKHDLARLVPYKAPGISDGYRMGMVLKGSDCLLSKCYHEFGTQWLPLL

ETLHQVPVVPVGLLPPEIPGDEKDETWVSIKKWLDGKQKGSVVYVALGSEALVSQTE

VVELALGLELSGLPFVWAYRKPKGPAKSDSVELPDGFVERTRDRGLVWTSWAPQLRI

LSHESVCGFLTHCGSGSIVEGLMFGHPLIMLPIFGDQPLNARLLEDKQVGIEIPRNEEDG

CLTKESVARSLRSVVVEKEGEIYKANARELSKIYNDTKVEKEYVSQFVDYLEKNARA

VAIDHES

-continued

UGT2E-B: DNA Sequence (SEQ ID NO: 10)

ATGGCTACCAGTGACTCCATAGTTGACGACCGTAAGCAGCTTCATGTTGCGACGTT

CCCATGGCTTGCTTTCGGTCACATCCTCCCTTACCTTCAGCTTTCGAAATTGATAGC

TGAAAAGGGTCACAAAGTCTCGTTTCTTTCTACCACCAGAAACATTCAACGTCTCT

CTTCTCATATCTCGCCACTCATAAATGTTGTTCAACTCACACTTCCACGTGTCCAAG

AGCTGCCGGAGGATGCAGAGGCGACCACTGACGTCCACCCTGAAGATATTCCATA

TCTCAAGAAGGCTTCTGATGGTCTTCAACCGGAGGTCACCCGGTTTCTAGAACAAC

ACTCTCCGGACTGGATTATTTATGATTATACTCACTACTGGTTGCCATCCATCGCG

GCTAGCCTCGGTATCTCACGAGCCCACTTCTCCGTCACCACTCCATGGGCCATTGC

TTATATGGGACCCTCAGCTGACGCCATGATAAATGGTTCAGATGGTCGAACCACG

GTTGAGGATCTCACGACACCGCCCAAGTGGTTTCCCTTTCCGACCAAAGTATGCTG

GCGGAAGCATGATCTTGCCCGACTGGTGCCTTACAAAGCTCCGGGGATATCTGAT

GGATACCGTATGGGGATGGTTCTTAAGGGATCTGATTGTTTGCTTTCCAAATGTTA

CCATGAGTTTGGAACTCAATGGCTACCTCTTTTGGAGACACTACACCAAGTACCGG

TGGTTCCGGTGGGATTACTGCCACCGGAAATACCCGGAGACGAGAAAGATGAAAC

ATGGGTGTCAATCAAGAAATGGCTCGATGGTAAACAAAAAGGCAGTGTGGTGTAC

GTTGCATTAGGAAGCGAGGCTTTGGTGAGCCAAACCGAGGTTGTTGAGTTAGCAT

TGGGTCTCGAGCTTTCTGGGTTGCCATTTGTTTGGGCTTATAGAAAACCAAAAGGT

CCCGCGAAGTCAGACTCGGTGGAGTTGCCAGACGGGTTCGTGGAACGAACTCGTG

ACCGTGGGTTGGTCTGGACGAGTTGGGCACCTCAGTTACGAATACTGAGCCATGA

GTCGGTTTGTGGTTTCTTGACTCATTGTGGTTCTGGATCAATTGTGGAAGGGCTAA

TGTTTGGTCACCCTCTAATCATGCTACCGATTTTTGGGGACCAACCTCTGAATGCTC

GATTACTGGAGGACAAACAGGTGGGAATCGAGATACCAAGAAATGAGGAAGATG

GTTGCTTGACCAAGGAGTCGGTTGCTAGATCACTGAGGTCCGTTGTTGTGGAAAAA

GAAGGGGAGATCTACAAGGCGAACGCGAGGGAGCTGAGTAAAATCTATAACGAC

ACTAAGGTTGAAAAAGAATATGTAAGCCAATTCGTAGACTATTTGGAAAAGAATG

CGCGTGCGGTTGCCATCGATCATGAGAGTTAA

CP1: Amino Acid sequence (SEQ ID NO: 11)

MNWQILKEILGKMIKQTKASSGVIWNSFKELEESELETVIREIPAPSFLIPLPKHLTASSS

SLLDHDRTVFQWLDQQPPSSVLYVSFGSTSEVDEKDFLEIARGLVDSKQSFLWVVRPG

FVKGSTWVEPLPDGFLGERGRIVKWVPQQEVLAHGAIGAFWTHSGWNSTLESVCEGV

PMIFSDFGLDQPLNARYMSDVLKVGVYLENGWERGEIANAIRRVMVDEEGEYIRQNA

RVLKQKADVSLMKGGSSYESLESLVSYISSLENKTETTVRRRRIILFPVPFQGHINPIL

QLANVLYSKGFSITIFHTNFNKPKTSNYPHFTFRFILDNDPQDERISNLPTHGPLAGMRI

PIINEHGADELRRELELLMLASEEDEEVSCLITDALWYFAQSVADSLNLRRLVLMTSSL

FNFHAHVSLPQFDELGYLDPDDKTRLEEQASGFPMLKVKDIKSAYS

CP1: DNA Sequence (SEQ ID NO: 12)

ATGAACTGGCAAATCCTGAAAGAAATCCTGGGTAAAATGATCAAACAAACCAAAG

CGTCGTCGGGCGTTATCTGGAACTCCTTCAAAGAACTGGAAGAATCAGAACTGGA

AACCGTTATTCGCGAAATCCCGGCTCCGTCGTTCCTGATTCCGCTGCCGAAACATC

TGACCGCGAGCAGCAGCAGCCTGCTGGATCACGACCGTACGGTCTTTCAGTGGCT

-continued

```
GGATCAGCAACCGCCGTCATCGGTGCTGTATGTTTCATTCGGTAGCACCTCTGAAG

TCGATGAAAAAGACTTTCTGGAAATCGCTCGCGGCCTGGTGGATAGTAAACAGTC

CTTCCTGTGGGTGGTTCGTCCGGGTTTTGTGAAAGGCAGCACGTGGGTTGAACCGC

TGCCGGATGGCTTCCTGGGTGAACGCGGCCGTATTGTCAAATGGGTGCCGCAGCA

AGAAGTGCTGGCACATGGTGCTATCGGCGCGTTTTGGACCCACTCTGGTTGGAACA

GTACGCTGGAATCCGTTTGCGAAGGTGTCCCGATGATTTTCAGCGATTTTGGCCTG

GACCAGCCGCTGAATGCCCGCTATATGTCTGATGTTCTGAAAGTCGGTGTGTACCT

GGAAAACGGTTGGGAACGTGGCGAAATTGCGAATGCCATCCGTCGCGTTATGGTC

GATGAAGAAGGCGAATACATTCGCCAGAACGCTCGTGTCCTGAAACAAAAAGCGG

ACGTGAGCCTGATGAAAGGCGGTAGCTCTTATGAATCACTGGAATCGCTGGTTAG

CTACATCAGTTCCCTGGAAAATAAAACCGAAACCACGGTGCGTCGCCGTCGCCGT

ATTATCCTGTTCCCGGTTCCGTTTCAGGGTCATATTAACCCGATCCTGCAACTGGC

GAATGTTCTGTATTCAAAAGGCTTTTCGATCACCATCTTCCATACGAACTTCAACA

AACCGAAAACCAGTAACTACCCGCACTTTACGTTCCGCTTTATTCTGGATAACGAC

CCGCAGGATGAACGTATCTCCAATCTGCCGACCCACGGCCCGCTGGCCGGTATGC

GCATTCCGATTATCAATGAACACGGTGCAGATGAACTGCGCCGTGAACTGGAACT

GCTGATGCTGGCCAGTGAAGAAGATGAAGAAGTGTCCTGTCTGATCACCGACGCA

CTGTGGTATTTCGCCCAGAGCGTTGCAGATTCTCTGAACCTGCGCCGTCTGGTCCT

GATGACGTCATCGCTGTTCAATTTTCATGCGCACGTTTCTCTGCCGCAATTTGATGA

ACTGGGCTACCTGGACCCGGATGACAAAACCCGTCTGGAAGAACAAGCCAGTGGT

TTTCCGATGCTGAAAGTCAAAGACATTAAATCCGCCTATTCGTAA
```

CP2: Amino Acid sequence (SEQ ID NO: 13)

```
MNWQILKEILGKMIKQTKASSGVIWNSFKELEESELETVIREIPAPSFLIPLPKHLTASSS

SLLDHDRTVFQWLDQQPPSSVLYVSFGSTSEVDEKDFLEIARGLVDSKQSFLWVVRPG

FVKGSTWVEPLPDGFLGERGRIVKWVPQQEVLAHGAIGAFWTHSGWNSTLESVCEGV

PMIFSDFGLDQPLNARYMSDVLKVGVYLENGWERGEIANAIRRVMVDEEGEYIRQNA

RVLKQKADVSLMKGGSSYESLESLVSYISSLYKDDSGYSSSYAAAAGMENKTETTVR

RRRRIILFPVPFQGHINPILQLANVLYSKGFSITIFHTNFNKPKTSNYPHFTFRFILDNDPQ

DERISNLPTHGPLAGMRIPIINEHGADELRRELELLMLASEEDEEVSCLITDALWYFAQS

VADSLNLRRLVLMTSSLFNFHAHVSLPQFDELGYLDPDDKTRLEEQASGFPMLKVKDI

KSAYS
```

CP2: DNA Sequence (SEQ ID NO: 14)

```
ATGAACTGGCAAATCCTGAAAGAAATCCTGGGTAAAATGATCAAACAAACCAAAG

CGTCGTCGGGCGTTATCTGGAACTCCTTCAAAGAACTGGAAGAATCAGAACTGGA

AACCGTTATTCGCGAAATCCCGGCTCCGTCGTTCCTGATTCCGCTGCCGAAACATC

TGACCGCGAGCAGCAGCAGCCTGCTGGATCACGACCGTACGGTCTTTCAGTGGCT

GGATCAGCAACCGCCGTCATCGGTGCTGTATGTTTCATTCGGTAGCACCTCTGAAG

TCGATGAAAAAGACTTTCTGGAAATCGCTCGCGGCCTGGTGGATAGTAAACAGTC

CTTCCTGTGGGTGGTTCGTCCGGGTTTTGTGAAAGGCAGCACGTGGGTTGAACCGC

TGCCGGATGGCTTCCTGGGTGAACGCGGCCGTATTGTCAAATGGGTGCCGCAGCA
```

```
                                                      -continued
AGAAGTGCTGGCACATGGTGCTATCGGCGCGTTTTGGACCCACTCTGGTTGGAACA

GTACGCTGGAATCCGTTTGCGAAGGTGTCCCGATGATTTTCAGCGATTTTGGCCTG

GACCAGCCGCTGAATGCCCGCTATATGTCTGATGTTCTGAAAGTCGGTGTGTACCT

GGAAAACGGTTGGGAACGTGGCGAAATTGCGAATGCCATCCGTCGCGTTATGGTC

GATGAAGAAGGCGAATACATTCGCCAGAACGCTCGTGTCCTGAAACAAAAAGCGG

ACGTGAGCCTGATGAAAGGCGGTAGCTCTTATGAATCACTGGAATCGCTGGTTAG

CTACATCAGTTCCCTGTACAAAGATGACAGCGGTTATAGCAGCAGCTATGCGGCG

GCGGCGGGTATGGAAAATAAAACCGAAACCACGGTGCGTCGCCGTCGCCGTATTA

TCCTGTTCCCGGTTCCGTTTCAGGGTCATATTAACCCGATCCTGCAACTGGCGAAT

GTTCTGTATTCAAAAGGCTTTTCGATCACCATCTTCCATACGAACTTCAACAAACC

GAAAACCAGTAACTACCCGCACTTTACGTTCCGCTTTATTCTGGATAACGACCCGC

AGGATGAACGTATCTCCAATCTGCCGACCCACGGCCCGCTGGCCGGTATGCGCATT

CCGATTATCAATGAACACGGTGCAGATGAACTGCGCCGTGAACTGGAACTGCTGA

TGCTGGCCAGTGAAGAAGATGAAGAAGTGTCCTGTCTGATCACCGACGCACTGTG

GTATTTCGCCCAGAGCGTTGCAGATTCTCTGAACCTGCGCCGTCTGGTCCTGATGA

CGTCATCGCTGTTCAATTTTCATGCGCACGTTTCTCTGCCGCAATTTGATGAACTGG

GCTACCTGGACCCGGATGACAAAACCCGTCTGGAAGAACAAGCCAGTGGTTTTCC

GATGCTGAAAGTCAAAGACATTAAATCCGCCTATTCGTAA
```

GS: Amino Acid sequence
(SEQ ID NO: 15)
```
MENKTETTVRRRRRIILFPVPFQGHINPILQLANVLYSKGFSITIFHTNFNKPKTSNYPHF

TFRFILDNDPQDERISNLPTHGPLAGMRIPIINEHGADELRRELELLMLASEEDEEVSCLI

TDALWYFAQSVADSLNLRRLVLMTSSLFNFHAHVSLPQFDELGYLDPDDKTRLEEQA

SGFPMLKVKDIKSAYSNWQILKEILGKMIKQTKASSGVIWNSFKELEESELETVIREIPA

PSFLIPLPKHLTASSSSLLDHDRTVFQWLDQQPPSSVLYVSFGSTSEVDEKDFLEIARGL

VDSKQSFLWVVRPGFVKGSTWVEPLPDGFLGERGRIVKWVPQQEVLAHGAIGAFWT

HSGWNSTLESVCEGVPMIFSDFGLDQPLNARYMSDVLKVGVYLENGWERGEIANAIR

RVMVDEEGEYIRQNARVLKQKADVSLMKGGSSYESLESLVSYISSLGSGANAERMITR

VHSQRERLNETLVSERNEVLALLSRVEAKGKGILQQNQIIAEFEALPEQTRKKLEGGPF

FDLLKSTQEAIVLPPWVALAVRPRPGVWEYLRVNLHALVVEELQPAEFLHFKEELVD

GVKNGNFTLELDFEPFNASIPRPTLHKYIGNGVDFLNRHLSAKLFHDKESLLPLLKFLR

LHSHQGKNLMLSEKIQNLNTLQHTLRKAEEYLAELKSETLYEEFEAKFEEIGLERGWG

DNAERVLDMIRLLLDLLEAPDPCTLETFLGRVPMVFNVVILSPHGYFAQDNVLGYPDT

GGQVVYILDQVRALEIEMLQRIKQQGLNIKPRILILTRLLPDAVGTTCGERLERVYDSE

YCDILRVPFRTEKGIVRKWISRFEVWPYLETYTEDAAVELSKELNGKPDLIIGNYSDGN

LVASLLAHKLGVTQCTIAHALEKTKYPDSDIYWKKLDDKYHFSCQFTADIFAMNHTD

FIITSTFQEIAGSKETVGQYESHTAFTLPGLYRVVHGIDVFDPKFNIVSPGADMSIYFPYT

EEKRRLTKFHSEIEELLYSDVENKEHLCVLKDKKKPILFTMARLDRVKNLSGLVEWYG

KNTRLRELANLVVVGGDRRKESKDNEEKAEMKKMYDLIEEYKLNGQFRWISSQMDR

VRNGELYRYICDTKGAFVQPALYEAFGLTVVEAMTCGLPTFATCKGGPAEIIVHGKSG

FHIDPYHGDQAADTLADFFTKCKEDPSHWDEISKGGLQRIEEKYTWQIYSQRLLTLTG

VYGFWKHVSNLDRLEARRYLEMFYALKYRPLAQAVPLAQDD
```

GS: DNA Sequence (SEQ ID NO: 16)

ATGGAGAATAAGACAGAAACAACCGTAAGACGGAGGCGGAGGATTATCTTGTTCC

CTGTACCATTTCAGGGCCATATTAATCCGATCCTCCAATTAGCAAACGTCCTCTAC

TCCAAGGGATTTTCAATAACAATCTTCCATACTAACTTTAACAAGCCTAAAACGAG

TAATTATCCTCACTTTACATTCAGGTTCATTCTAGACAACGACCCTCAGGATGAGC

GTATCTCAAATTTACCTACGCATGGCCCCTTGGCAGGTATGCGAATACCAATAATC

AATGAGCATGGAGCCGATGAACTCCGTCGCGAGTTAGAGCTTCTCATGCTCGCAA

GTGAGGAAGACGAGGAAGTTTCGTGCCTAATAACTGATGCGCTTTGGTACTTCGCC

CAATCAGTCGCAGACTCACTGAATCTACGCCGTTTGGTCCTTATGACAAGTTCATT

ATTCAACTTTCACGCACATGTATCACTGCCGCAATTTGACGAGTTGGGTTACCTGG

ACCCGGATGACAAAACGCGATTGGAGGAACAAGCGTCGGGCTTCCCCATGCTGAA

AGTCAAAGATATTAAGAGCGCTTATAGTAATTGGCAAATTCTGAAAGAAATTCTC

GGAAAAATGATAAAGCAAACCAAAGCGTCCTCTGGAGTAATCTGGAACTCCTTCA

AGGAGTTAGAGGAATCTGAACTTGAAACGGTCATCAGAGAAATCCCCGCTCCCTC

GTTCTTAATTCCACTACCCAAGCACCTTACTGCAAGTAGCAGTTCCCTCCTAGATC

ATGACCGAACCGTGTTTCAGTGGCTGGATCAGCAACCCCCGTCGTCAGTTCTATAT

GTAAGCTTTGGGAGTACTTCGGAAGTGGATGAAAAGGACTTCTTAGAGATTGCGC

GAGGGCTCGTGGATAGCAAACAGAGCTTCCTGTGGGTAGTGAGACCGGGATTCGT

TAAGGGCTCGACGTGGGTCGAGCCGTTGCCAGATGGTTTTCTAGGGGAGAGAGGG

AGAATCGTGAAATGGGTTCCACAGCAAGAGGTTTTGGCTCACGGAGCTATAGGGG

CCTTTTGGACCCACTCTGGTTGGAATTCTACTCTTGAAAGTGTCTGTGAAGGCGTT

CCAATGATATTTTCTGATTTTGGGCTTGACCAGCCTCTAAACGCTCGCTATATGTCT

GATGTGTTGAAGGTTGGCGTGTACCTGGAGAATGGTTGGGAAAGGGGGGAAATTG

CCAACGCCATACGCCGGGTAATGGTGGACGAGGAAGGTGAGTACATACGTCAGAA

CGCTCGGGTTTTAAAACAAAAAGCGGACGTCAGCCTTATGAAGGGAGGTAGCTCC

TATGAATCCCTAGAATCCTTGGTAAGCTATATATCTTCGTTAGGTTCTGGTGCAAA

CGCTGAACGTATGATAACGCGCGTCCACAGCCAACGTGAGCGTTTGAACGAAACG

CTTGTTTCTGAGAGAAACGAAGTCCTTGCCTTGCTTTCCAGGGTTGAAGCCAAAGG

TAAAGGTATTTTACAACAAAACCAGATCATTGCTGAATTCGAAGCTTTGCCTGAAC

AAACCCGGAAGAAACTTGAAGGTGGTCCTTTCTTTGACCTTCTCAAATCCACTCAG

GAAGCAATTGTGTTGCCACCATGGGTTGCTCTAGCTGTGAGGCCAAGGCCTGGTGT

TTGGGAATACTTACGAGTCAATCTCCATGCTCTTGTCGTTGAAGAACTCCAACCTG

CTGAGTTTCTTCATTTCAAGGAAGAACTCGTTGATGGAGTTAAGAATGGTAATTTC

ACTCTTGAGCTTGATTTCGAGCCATTCAATGCGTCTATCCCTCGTCCAACACTCCAC

AAATACATTGGAAATGGTGTTGACTTCCTTAACCGTCATTTATCGGCTAAGCTCTT

CCATGACAAGGAGAGTTTGCTTCCATTGCTTAAGTTCCTTCGTCTTCACAGCCACC

AGGGCAAGAACCTGATGTTGAGCGAGAAGATTCAGAACCTCAACACTCTGCAACA

CACCTTGAGGAAAGCAGAAGAGTATCTAGCAGAGCTTAAGTCCGAAACACTGTAT

GAAGAGTTTGAGGCCAAGTTTGAGGAGATTGGTCTTGAGAGGGGATGGGGAGACA

ATGCAGAGCGTGTCCTTGACATGATACGTCTTCTTTTGGACCTTCTTGAGGCGCCT

-continued

```
GATCCTTGCACTCTTGAGACTTTTCTTGGAAGAGTACCAATGGTGTTCAACGTTGT
GATCCTCTCTCCACATGGTTACTTTGCTCAGGACAATGTTCTTGGTTACCCTGACAC
TGGTGGACAGGTTGTTTACATTCTTGATCAAGTTCGTGCTCTGGAGATAGAGATGC
TTCAACGTATTAAGCAACAAGGACTCAACATTAAACCAAGGATTCTCATTCTAACT
CGACTTCTACCTGATGCGGTAGGAACTACATGCGGTGAACGTCTCGAGAGAGTTT
ATGATTCTGAGTACTGTGATATTCTTCGTGTGCCCTTCAGAACAGAGAAGGGTATT
GTTCGCAAATGGATCTCAAGGTTCGAAGTCTGGCCATATCTAGAGACTTACACCGA
GGATGCTGCGGTTGAGCTATCGAAAGAATTGAATGGCAAGCCTGACCTTATCATT
GGTAACTACAGTGATGGAAATCTTGTTGCTTCTTTATTGGCTCACAAACTTGGTGT
CACTCAGTGTACCATTGCTCATGCTCTTGAGAAAACAAAGTACCCGGATTCTGATA
TCTACTGGAAGAAGCTTGACGACAAGTACCATTTCTCATGCCAGTTCACTGCGGAT
ATTTTCGCAATGAACCACACTGATTTCATCATCACTAGTACTTTCCAAGAAATTGC
TGGAAGCAAAGAAACTGTTGGGCAGTATGAAAGCCACACAGCCTTTACTCTTCCC
GGATTGTATCGAGTTGTTCACGGGATTGATGTGTTTGATCCCAAGTTCAACATTGT
CTCTCCTGGTGCTGATATGAGCATCTACTTCCCTTACACAGAGGAGAAGCGTAGAT
TGACTAAGTTCCACTCTGAGATCGAGGAGCTCCTCTACAGCGATGTTGAGAACAA
AGAGCACTTATGTGTGCTCAAGGACAAGAAGAAGCCGATTCTCTTCACAATGGCT
AGGCTTGATCGTGTCAAGAACTTGTCAGGTCTTGTTGAGTGGTACGGGAAGAACA
CCCGCTTGCGTGAGCTAGCTAACTTGGTTGTTGTTGGAGGAGACAGGAGGAAAGA
GTCAAAGGACAATGAAGAGAAAGCAGAGATGAAGAAAATGTATGATCTCATTGA
GGAATACAAGCTAAACGGTCAGTTCAGGTGGATCTCCTCTCAGATGGACCGGGTA
AGGAACGGTGAGCTGTACCGGTACATCTGTGACACCAAGGGTGCTTTTGTCCAAC
CTGCATTATATGAAGCCTTTGGGTTAACTGTTGTGGAGGCTATGACTTGTGGTTTA
CCGACTTTCGCCACTTGCAAAGGTGGTCCAGCTGAGATCATTGTGCACGGTAAATC
GGGTTTCCACATTGACCCTTACCATGGTGATCAGGCTGCTGATACTCTTGCTGATTT
CTTCACCAAGTGTAAGGAGGATCCATCTCACTGGGATGAGATCTCAAAAGGAGGG
CTTCAGAGGATTGAGGAGAAATACACTTGGCAAATCTATTCACAGAGGCTCTTGA
CATTGACTGGTGTGTATGGATTCTGGAAGCATGTCTCGAACCTTGACCGTCTTGAG
GCTCGCCGTTACCTTGAAATGTTCTATGCATTGAAGTATCGCCCATTGGCTCAGGC
TGTTCCTCTTGCACAAGATGATTGA
```

AtSUS1: Amino Acid sequence
(SEQ ID NO: 17)

```
MANAERMITRVHSQRERLNETLVSERNEVLALLSRVEAKGKGILQQNQIIAEFEALPE
QTRKKLEGGPFFDLLKSTQEAIVLPPWVALAVRPRPGVWEYLRVNLHALVVEELQPA
EFLHFKEELVDGVKNGNFTLELDFEPFNASIPRPTLHKYIGNGVDFLNRHLSAKLFHDK
ESLLPLLKFLRLHSHQGKNLMLSEKIQNLNTLQHTLRKAEEYLAELKSETLYEEFEAKF
EEIGLERGWGDNAERVLDMIRLLLDLLEAPDPCTLETFLGRVPMVFNVVILSPHGYFA
QDNVLGYPDTGGQVVYILDQVRALEIEMLQRIKQQGLNIKPRILILTRLLPDAVGTTCG
ERLERVYDSEYCDILRVPFRTEKGIVRKWISRFEVWPYLETYTEDAAVELSKELNGKP
DLIIGNYSDGNLVASLLAHKLGVTQCTIAHALEKTKYPDSDIYWKKLDDKYHFSCQFT
ADIFAMNHTDFIITSTFQEIAGSKETVGQYESHTAFTLPGLYRVVHGIDVFDPKFNIVSP
GADMSIYFPYTEEKRRLTKFHSEIEELLYSDVENKEHLCVLKDKKKPILFTMARLDRV
```

KNLSGLVEWYGKNTRLRELANLVVVGGDRRKESKDNEEKAEMKKMYDLIEEYKLN

GQFRWISSQMDRVRNGELYRYICDTKGAFVQPALYEAFGLTVVEAMTCGLPTFATCK

GGPAEIIVHGKSGFHIDPYHGDQAADTLADFFTKCKEDPSHWDEISKGGLQRIEEKYT

WQIYSQRLLTLTGVYGFWKHVSNLDRLEARRYLEMFYALKYRPLAQAVPLAQDD

AtSUS1: DNA Sequence (SEQ ID NO: 18)

ATGGCAAACGCTGAACGTATGATTACCCGTGTCCACTCCCAACGCGAACGCCTGA

ACGAAACCCTGGTGTCGGAACGCAACGAAGTTCTGGCACTGCTGAGCCGTGTGGA

AGCTAAGGGCAAAGGTATTCTGCAGCAAAACCAGATTATCGCGGAATTTGAAGCC

CTGCCGGAACAAACCCGCAAAAAGCTGGAAGGCGGTCCGTTTTTCGATCTGCTGA

AATCTACGCAGGAAGCGATCGTTCTGCCGCCGTGGGTCGCACTGGCAGTGCGTCC

GCGTCCGGGCGTTTGGGAATATCTGCGTGTCAACCTGCATGCACTGGTGGTTGAAG

AACTGCAGCCGGCTGAATTTCTGCACTTCAAGGAAGAACTGGTTGACGGCGTCAA

AAACGGTAATTTTACCCTGGAACTGGATTTTGAACCGTTCAATGCCAGTATCCCGC

GTCCGACGCTGCATAAATATATTGGCAACGGTGTGGACTTTCTGAATCGCCATCTG

AGCGCAAAGCTGTTCCACGATAAAGAATCTCTGCTGCCGCTGCTGAAATTCCTGCG

TCTGCATAGTCACCAGGGCAAGAACCTGATGCTGTCCGAAAAAATTCAGAACCTG

AATACCCTGCAACACACGCTGCGCAAGGCGGAAGAATACCTGGCCGAACTGAAAA

GTGAAACCCTGTACGAAGAATTCGAAGCAAAGTTCGAAGAAATTGGCCTGGAACG

TGGCTGGGGTGACAATGCTGAACGTGTTCTGGATATGATCCGTCTGCTGCTGGACC

TGCTGGAAGCACCGGACCCGTGCACCCTGGAAACGTTTCTGGGTCGCGTGCCGAT

GGTTTTCAACGTCGTGATTCTGTCCCCGCATGGCTATTTTGCACAGGACAATGTGC

TGGGTTACCCGGATACCGGCGGTCAGGTTGTCTATATTCTGGATCAAGTTCGTGCG

CTGGAAATTGAAATGCTGCAGCGCATCAAGCAGCAAGGCCTGAACATCAAACCGC

GTATTCTGATCCTGACCCGTCTGCTGCCGGATGCAGTTGGTACCACGTGCGGTGAA

CGTCTGGAACGCGTCTATGACAGCGAATACTGTGATATTCTGCGTGTCCCGTTTCG

CACCGAAAAGGGTATTGTGCGTAAATGGATCAGTCGCTTCGAAGTTTGGCCGTATC

TGGAAACCTACACGGAAGATGCGGCCGTGGAACTGTCCAAGGAACTGAATGGCAA

ACCGGACCTGATTATCGGCAACTATAGCGATGGTAATCTGGTCGCATCTCTGCTGG

CTCATAAACTGGGTGTGACCCAGTGCACGATTGCACACGCTCTGGAAAAGACCAA

ATATCCGGATTCAGACATCTACTGGAAAAAGCTGGATGACAAATATCATTTTTCGT

GTCAGTTCACCGCGGACATTTTTGCCATGAACCACACGGATTTTATTATCACCAGT

ACGTTCCAGGAAATCGCGGGCTCCAAAGAAACCGTGGGTCAATACGAATCACATA

CCGCCTTCACGCTGCCGGGCCTGTATCGTGTGGTTCACGGTATCGATGTTTTTGAC

CCGAAATTCAATATTGTCAGTCCGGGCGCGGATATGTCCATCTATTTTCCGTACAC

CGAAGAAAAGCGTCGCCTGACGAAATTCCATTCAGAAATTGAAGAACTGCTGTAC

TCGGACGTGGAAAACAAGGAACACCTGTGTGTTCTGAAAGATAAAAAGAAACCG

ATCCTGTTTACCATGGCCCGTCTGGATCGCGTGAAGAATCTGTCAGGCCTGGTTGA

ATGGTATGGTAAAAACACGCGTCTGCGCGAACTGGCAAATCTGGTCGTGGTTGGC

GGTGACCGTCGCAAGGAATCGAAAGATAACGAAGAAAAGGCTGAAATGAAGAAA

ATGTACGATCTGATCGAAGAATACAAGCTGAACGGCCAGTTTCGTTGGATCAGCT

-continued

```
CTCAAATGGACCGTGTGCGCAATGGCGAACTGTATCGCTACATTTGCGATACCAA

GGGTGCGTTTGTTCAGCCGGCACTGTACGAAGCTTTCGGCCTGACCGTCGTGGAAG

CCATGACGTGCGGTCTGCCGACCTTTGCGACGTGTAAAGGCGGTCCGGCCGAAAT

TATCGTGCATGGCAAATCTGGTTTCCATATCGATCCGTATCACGGTGATCAGGCAG

CTGACACCCTGGCGGATTTCTTTACGAAGTGTAAAGAAGACCCGTCACACTGGGA

TGAAATTTCGAAGGGCGGTCTGCAACGTATCGAAGAAAATATACCTGGCAGATT

TACAGCCAACGCCTGCTGACCCTGACGGGCGTCTACGGTTTTTGGAAACATGTGTC

TAATCTGGATCGCCTGGAAGCCCGTCGCTATCTGGAAATGTTTTACGCACTGAAGT

ATCGCCCGCTGGCACAAGCCGTTCCGCTGGCACAGGACGACTAA
```

NX114: Amino Acid Sequence
(SEQ ID NO: 19)
```
MENGSSPLHVVIFPWLAFGHLLPFLDLAERLAARGHRVSFVSTPRNLARLRPVRPALR

GLVDLVALPLPRVHGLPDGAEATSDVPFEKFELHRKAFDGLAAPFSAFLDAACAGDK

RPDWVIPDFMHYWVAAAAQKRGVPCAVLIPCSADVMALYGQPTETSTEQPEAIARSM

AAEAPSFEAERNTEEYGTAGASGVSIMTRFSLTLKWSKLVALRSCPELEPGVFTTLTRV

YSKPVVPFGLLPPRRDGAHGVRKNGEDDGAIIRWLDEQPAKSVVYVALGSEAPVSAD

LLRELAHGLELAGTRFLWALRRPAGVNDGDSILPNGFLERTGERGLVTTGWVPQVSIL

AHAAVCAFLTHCGWGSVVEGLQFGHPLIMLPIIGDQGPNARFLEGRKVGVAVPRNHA

DGSFDRSGVAGAVRAVAVEEEGKAFAANARKLQEIVADRERDERCTDGFIHHLTSWN

ELEA
```

NX114: DNA Sequence
(SEQ ID NO: 20)
```
ATGGAAAATGGTAGCAGTCCGCTGCATGTTGTTATTTTTCCGTGGCTGGCATTTGG

TCATCTGCTGCCGTTTCTGGATCTGGCAGAACGTCTGGCAGCACGTGGTCATCGTG

TTAGCTTTGTTAGCACACCGCGTAATCTGGCACGTCTGCGTCCGGTTCGTCCGGCA

CTGCGTGGTCTGGTTGATCTGGTTGCACTGCCGCTGCCTCGTGTTCATGGTCTGCCG

GATGGTGCCGAAGCAACCAGTGATGTTCCGTTTGAAAAATTTGAACTGCACCGCA

AAGCATTTGATGGCCTGGCTGCACCGTTTAGCGCATTTCTGGATGCAGCATGTGCC

GGTGATAAACGTCCGGATTGGGTTATTCCGGATTTTATGCATTATTGGGTTGCAGC

AGCAGCACAGAAACGTGGTGTTCCGTGTGCAGTTCTGATTCCGTGTAGCGCAGAT

GTTATGGCACTGTATGGTCAGCCGACCGAAACCAGCACCGAACAGCCGGAAGCAA

TTGCACGTAGCATGGCAGCAGAAGCACCGAGCTTTGAAGCAGAACGTAATACCGA

AGAATATGGTACAGCCGGTGCAAGCGGTGTTAGCATTATGACCCGTTTTAGTCTGA

CCCTGAAATGGTCAAAACTGGTTGCCCTGCGTAGCTGTCCGGAACTGGAACCGGG

TGTTTTTACCACACTGACCCGTGTTTATAGCAAACCGGTTGTGCCGTTTGGTCTGCT

GCCTCCGCGTCGTGATGGTGCACATGGTGTTCGTAAAAATGGTGAAGATGATGGT

GCCATTATTCGTTGGCTGGATGAACAGCCTGCAAAAAGCGTTGTTTATGTTGCACT

GGGTAGCGAAGCACCGGTTTCAGCCGATCTGCTGCGTGAACTGGCACATGGTCTG

GAATTAGCAGGCACCCGTTTTCTGTGGGCTCTGCGTCGTCCTGCCGGTGTTAATGA

TGGTGATAGCATTCTGCCGAATGGTTTTCTGGAACGTACCGGTGAACGCGGTCTGG

TTACCACCGGTTGGGTTCCGCAGGTTAGTATTCTGGCCCATGCAGCAGTTTGTGCA

TTTCTGACCCATTGTGGTTGGGGTAGCGTTGTTGAAGGTTTACAGTTTGGCCATCC

GCTGATTATGCTGCCGATTATTGGTGATCAGGGTCCGAATGCACGCTTTCTGGAAG
```

-continued

```
GTCGTAAAGTTGGTGTTGCAGTTCCGCGTAACCATGCAGATGGTAGCTTTGATCGT

AGCGGTGTTGCCGGTGCCGTTCGTGCAGTTGCAGTTGAAGAAGAAGGTAAAGCCT

TTGCAGCAAATGCCCGTAAACTGCAAGAAATTGTTGCAGATCGTGAACGTGATGA

ACGTTGTACCGATGGTTTTATTCATCATCTGACCAGCTGGAATGAACTGGAAGCAT

AA
```

---

What is claimed is:

1. A biosynthetic method of preparing rebaudioside N, the method comprising:
reacting a steviol glycoside composition comprising rebaudioside A with a rhamnose donor moiety in the presence of a first recombinant polypeptide having 1,2-rhamnosytransferase activity to produce rebaudioside J; wherein said first recombinant polypeptide comprises the amino acid sequence of SEQ ID NO: 3; and
reacting said rebaudioside J with a glucose donor moiety in the presence of a second recombinant polypeptide having glucosyltransferase activity to produce rebaudioside N, wherein said second recombinant polypeptide comprises the amino acid sequence of SEQ ID NO: 13.

2. The method of claim 1, comprising expressing said first recombinant polypeptide in a transformed cell.

3. The method of claim 2, wherein the transformed cell is selected from the group consisting of a yeast, a non-steviol glycoside producing plant, an alga, a fungus, and a bacterium.

4. The method of claim 2, wherein the reacting step is performed in the transformed cell.

5. The method of claim 2, comprising isolating said first recombinant polypeptide from the transformed cell and the reacting step is performed in vitro.

6. The method of claim 1, wherein the rhamnose donor moiety is UDP-L-rhamnose.

7. The method of claim 1, comprising reacting said rebaudioside J with the glucose donor moiety in the presence of a third recombinant polypeptide having sucrose synthase activity.

8. The method of claim 1, further comprising isolating rebaudioside N from the steviol glycoside composition.

9. The method of claim 1, further comprising purifying rebaudioside N to obtain a steviol glycoside composition enriched with rebaudioside N.

10. A biosynthetic method of preparing rebaudioside J, the method comprising:
reacting a steviol glycoside composition comprising rebaudioside A with a rhamnose donor moiety in the presence of a recombinant polypeptide having 1,2-rhamnosytransferase activity; wherein said recombinant polypeptide comprises the amino acid sequence of SEQ ID NO: 3.

11. The method of claim 10, comprising expressing said recombinant polypeptide in a transformed cell.

12. The method of claim 11, wherein the transformed cell is selected from the group consisting of a yeast, a non-steviol glycoside producing plant, an alga, a fungus, and a bacterium.

13. The method of claim 11, wherein the reacting step is performed in the transformed cell.

14. The method of claim 11, comprising isolating said recombinant polypeptide from the transformed cell and the reacting step is performed in vitro.

15. The method of claim 10, wherein the rhamnose donor moiety is UDP-L-rhamnose.

16. The method of claim 10, further comprising isolating rebaudioside J from the steviol glycoside composition.

17. The method of claim 10, further comprising purifying rebaudioside J to obtain a steviol glycoside composition enriched with rebaudioside J.

* * * * *